United States Patent
Sheps et al.

(10) Patent No.: US 10,568,738 B2
(45) Date of Patent: Feb. 25, 2020

(54) CONTROLLED STEERING FUNCTIONALITY FOR IMPLANT-DELIVERY TOOL

(71) Applicant: Valtech Cardio, Ltd., Or Yehuda (IL)

(72) Inventors: Tal Sheps, Givat Shmuel (IL); Tal Hammer, Ramat Gan (IL); Ehud Iflah, Tel Aviv-Jaffa (IL); Tal Reich, Moledet (IL); Yaron Herman, Givat Ada (IL); Amir Gross, Moshav Mazor (IL)

(73) Assignee: Valtech Cardio, Ltd., Or Yehuda (IL)

( * ) Notice: Subject to any disclaimer, the term of this patent is extended or adjusted under 35 U.S.C. 154(b) by 240 days.

(21) Appl. No.: 15/667,101

(22) Filed: Aug. 2, 2017

(65) Prior Publication Data

US 2017/0325959 A1    Nov. 16, 2017

Related U.S. Application Data

(63) Continuation of application No. 14/357,040, filed as application No. PCT/IL2012/050451 on Nov. 8, 2012, now Pat. No. 9,724,192.

(60) Provisional application No. 61/557,082, filed on Nov. 8, 2011.

(51) Int. Cl.
*A61M 25/01* (2006.01)
*A61F 2/24* (2006.01)
(Continued)

(52) U.S. Cl.
CPC .......... *A61F 2/2427* (2013.01); *A61B 17/068* (2013.01); *A61B 17/105* (2013.01);
(Continued)

(58) Field of Classification Search
CPC .......... A61M 25/0147; A61M 25/0108; A61M 25/0136; A61M 25/0105; A61M 25/0068;
(Continued)

(56) References Cited

U.S. PATENT DOCUMENTS 3,604,488 A    9/1971   Wishart et al.
3,656,185 A    4/1972   Carpentier
(Continued)

FOREIGN PATENT DOCUMENTS

EP    0611561 A1    8/1994
EP    1034753 A1    9/2000
(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Katherine M Rodjom
(74) *Attorney, Agent, or Firm* — Thomas C. Richardson

(57) ABSTRACT

An apparatus can include: (1) a steerable tube, having a proximal section, a distal section, and a central longitudinal axis, the tube defining a primary lumen and two secondary lumens; (2) two wires, each extending from the distal section proximally through a respective secondary lumen; (3) a handle, coupled to the proximal section, and including a steering knob that is coupled to the wires such that rotation of the knob adjusts a degree of tension in the wires; (4) a pull ring coupled to the distal section of the tube such that the pull ring circumscribes the longitudinal axis at the distal section of the tube, and defining two recesses, a distal end portion of each wire being disposed in a respective one of the recesses; and (5) at least one cap, bridging the recesses and the distal end portion of the wires. Other embodiments are also described.

27 Claims, 30 Drawing Sheets

(51) Int. Cl.
    *A61M 25/00*           (2006.01)
    *A61M 25/06*           (2006.01)
    *A61B 17/068*          (2006.01)
    *A61B 17/10*           (2006.01)
    *A61B 90/00*           (2016.01)
    *A61B 17/00*           (2006.01)
    *A61B 17/064*          (2006.01)
    *A61B 17/29*           (2006.01)

(52) U.S. Cl.
CPC .......... *A61F 2/2445* (2013.01); *A61F 2/2466* (2013.01); *A61M 25/0054* (2013.01); *A61M 25/0068* (2013.01); *A61M 25/01* (2013.01); *A61M 25/0105* (2013.01); *A61M 25/0108* (2013.01); *A61M 25/0136* (2013.01); *A61M 25/0147* (2013.01); *A61M 25/0662* (2013.01); A61B 2017/00305 (2013.01); A61B 2017/00314 (2013.01); A61B 2017/00323 (2013.01); A61B 2017/00367 (2013.01); A61B 2017/0649 (2013.01); A61B 2017/293 (2013.01); A61B 2090/0811 (2016.02); A61F 2210/0014 (2013.01); A61F 2250/001 (2013.01); A61F 2250/0098 (2013.01); A61M 25/005 (2013.01); A61M 25/0133 (2013.01); A61M 2025/0004 (2013.01); A61M 2025/0006 (2013.01); A61M 2025/015 (2013.01); A61M 2025/0681 (2013.01)

(58) Field of Classification Search
CPC .......... A61M 25/0662; A61M 25/0054; A61M 25/0133; A61M 25/055; A61M 2025/015; A61M 2025/0006
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |

(56) References Cited

U.S. PATENT DOCUMENTS

| | | |
|---|---|---|
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |

(56) References Cited

U.S. PATENT DOCUMENTS

| | | |
|---|---|---|
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkarn et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0133180 A1 | 9/2002 | Ryan et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |

(56) References Cited

U.S. PATENT DOCUMENTS

| | | |
|---|---|---|
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270679 A1* | 11/2007 | Nguyen ............ A61M 25/0043 600/373 |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |

(56) References Cited

U.S. PATENT DOCUMENTS

| | | |
|---|---|---|
| 2008/0091169 A1* | 4/2008 | Heideman .......... A61M 25/0012 604/527 |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0125861 A1 | 5/2008 | Webler et al. |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228265 A1 | 9/2008 | Spence et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168827 A1* | 7/2010 | Schultz .............. A61M 25/0136 607/116 |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |

(56) References Cited

U.S. PATENT DOCUMENTS

| | | |
|---|---|---|
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0245993 A1 | 8/2017 | Gross et al. |
| 2018/0049875 A1 | 2/2018 | Iflah et al. |

FOREIGN PATENT DOCUMENTS

| | | |
|---|---|---|
| EP | 2273928 A2 | 1/2011 |
| WO | 9205093 A1 | 4/1992 |
| WO | 9846149 A1 | 10/1998 |
| WO | 0009048 A1 | 2/2000 |
| WO | 02085250 A3 | 2/2003 |
| WO | 03047467 A1 | 6/2003 |
| WO | 2008014144 A3 | 6/2008 |
| WO | 2008031103 A3 | 10/2008 |
| WO | 2009130631 A2 | 10/2009 |
| WO | 2010000454 A1 | 1/2010 |
| WO | 2010065274 A1 | 6/2010 |
| WO | 2010150178 A2 | 12/2010 |
| WO | 2012106346 A1 | 8/2012 |
| WO | 2012176195 A3 | 3/2013 |
| WO | 2014064964 A1 | 5/2014 |
| WO | 2016087934 A1 | 6/2016 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al."Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral calve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

* cited by examiner

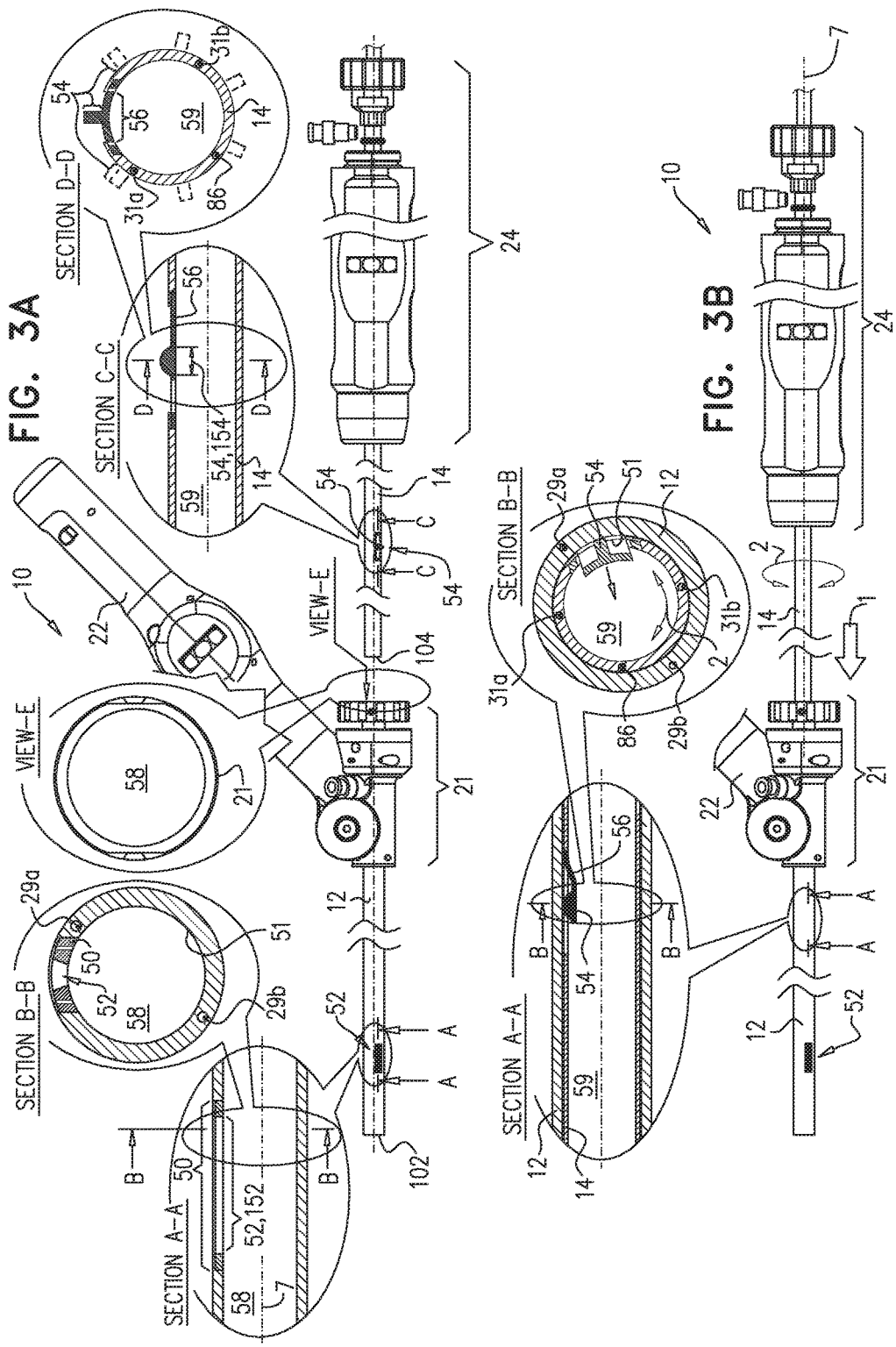

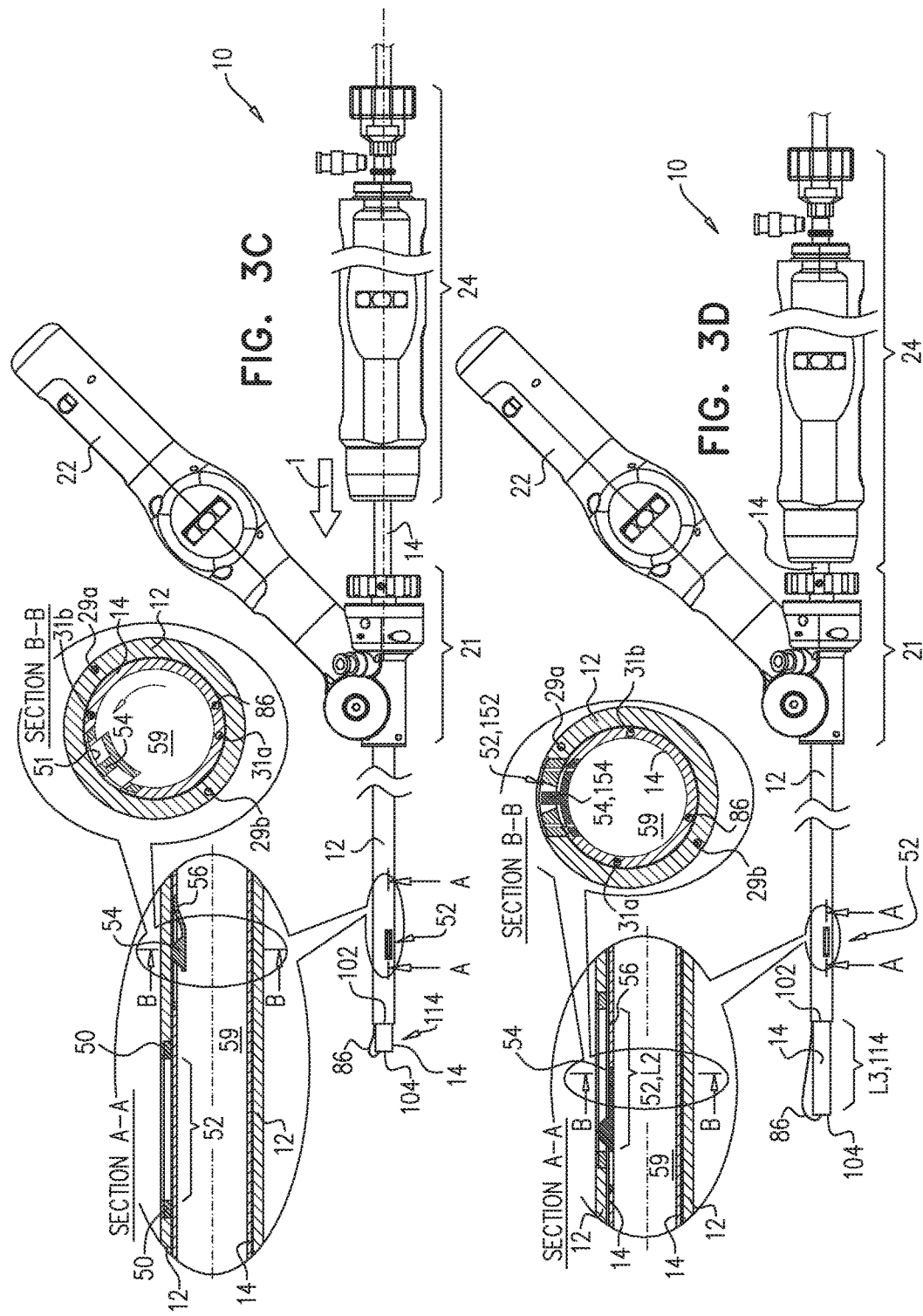

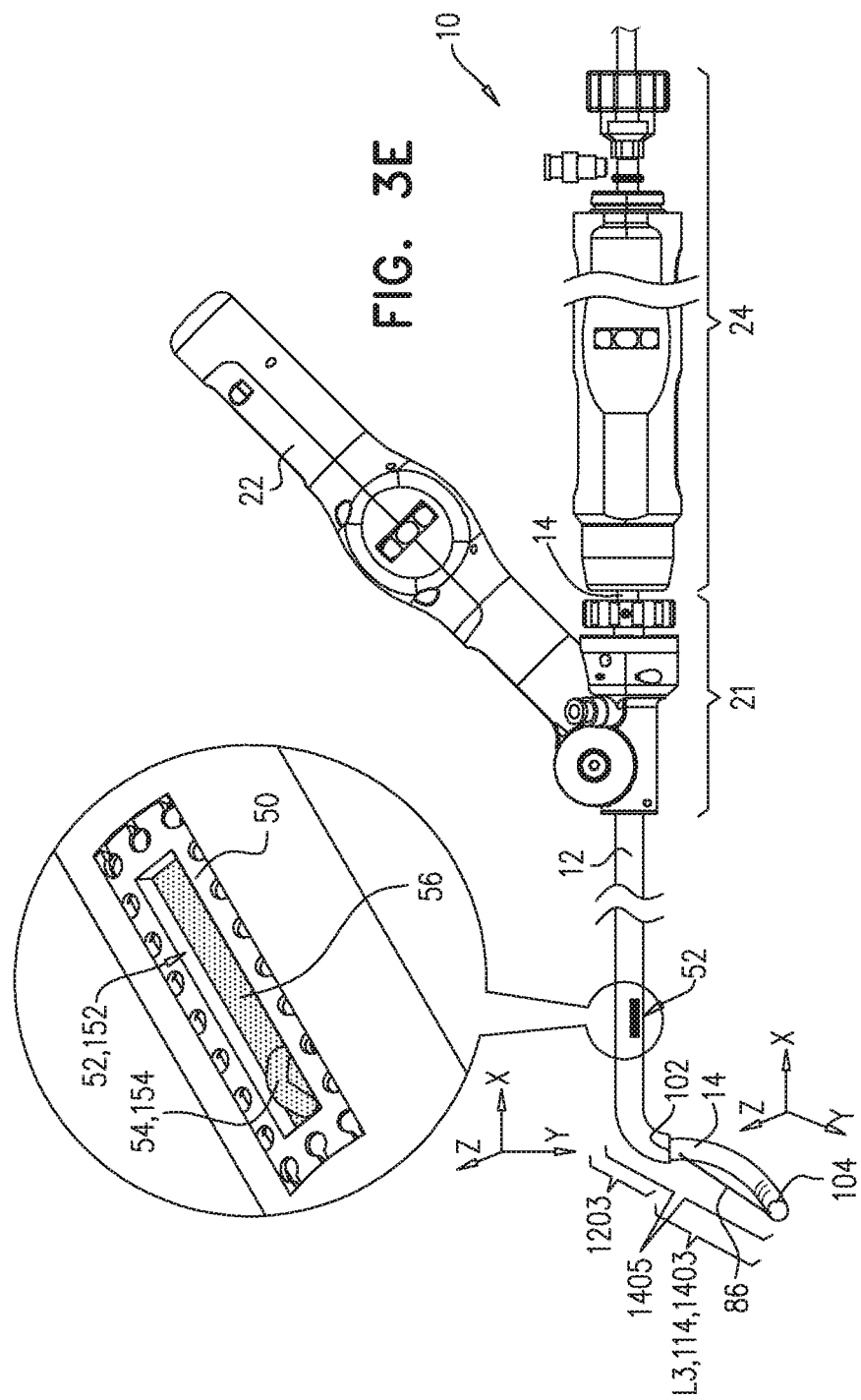

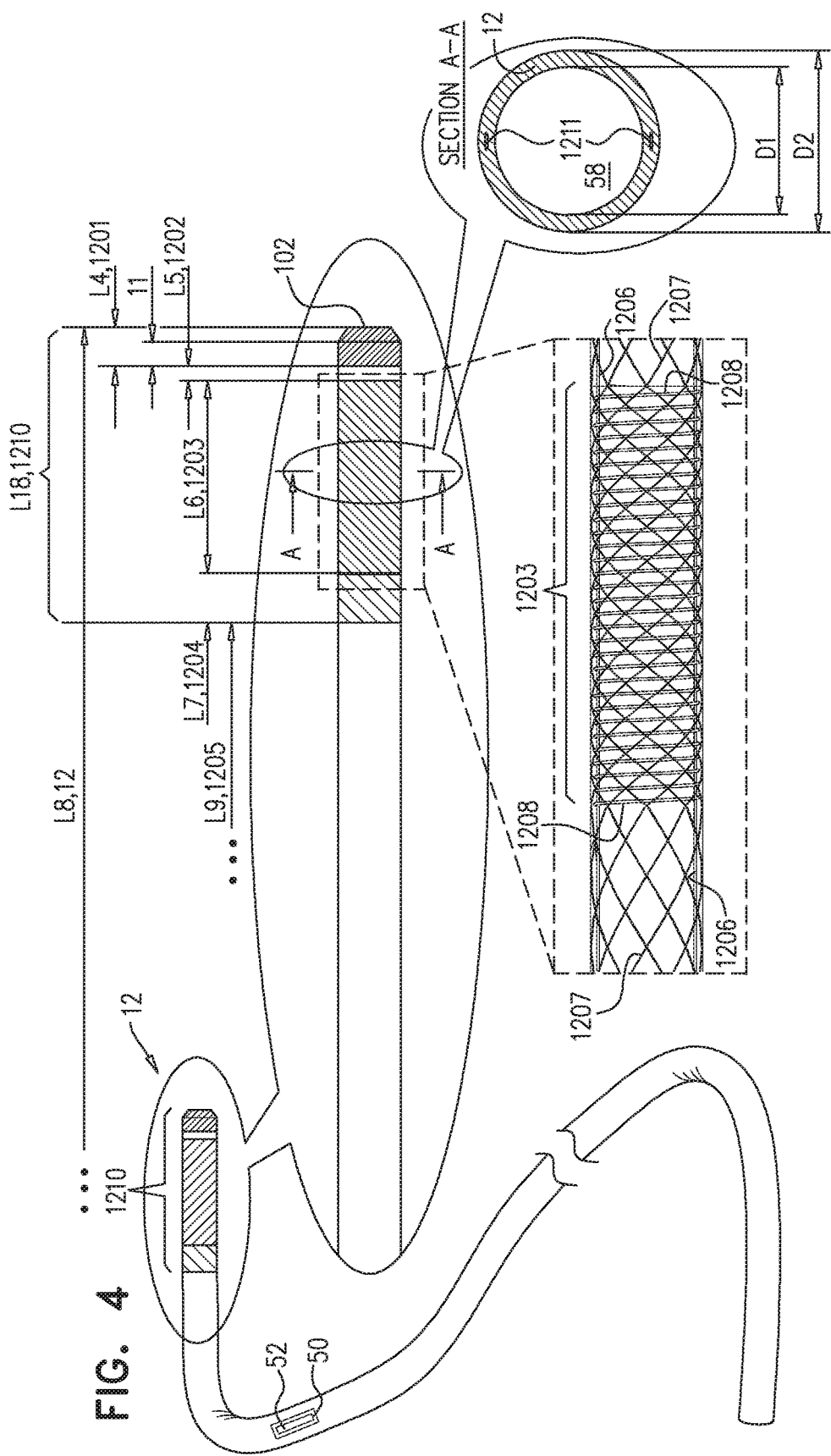

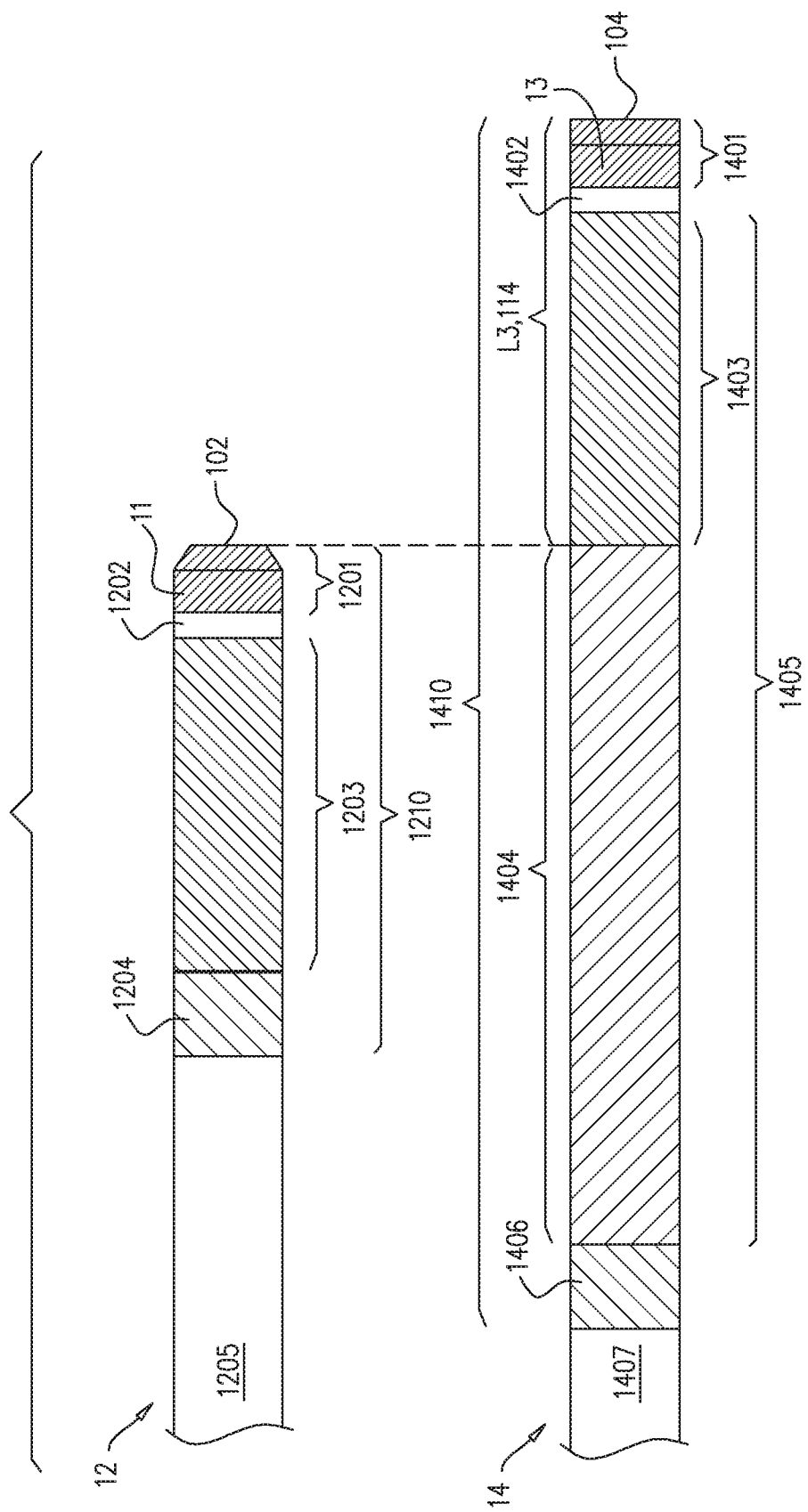

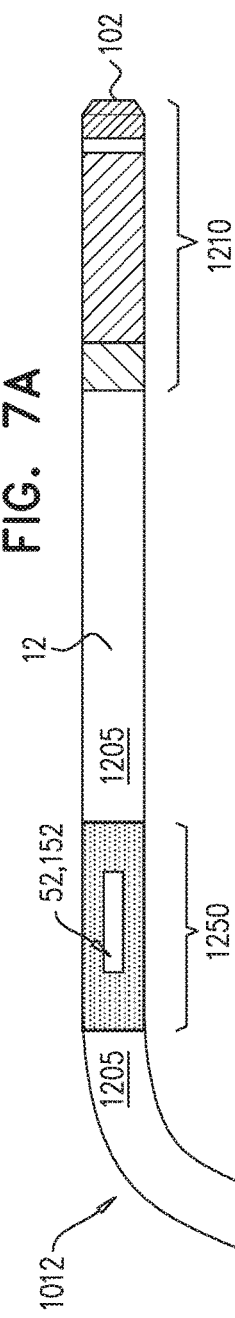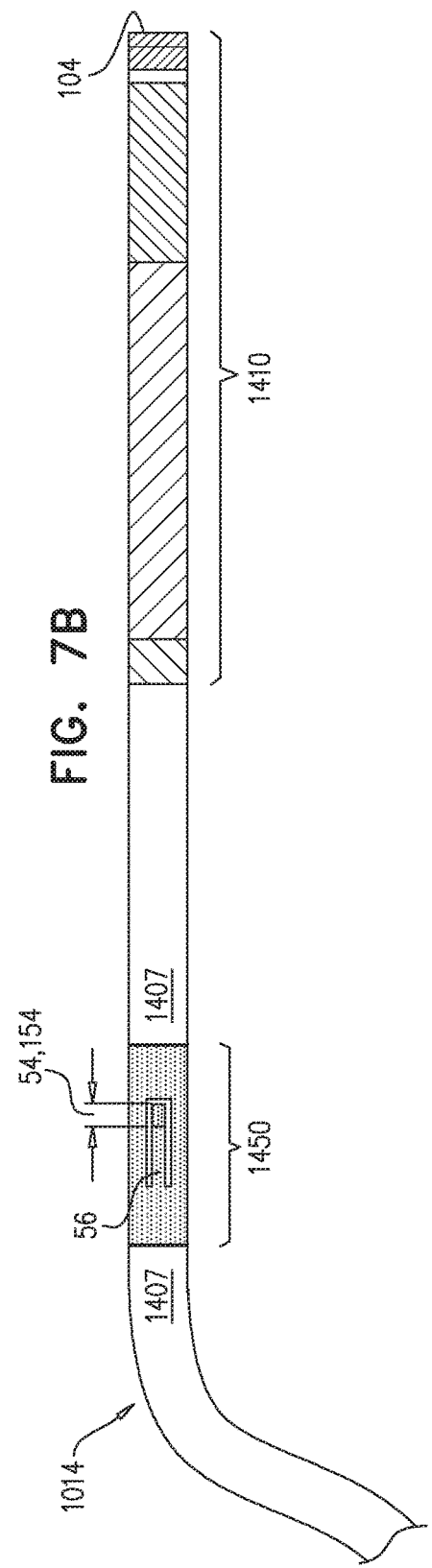

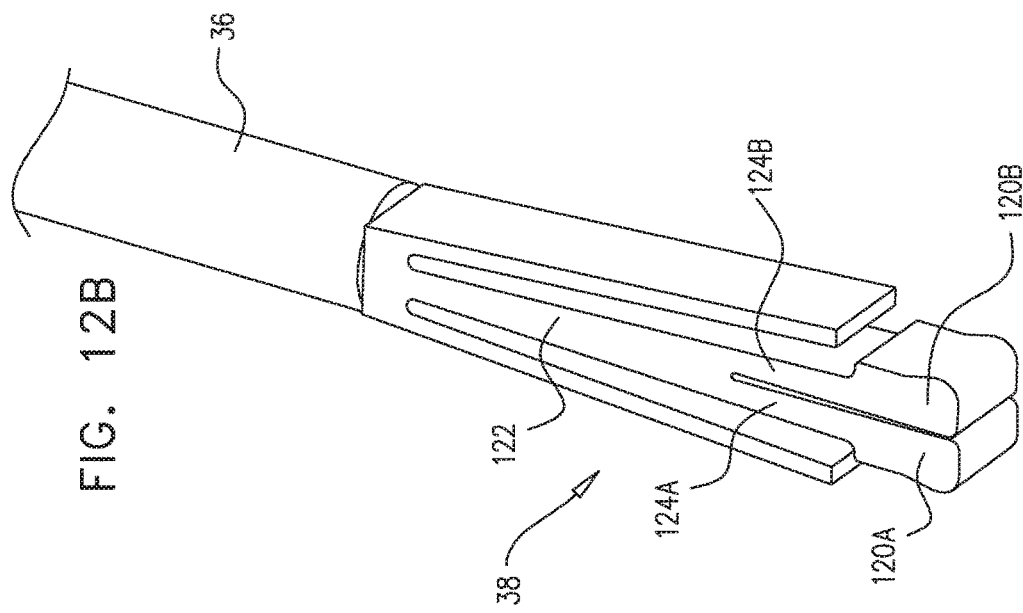
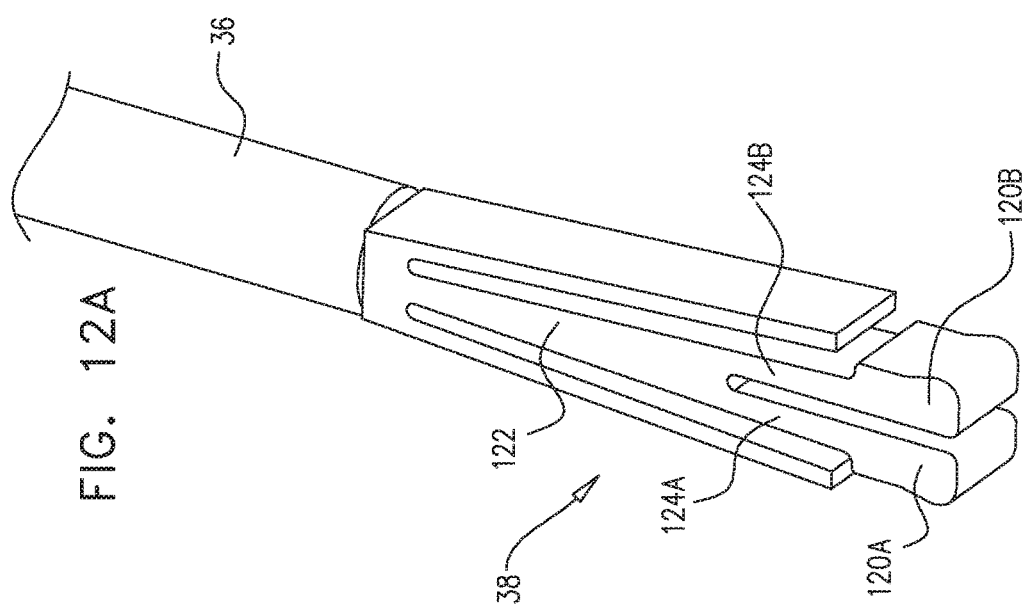

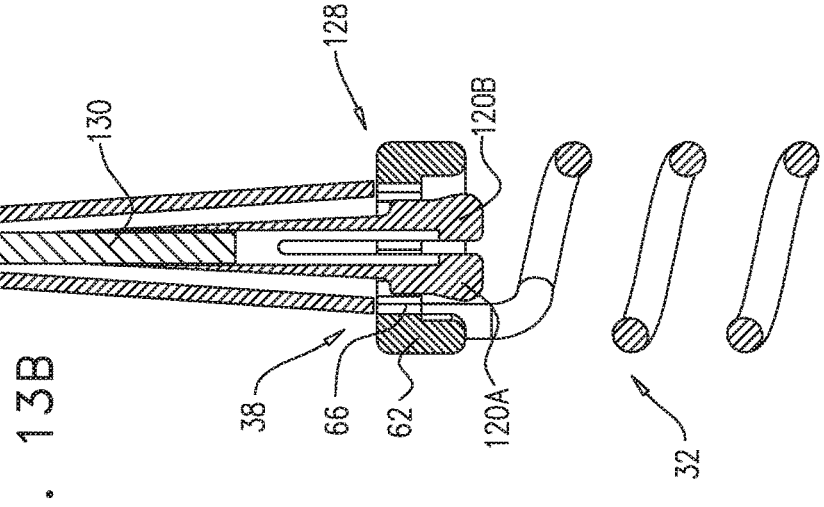
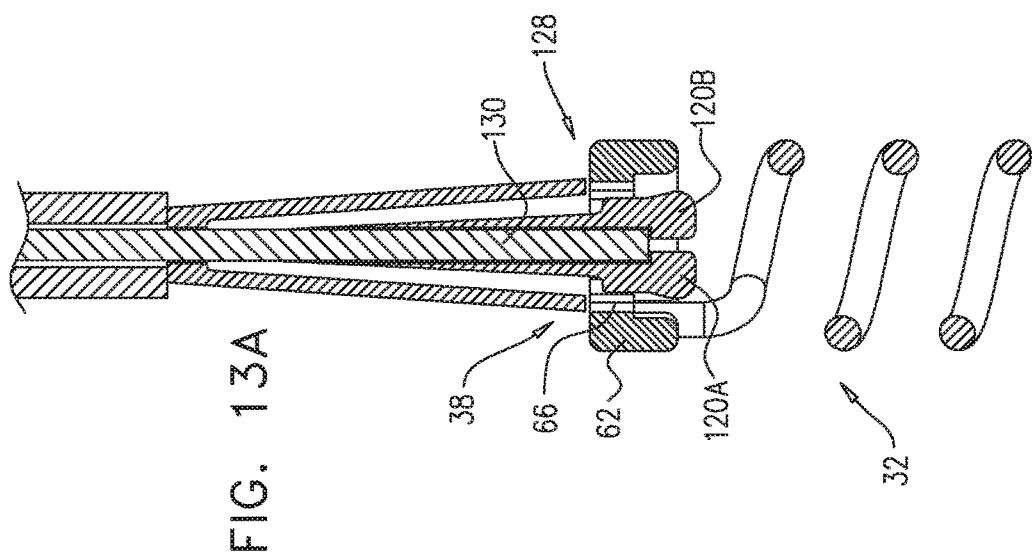

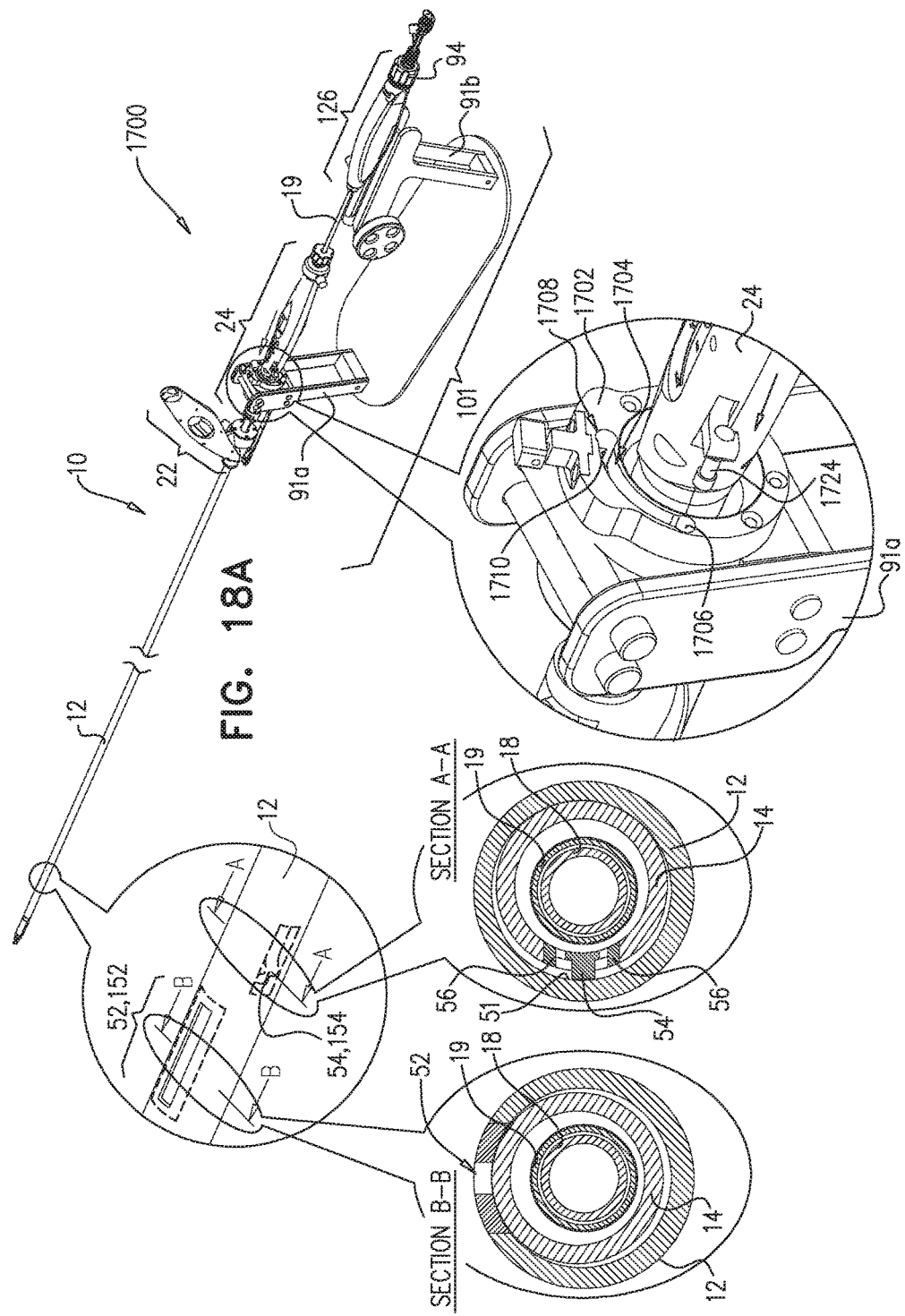

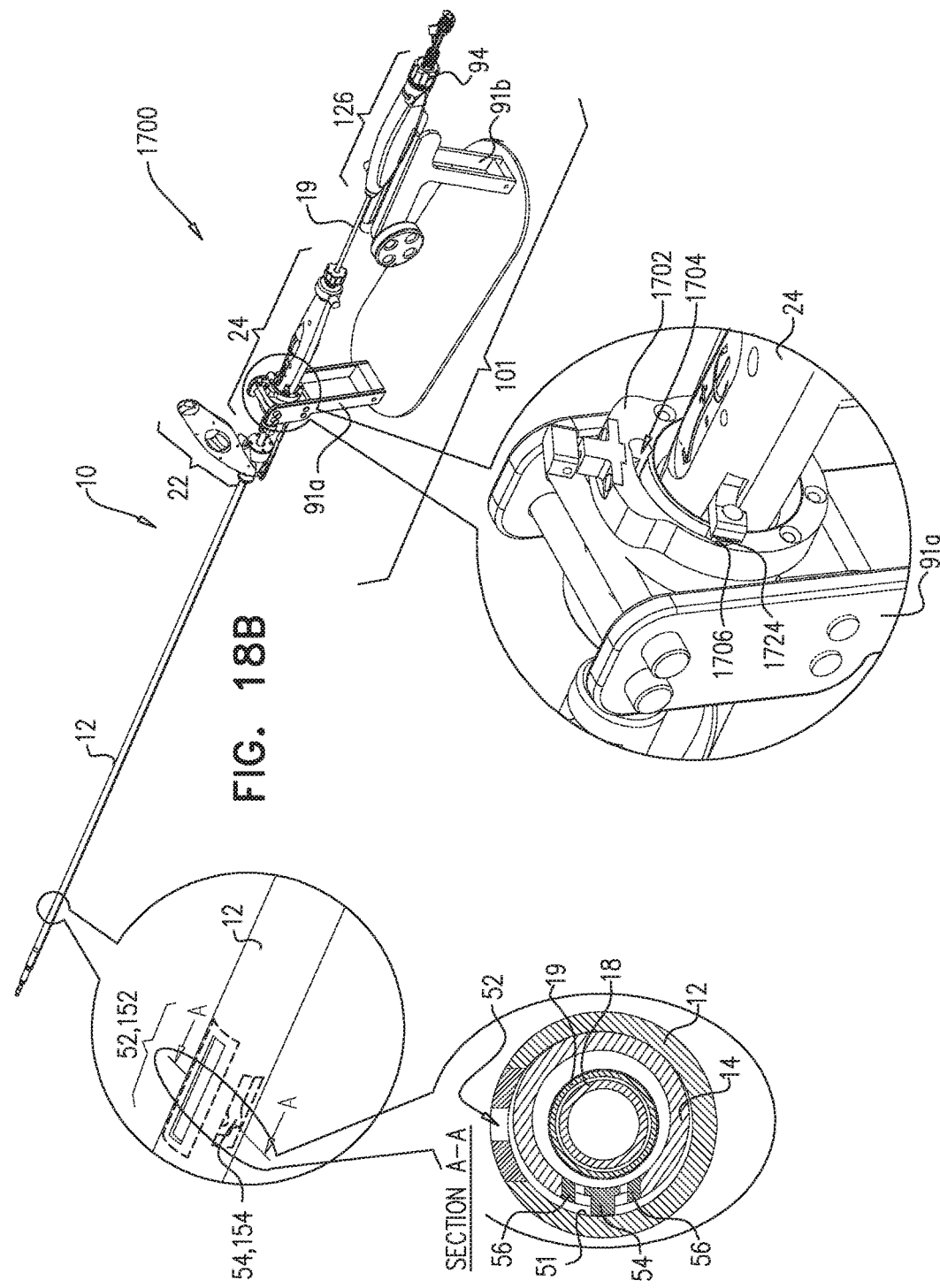

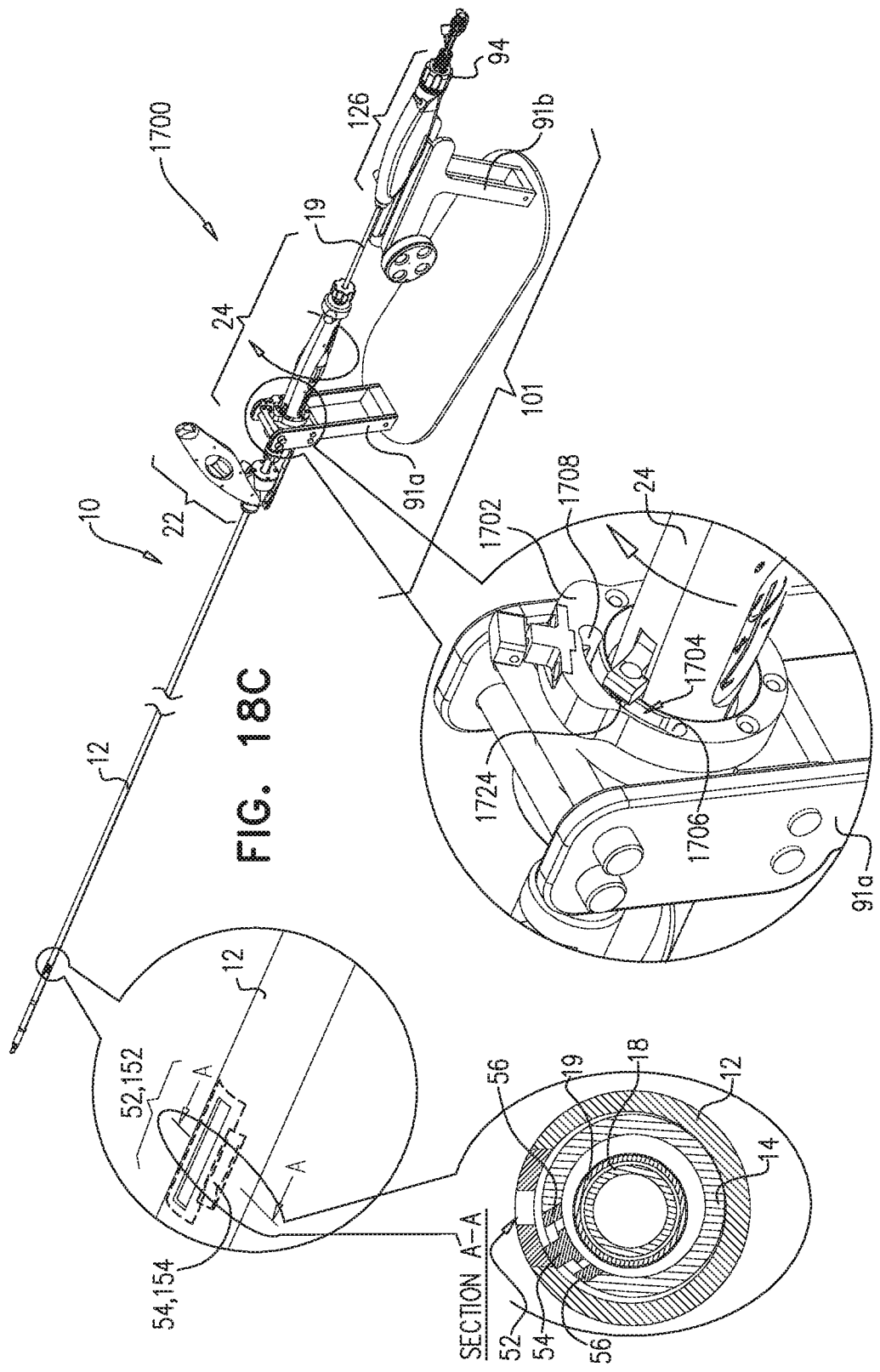

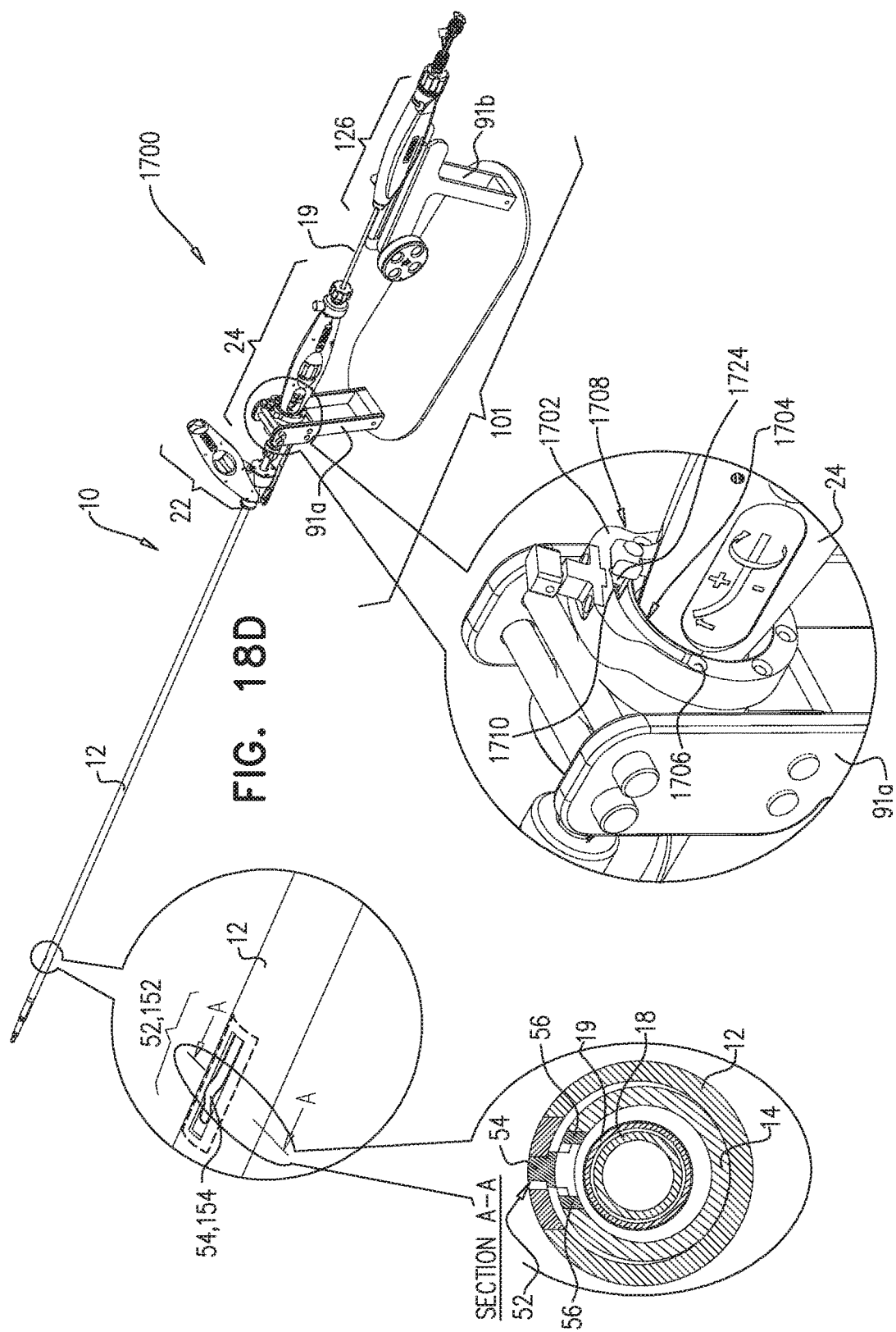

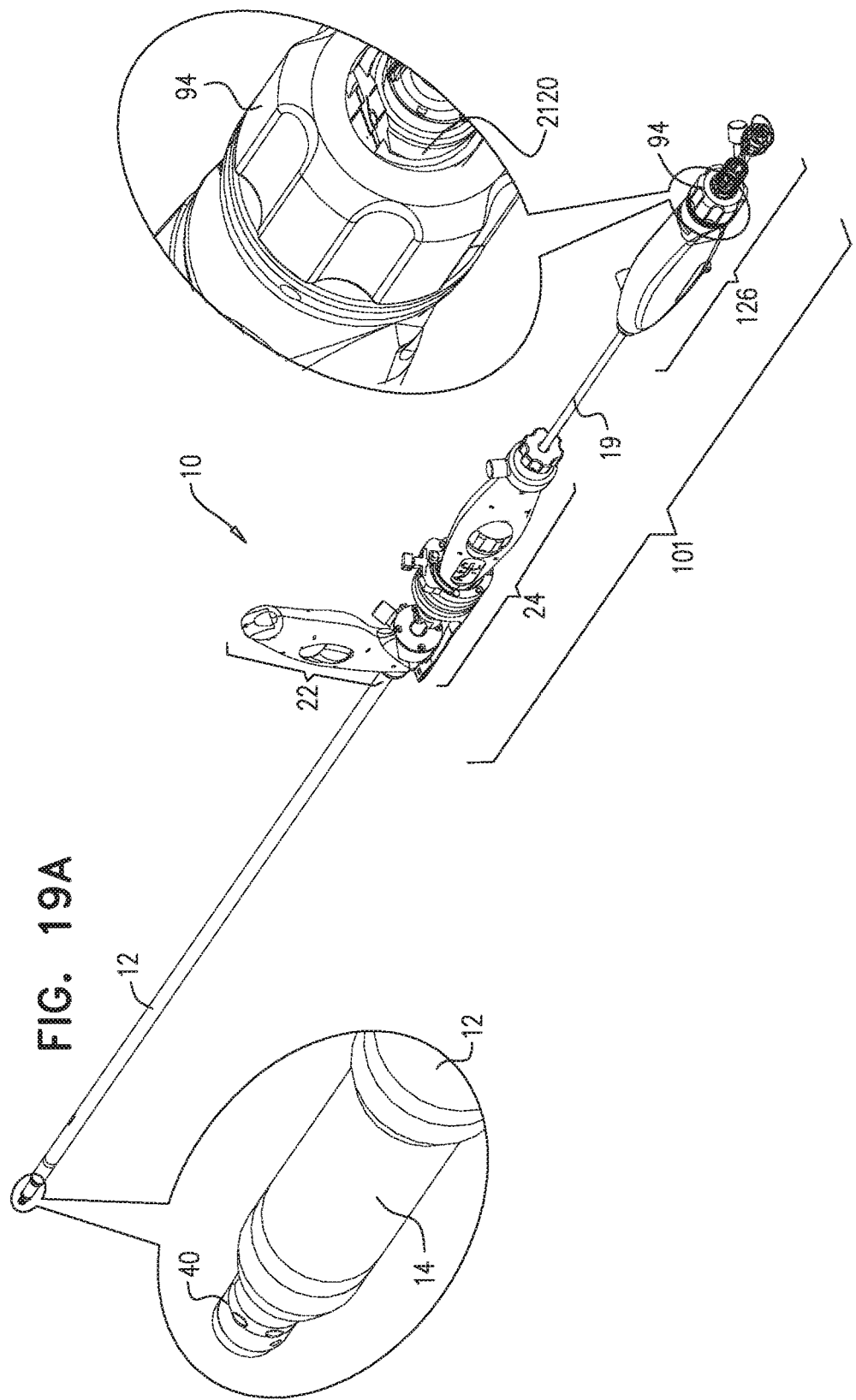

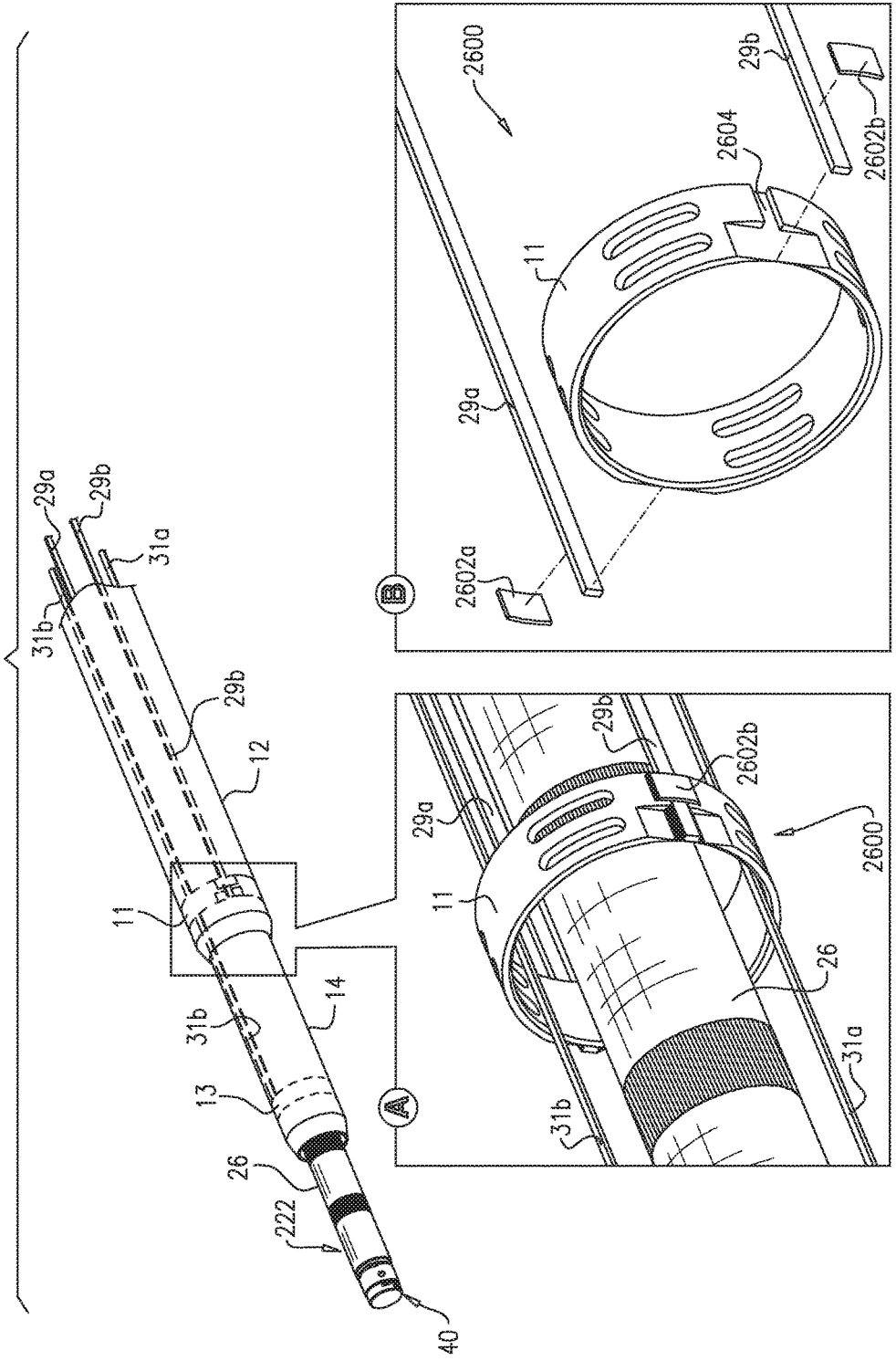

CONTROLLED STEERING FUNCTIONALITY FOR IMPLANT-DELIVERY TOOL

CROSS-REFERENCES TO RELATED APPLICATIONS

The present application is a Continuation of U.S. Ser. No. 14/357,040 to Sheps et al., entitled "Controlled steering functionality for implant-delivery tool," which published as US 2014/0309661 (now U.S. Pat. No. 9,724,192), which is the US National Phase of PCT application IL2012/050451 to Sheps et al, entitled "Controlled steering functionality for implant-delivery tool," filed Nov. 8, 2012, which published as WO 2013/069019, and which claims priority from U.S. Provisional Patent Application 61/557,082 to Sheps et al., entitled "Controlled steering functionality for implant-delivery tool," filed Nov. 8, 2011, which is incorporated by reference.

FIELD OF THE INVENTION

The present invention relates in general to valve repair. More specifically, the present invention relates to repair of a cardiac valve of a patient using a steerable delivery tool.

BACKGROUND

Steerable catheters are typically used to access a body cavity of a patient since these steerable catheters are able to navigate through vasculature of the patient. Additionally, pre-shaped sheaths are used to deliver an implant to the body cavity in a particular orientation.

SUMMARY OF THE INVENTION

In some applications of the present invention, a multi-component tubular system is provided for accessing a heart of a patient. The system comprises one or more steerable guiding catheters configured for directing the passage of devices therethrough into the heart. The multi-component tubular system is configured to deliver an implant in a desired orientation to an annulus of a cardiac valve of the patient and to facilitate anchoring of the implant to the annulus. For some applications of the present invention, the guiding system is advanced transluminally or transthoracically accessing an atrium of the heart. Typically, the system comprises two or more steerable catheters. A first catheter has a distal portion that is steerable to a first desired spatial orientation. A second catheter is disposed within the first catheter and has a distal portion that is steerable to a second desired spatial orientation. The system provides techniques and relative-spatial-orientation-controlling devices for controlling the orientation of the distal portion of the second catheter with respect to the first catheter without substantially distorting the first spatial orientation of the distal portion of the first catheter. For some applications, the relative-spatial-orientation-controlling device comprises a rotational locking mechanism provided by components of the catheter system.

For some applications, the first catheter is configured to provide a slit at the distal portion thereof (i.e., a first component of the rotational locking mechanism), and the second catheter is configured to provide a depressible pin (i.e., a second component of the rotational locking mechanism) at a distal portion thereof. The second catheter is configured for advancement through a lumen of the first catheter. During the advancement, the pin is depressed by an inner wall of the first catheter. The pin is configured to return to a resting state in which the pin is not depressed, when the pin is aligned with the slit of the first catheter. Since the first catheter provides the slit at a distal portion thereof, the second catheter may be introduced within the lumen of the first catheter in any suitable rotational orientation with respect to the first catheter.

The distal portion of the first catheter may be steered in a suitable direction following advancement of the first catheter through vasculature of the patient. Following the advancement of the first catheter and steering of the distal portion of the first catheter in any one or more suitable planes, the second catheter is advanced through the first catheter. The second catheter is advanced through the first catheter until at least a distal-most portion of the distal portion of the second catheter is exposed from within the lumen of the first catheter. Depending on the relative rotational orientation of the second catheter with respect to the first catheter, the physician may need to rotate the second catheter in order to engage the pin with the slit and lock the second catheter with respect to the first catheter. Such locking enables steering of the distal portion of the second in any one or more suitable planes with respect to the distal portion of the first catheter in a manner which substantially maintains the spatial orientation of the first catheter during the steering of the second catheter. Additionally, the first catheter may be further steered without substantially disrupting the spatial orientation of the distal portion of the second catheter.

There is therefore provided, in accordance with an application of the present invention, apparatus for percutaneous access to a body of a patient, including:
a first steerable tube, having a proximal end and a distal end, and shaped to define:
a first lumen between the proximal end and the distal end, and
a first coupling at a longitudinal site of the first steerable tube; and
a second steerable tube, shaped to define a second lumen and a second coupling, the second coupling being intracorporeally couplable to the first coupling,
the apparatus having:
an unlocked state in which at least the second coupling is disposed within the first lumen, and the second steerable tube is rotatable within the first lumen, and
a locked state in which the second coupling is coupled to the first coupling, the coupling of the second coupling to the first coupling inhibiting rotation of the second steerable tube within the first lumen, and
the apparatus being configured such that:
the second coupling is advanceable through the first lumen until at least the longitudinal site,
the apparatus remains in the unlocked state when the second coupling is disposed within the first lumen, proximal to the longitudinal site, and
when the second coupling becomes disposed at the longitudinal site in a given rotational orientation of the second steerable tube within the first lumen, the apparatus moves into the locked state by the second coupling automatically coupling to the first coupling.

In an application, when the apparatus is in the locked state, the second steerable tube has a distal steering portion that is exposed from the distal end of the first steerable tube. In an application, the second coupling is advanceable through the first lumen until at least the longitudinal site, in any rotational orientation of the second steerable tube with respect to the first steerable tube.

In an application:

the first coupling has a longitudinal length that is less than 30% of a longitudinal length of the first steerable tube, the second coupling has a longitudinal length that is less than 30% of a longitudinal length of the second steerable tube, and the second steerable tube is couplable to the first steerable tube by the second coupling being couplable to the first coupling.

In an application, the first coupling has a longitudinal length that is less than 2% of the longitudinal length of the first steerable tube, and the second coupling has a longitudinal length that is less than 2% of the longitudinal length of the second steerable tube.

In an application:

the first steerable tube includes a respective first pull ring and a respective first pair of pull wires, and the second steerable tube includes a respective and a respective second pair of pull wires, each of the pull rings is disposed at a respective distal steerable portion of the respective steerable tube, and each pull wire of each pair of pull wires is coupled to the respective pull ring thereof, and extends within a wall of the respective steerable tube, proximally from the respective pull ring.

In an application, the apparatus is configured such that, when the apparatus is in the locked state thereof, a plane on which the first pair of pull wires lies is generally orthogonal to a plane on which the second pair of pull wires lies.

In an application:

each pull ring is shaped to define at least two recesses, a distal portion of each pull wire being disposed in a respective recess, the disposition in the respective recess facilitating the coupling of the pull wire to the pull ring.

In an application, the apparatus further includes a plurality of caps, and at least one of the caps is coupled to each pull ring such that the at least one cap bridges at least one of the recesses and the distal end portion of at least one pull wire, the coupling of the at least one cap to the pull ring facilitating the coupling of the pull wire to the pull ring.

In an application, the distal steerable portion of at least one of the steerable tubes selected from the group consisting of the first steerable tube and the second steerable tube includes a multiple-durometer section, the multiple-durometer section including:

a distal pull-ring section, the first pull-ring being coupled to the distal pull-ring section;

a bending section, proximal to the distal pull-ring section, and more flexible than the distal pull-ring section; and a transition section, between the distal pull-ring section and the bending section, and being more flexible than the distal pull-ring section and less flexible than the bending section.

In an application:

the selected steerable tube includes a uniform-durometer section, proximal to the multiple-durometer section, the transition section includes a first transition section, and the selected steerable tube includes a second transition section between the bending section and the uniform-durometer section, the second transition section being more flexible than the uniform-durometer section and less flexible than the bending section.

In an application, the apparatus further includes an extracorporeal locking system, including a protrusion and a housing, and:

the housing is shaped to define a groove, and the protrusion is configured to be coupled to the housing by being disposed in the groove, and the apparatus is configured such that the coupling of the protrusion to the housing facilitates the inhibition of the rotation of the second steerable tube within the first lumen.

In an application:

the apparatus further includes a first handle, coupled to the first steerable tube, and a second handle, coupled to the second steerable tube, one of the handles selected from the group consisting of the first handle and the second handle, includes the housing, one of the handles selected from the group consisting of the first handle and the second handle, includes the housing, and the protrusion is configured to be coupled to the housing by the first handle being coupled to the second handle.

In an application, the apparatus further includes a stand that includes a track, and the first handle and the second handles are independently slidably coupled to the track.

In an application, the apparatus further includes at least one extracorporeal indicator, coupled to the second steerable tube, configured to move correspondingly with the second coupling, and to provide an indication of an intracorporeal position of the second coupling with respect to the first steerable tube.

In an application, the second coupling is configured to revolve around a longitudinal axis of the second steerable tube in response to rotation of the second steerable tube, and the extracorporeal indicator is configured to revolve around the axis correspondingly with the second coupling.

In an application, the second coupling is configured to move longitudinally in response to longitudinal movement of the second steerable tube, and the extracorporeal indicator is configured to move longitudinally correspondingly with the second coupling.

In an application, the apparatus further includes an extracorporeal locking system, including the extracorporeal indicator and a housing, the housing being coupled to the first steerable tube, and the apparatus being configured such that a juxtaposition of the housing and the extracorporeal indicator corresponds to a juxtaposition of the first coupling and the second coupling.

In an application:

the extracorporeal indicator includes a protrusion, the housing is shaped to define a groove configured to receive the protrusion, and the protrusion is configured to be coupled to the housing by being disposed in the groove, the coupling of the protrusion to the housing:

facilitating the inhibition of the rotation of the second steerable tube within the first lumen, and providing an extracorporeal indication that the second coupling is coupled to the first coupling.

In an application, at least one of the couplings selected from the group consisting of the first coupling and the second coupling, is shaped to define a receptacle, and at least one of the couplings selected from the group consisting of the first coupling and the second coupling is shaped to define a protrusion configured to be disposed within the receptacle, the protrusion being configured:

in the unlocked state of the apparatus, to be depressed by a proximity of an inner wall of the first steerable tube to an outer wall of the second steerable tube, and to automatically move into the receptacle when the second coupling is disposed within the first lumen at the longitudinal site and the second steerable tube is in the given rotational orientation.

In an application, the receptacle has a length of between 5 and 15 mm.

In an application, the protrusion has a length of between 2 and 3 mm.

In an application, when the apparatus is in the locked state, the second coupling is axially slidable with respect to the first coupling by greater than 5 mm and less than 15 mm.

In an application, when the apparatus is in the locked state, the second steerable tube has an exposed distal steering portion that is exposed from the distal end of the first steerable tube, and the slidability of the second coupling with respect to the first coupling facilitates the exposed distal steering portion having a variable length, the variable length having a smallest length of 25 mm and a greatest length of 35 mm.

There is further provided, in accordance with an application of the present invention, apparatus for percutaneous access to an anatomical site of a body of a patient, including:
a first catheter, having an outer diameter of no more than 9 mm, and being shaped to define a first lumen therethrough, a distal end of the first catheter:
being transluminally advanceable to a vicinity of the anatomical site, and
being bendable in a first plane;
a second catheter, shaped to define a second lumen therethrough, a distal end of the second catheter:
being advanceable through the first lumen and out of a distal end of the first lumen,
when disposed outside the distal end of the first lumen, being bendable in a second plane;
an implant, having an inner wall, and being disposable within at least the distal end of the second catheter;
a reference-force tube:
being shaped to define a third lumen,
being configured to move the implant through the distal end of the second lumen, and
having a distal end that is advanceable through at least the distal end of the second lumen;
a channel:
disposed at least in part within the third lumen,
shaped to define a fourth lumen, the fourth lumen being configured to provide fluid communication therethrough between a proximal end of the channel and the inner wall of the implant, and
having a distal end that is disposed within the implant, the distal end being configured to be slidable out of the implant;
at least one anchor, configured to be delivered to the inner wall of the implant via the fourth lumen; and
a deployment manipulator:
including an anchor driver, and a deployment element, disposed at a distal end of the anchor driver, and configured to be reversibly couplable to the anchor, and
being configured to advance the anchor through the fourth lumen and through the inner wall of the implant.

In an application, the fourth lumen has a transverse cross-sectional diameter of at least 2.5 mm.

In an application, the implant is shaped to define a lumen, the reference-force tube is shaped to define a lumen, and the lumen of the reference-force tube is in fluid communication with the lumen of the implant.

In an application, the anchor driver is shaped to define a fifth lumen, and the apparatus further includes a rod, configured to be slidable within the fifth lumen so as to facilitate the reversible coupling of the deployment element to the anchor.

In an application, the deployment element, the anchor, and the rod are configured such that, when the deployment element is coupled to the anchor, proximal movement of the rod facilitates decoupling of the deployment element from the anchor.

In an application, the distal end of the second catheter is advanceable through the first lumen in any rotational orientation with respect to the first catheter, and the second catheter is couplable to the first catheter such that rotation of the second catheter within the first lumen is inhibited.

In an application, the second plane is generally orthogonal to the first plane, and the second catheter is couplable to the first catheter such that the distal end of the second catheter is bendable in the second plane that is generally orthogonal to the first plane.

In an application, the apparatus is configured such that the coupling of the second catheter to the first catheter reduces an effect of bending of the distal end of the second catheter on the rotational orientation of the distal end of the second catheter with respect to the first catheter.

In an application:
the first catheter is shaped to define a first coupling, having a longitudinal length that is less than 30% of a longitudinal length of the first catheter,
the second catheter is shaped to define a second coupling, having a longitudinal length that is less than 30% of a longitudinal length of the second catheter, and
the second catheter is couplable to the first catheter by the second coupling being couplable to the first coupling.

In an application, the first coupling has a longitudinal length that is less than 2% of the longitudinal length of the first catheter, and the second coupling has a longitudinal length that is less than 2% of the longitudinal length of the second catheter.

In an application:
the first catheter includes a lateral wall that defines the first lumen,
the second catheter includes a lateral wall that defines the second lumen, and
any lateral opening in the lateral wall of a catheter selected from the group consisting of the first catheter and the second catheter, is an opening defined by at least one of the couplings selected from the group consisting of the first coupling and the second coupling.

In an application:
the first catheter includes a lateral wall that defines the first lumen,
the second catheter includes a lateral wall that defines the second lumen, and
any protrusion from the lateral wall of a catheter selected from the group consisting of the first catheter and the second catheter, is a protrusion defined by at least one of the couplings selected from the group consisting of the first coupling and the second coupling.

In an application, the apparatus further includes at least one extracorporeal indicator, coupled to the second catheter, configured to move correspondingly with the second coupling, and to provide an indication of an intracorporeal position of the second coupling with respect to the first catheter.

In an application, the second coupling is configured to revolve around a longitudinal axis of the second catheter in response to rotation of the second catheter, and the extracorporeal indicator is configured to revolve around the axis correspondingly with the second coupling.

In an application, the second coupling is configured to move longitudinally in response to longitudinal movement of the second catheter, and the extracorporeal indicator is configured to move longitudinally correspondingly with the second coupling.

In an application, the apparatus further includes an extracorporeal locking system, including the extracorporeal indicator and a housing, the housing being coupled to the first catheter, and the apparatus being configured such that a juxtaposition of the housing and the extracorporeal indicator corresponds to a juxtaposition of the first coupling and the second coupling.

In an application:
the extracorporeal indicator includes a protrusion,
the housing is shaped to define a groove configured to receive the protrusion, and
the protrusion is configured to be coupled to the housing by being disposed in the groove, the coupling of the protrusion to the housing:
    facilitating the inhibition of the rotation of the second catheter within the first lumen, and
    providing an extracorporeal indication that the second coupling is coupled to the first coupling.

In an application, the apparatus further includes at least one extracorporeal indicator, configured to move correspondingly with the implant, and to provide an indication of an intracorporeal position of the implant with respect to the second catheter.

In an application, the extracorporeal indicator is coupled to the reference-force tube, and is configured provide an indication of an intracorporeal state of deployment of the implant from the distal end of the second catheter.

In an application, the apparatus further includes an extracorporeal locking system, including a protrusion and a housing, and:
the housing is shaped to define a groove, and
the protrusion is configured to be coupled to the housing by being disposed in the groove, and
the apparatus is configured such that the coupling of the protrusion to the housing inhibits rotation of the second catheter within the first lumen.

In an application:
the apparatus further includes a first handle, coupled to the first catheter, and a second handle, coupled to the second catheter,
one of the handles selected from the group consisting of the first handle and the second handle, includes the housing,
one of the handles selected from the group consisting of the first handle and the second handle, includes the housing, and
the protrusion is configured to be coupled to the housing by the first handle being coupled to the second handle.

In an application, the apparatus further includes a stand that includes a track, and the first handle and the second handles are independently slidably coupled to the track.

In an application:
the first catheter includes a respective first pull ring and a respective first pair of pull wires, and the second catheter includes a respective and a respective second pair of pull wires,
each of the pull rings is disposed at a respective distal steerable portion of the respective catheter, and
each pull wire of each pair of pull wires is coupled to the respective pull ring thereof, and extends within a wall of the respective catheter, proximally from the respective pull ring.

In an application:
each pull ring is shaped to define at least two recesses, a distal portion of each pull wire being disposed in a respective recess, the disposition in the respective recess facilitating the coupling of the pull wire to the pull ring.

In an application, the apparatus further includes a plurality of caps, and at least one of the caps is coupled to each pull ring such that the at least one cap bridges at least one of the recesses and the distal end portion of at least one pull wire, the coupling of the at least one cap to the pull ring facilitating the coupling of the pull wire to the pull ring.

In an application, the distal steerable portion of at least one of the catheters selected from the group consisting of the first catheter and the second catheter, includes a multiple-durometer section, the multiple-durometer section including:
    a distal pull-ring section, the first pull-ring being coupled to the distal pull-ring section;
    a bending section, proximal to the distal pull-ring section, and more flexible than the distal pull-ring section; and
    a transition section, between the distal pull-ring section and the bending section, and being more flexible than the distal pull-ring section and less flexible than the bending section.

In an application:
the selected catheter includes a uniform-durometer section, proximal to the multiple-durometer section,
the transition section includes a first transition section, and
the selected catheter includes a second transition section between the bending section and the uniform-durometer section, the second transition section being more flexible than the uniform-durometer section and less flexible than the bending section.

There is further provided, in accordance with an application of the present invention, a method for use with a native atrioventricular valve of a heart of a subject, the method including:
transluminally advancing a first steerable tube toward the heart, the first steerable tube being shaped to define a first lumen and a first coupling;
bending at least a distal portion of the first steerable tube;
advancing a second steerable tube through the first lumen, while the second steerable tube is rotatable within the first lumen, such that a distal portion of the second steerable tube emerges from a distal end of the first steerable tube, the second steerable tube being shaped to define a second lumen and a second coupling;
after at least part of the distal portion of the second steerable tube is exposed from the distal end of the first steerable tube and is disposed within a chamber of the heart, aligning the second coupling with the first coupling by moving the second steerable tube with respect to the first steerable tube, such that the second coupling automatically couples to the first coupling; and
while the second coupling is coupled to the first coupling, bending the distal portion of the second steerable tube toward the native atrioventricular valve of the subject.

There is further provided, in accordance with an application of the present invention, apparatus configured for providing access through a subject's skin, including:
a first steerable tube having a first lumen, the first steerable tube shaped to define a first coupling; and
a second steerable tube having a second lumen, the second steerable tube being configured to be concentrically disposed within the first lumen of the first steerable tube, the second steerable tube being shaped to define a second coupling; and:

at least one coupling selected from the group consisting of: the first coupling and the second coupling, has a longitudinal length that is less than 20 cm, the first and second couplings are selectively engageable so as to facilitate:
introducing of the second steerable tube within the first lumen in any suitable rotational orientation of the second steerable tube with respect to the first steerable tube, and
axial sliding of the second steerable tube with respect to the first steerable tube, and the first and second couplings are configured, when engaged and during steering of a distal steerable portion of the second steerable tube, to (1) generally maintain a spatial orientation of a distal steerable portion of the first steerable tube, and (2) minimize an effect of the spatial orientation of the distal steerable portion of the first steerable tube on the steering of the distal steerable portion of the second steerable tube.

In an application, the first coupling has a proximal-most end that is disposed up to 100 mm from a distal end of the first steerable tube.

In an application, the second coupling has a proximal-most end that is disposed up to 120 mm from a distal end of the second steerable tube.

In an application:
at least one of the couplings selected from the group consisting of the first coupling and the second coupling is shaped to define a receptacle,
at least one of the couplings selected from the group consisting of the first coupling and the second coupling is shaped to define a protrusion configured to be disposed within the receptacle.

In an application, the receptacle has a length of between 5 and 15 mm.

In an application, the protrusion has a length of between 2 and 3 mm.

In an application, the protrusion is (1) depressible when surrounded by an inner wall of the first steerable tube that defines the first lumen, and (2) protrudable into the receptacle when aligned with the receptacle.

In an application, when the first and second couplings are engaged, the second steerable tube is axially slidable with respect to the first steerable tube by greater than 5 mm and less than 15 mm.

In an application, when the first and second couplings are engaged, the second steerable tube has an exposed-distal-steering portion that is exposed from the first steerable tube, and the second steerable tube is axially slidable with respect to the first steerable tube such that a length of the exposed-distal-steering portion is adjustable to be between 25 and 35 mm.

The present invention will be more fully understood from the following detailed description of embodiments thereof, taken together with the drawings, in which:

BRIEF DESCRIPTION OF THE DRAWINGS

FIGS. 3A-E are schematic illustrations of cross-sectional images of components of the catheter system of FIGS. 1-2, in accordance with some applications of the present invention;

FIGS. 4-6 are schematic illustrations of components of the catheter system of FIGS. 1-2, in accordance with some applications of the present invention;

FIGS. 7A-B are schematic illustrations of components of the catheter system of FIGS. 1-2, in accordance with some other applications of the present invention;

FIGS. 12A-B are schematic illustrations of a rotating deployment element of an anchor deployment system in radially-expanded and radially-compressed states, respectively, in accordance with some applications of the present invention;

FIGS. 13A-B are schematic illustrations of the rotating deployment element of FIGS. 12A-B engaging a tool-engaging head of a tissue anchor, with the element in locked and unlocked states, respectively, in accordance with some applications of the present invention;

FIGS. 18A-D are schematic illustrations of an indicator and locking system comprising a protrusion and a housing, or cradle, shaped to define a groove, in accordance with some applications of the present invention;

FIGS. 19A-B are schematic illustrations of a sleeve-deployment indicator, in accordance with some applications of the present invention; and FIG. 20 is a schematic illustration of a system for coupling a pull ring of a catheter to pull wires, in accordance with some applications of the invention.

DETAILED DESCRIPTION OF EMBODIMENTS

Figure 1:
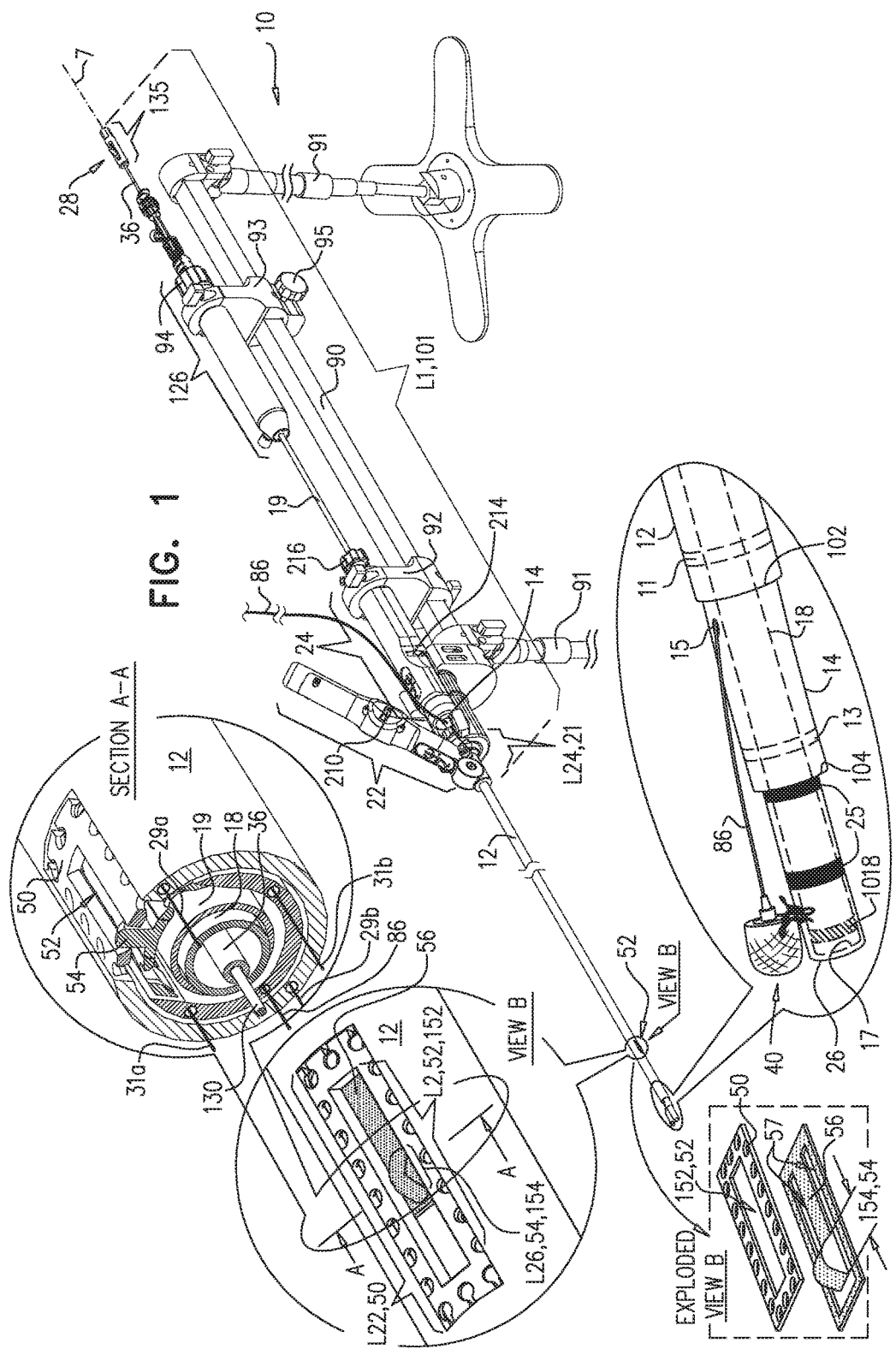
FIGS. 1-2 are schematic illustrations of multi-component tubular system for delivering and anchoring an implant and for controlling a relative spatial orientation of components of the catheter system, in accordance with some applications of the present invention.
Figure 2:
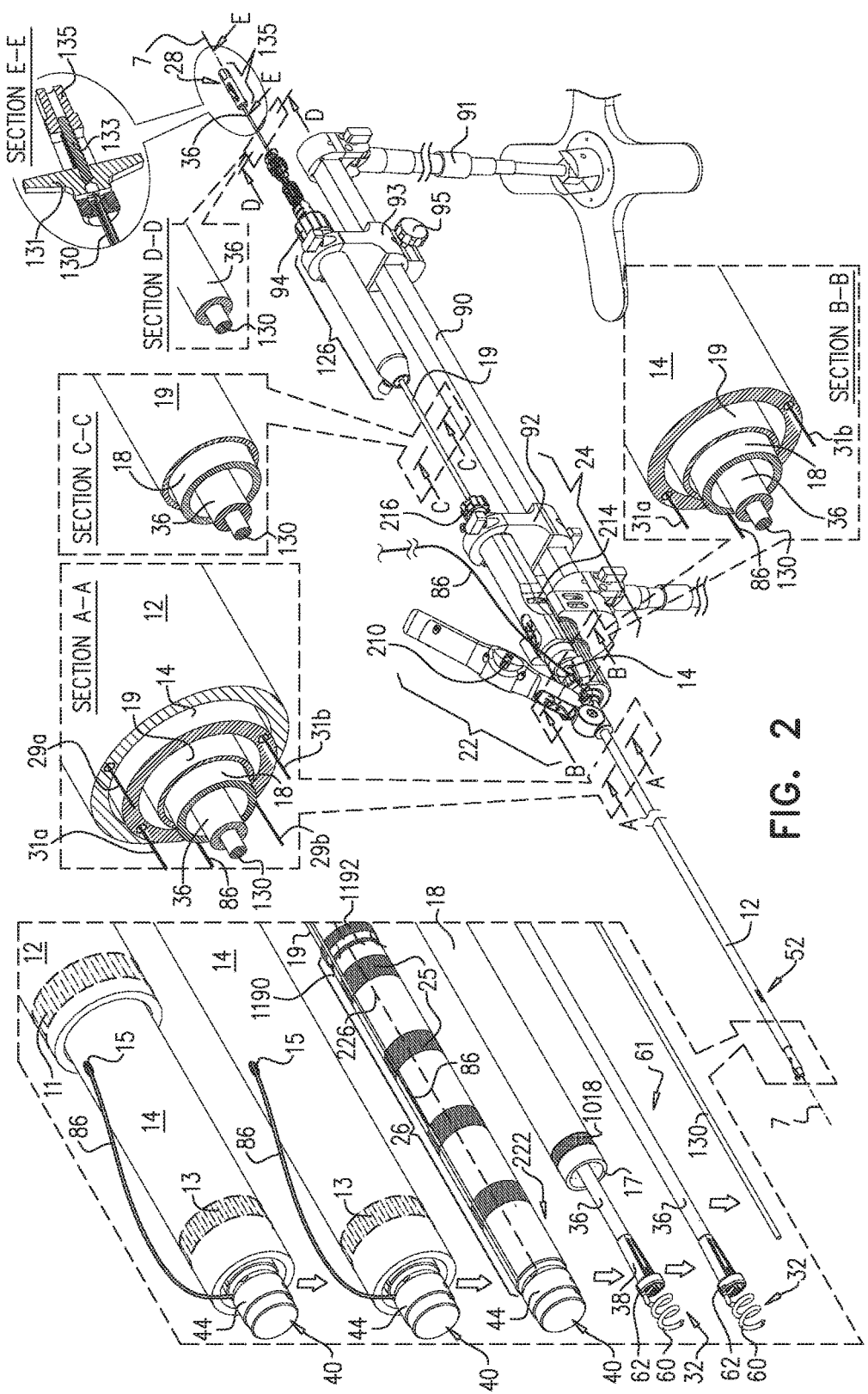

Reference is now made to FIGS. 1-2, which are schematic illustrations of a multi-component tubular system 10 providing one or more rotationally-controlled steering catheters configured for delivering an implant to a heart of a patient, in accordance with some applications of the present invention. System 10 provides an implant-delivery tool. Typically, system 10 comprises a first, outer catheter 12 comprising a sheath (i.e., a lateral wall that defines a lumen) configured for advancement through vasculature of a patient. For some applications of the present invention, outer catheter 12 comprises a sheath configured for advancement through a femoral artery toward an interatrial septum of a heart of a patient. A distal steerable end portion of outer catheter 12 is configured to pass through the septum and be oriented in a desired spatial orientation. System 10 comprises a second catheter, or guide catheter 14, comprising a steerable distal end portion. Catheter 14 comprises a sheath (i.e., a lateral wall that defines a lumen), and is configured for advancement through the lumen of outer catheter 12. Outer catheter 12 provides a first coupling 152 (e.g., a receptacle, such as an opening, such as a slit 52) at a distal portion of the lateral wall thereof (e.g., a portion of catheter 12 that is proximal to the steerable distal end portion). Guide catheter 14 comprises a second coupling 154 (e.g., a protrusion, such as a depressible engager 54) that is coupled to a displaceable tab 56 coupled to a base. As is described herein, depressible engager 54 (or the second coupling 154) is configured so as to protrude within slit 52 (or the first coupling 152). Thus, slit 52 defines a second-coupling-receiving element.

First coupling 152 of catheter 12 defines a longer coupling, the second coupling 154 of catheter 14 defines a shorter coupling. The first and second couplings 152 and 154 of outer catheter 12 and guide catheter 14, respectively, enable axial advancement and rotational motion of guide catheter 14 through the lumen of outer catheter 12 until engager 54 of catheter 14 is aligned with and engages slit 52 of catheter 12, as will be described hereinbelow. As shown in cross-section A-A of FIG. 1, guide catheter 14 is configured to be concentrically disposed within a lumen of outer catheter 12. It is to be noted that the scope of the present invention includes catheter 12 providing the shorter coupling, and catheter 14 providing the longer coupling. For example, catheter 14 may be shaped so as to provide slit 52, and catheter 12 may comprise engager 54, which is configured to engage slit 52 of catheter 14.

As shown in the exploded view of view B, first coupling 152 is shaped to define slit 52. For some applications, slit 52 is provided by a metal frame 50, as shown. Metal frame 50 has a length L22 of between 7 and 15 mm, e.g., 13 mm. For such applications, a slit is created in material of catheter 12 (e.g., by creating a slit in the polymer material of catheter 12 during manufacturing of catheter 12), and frame 50 is coupled to catheter 12. Second coupling 154 comprises an engager 54 which comprises a protrusion disposed at a distal portion of displaceable tab 56 of a base of engager 54. The base of engager 54 is shaped to define slits 57 which form tab 56. Engager 54 is depressible when a force is applied thereto, and tab 56 facilitates movement of engager 54 in response to and in the absence of force applied to engager 54. For some applications, during manufacture of catheter 14, catheter 14 is manipulated in order to couple thereto engager 54 and tabs 56, e.g., engager 54 and tabs 56 are embedded within the polymer of catheter 14.

It is to be noted that although slit 52 and depressible engager 54 are shown on outer catheter 12 and guide catheter 14, respectively, at distal portions of catheters 12 and 14, slit 52 and engager 54 may be provided along any suitable portion of catheters 12 and 14, respectively (e.g., respective proximal portions of catheters 12 and 14).

FIG. 2 shows the concentric relationship between components of tubular system 10 (in an exploded view on the left side of FIG. 2). As described hereinabove, a distal end portion of outer catheter 12 is steerable. The distal end portion of outer catheter 12 comprises a pull ring 11 that is coupled to two or more pull wires 29*a* and 29*b*, that are disposed within respective secondary lumens within a wall of catheter 12 (as shown in section A-A). As shown in the exploded view, guide catheter 14 is configured to be concentrically disposed within the lumen of catheter 12. As described hereinabove, the distal end portion of guide catheter 14 is steerable. The distal end portion of catheter 14 comprises a pull ring 13 that is coupled to two or more pull wires 31*a* and 31*b*, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the patient. As shown, the implant comprises an annuloplasty ring structure 222 comprising a flexible sleeve 26 (shown in the exploded view of FIG. 2). Sleeve 26 typically comprises a braided fabric mesh, e.g., comprising DACRON™. Sleeve 26 is typically configured to be placed only partially around a cardiac valve annulus (i.e., to assume a C-shape), and, once anchored in place, to be contracted so as to circumferentially tighten the valve annulus. Alternatively, the ring structure is configured to be placed entirely around the valve annulus. In order to tighten the annulus, annuloplasty ring structure 222 comprises a flexible elongated contracting member 226 that extends along sleeve 26. Elongated contracting member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 226 comprises a braided polyester suture (e.g., Ticron). For some applications, contracting member 226 is coated with polytetrafluoroethylene (PTFE). For some applications, contracting member 226 comprises a plurality of wires that are intertwined to form a rope structure.

For applications in which system 10 is used to deliver an implant to the mitral valve of the patient, typically, outer catheter 12 is configured for initial advancement through vasculature of the patient until a distal end 102 of catheter 12 is positioned in the left atrium. The distal steerable end portion of catheter 12 is then steered such that distal end 102 of catheter 12 is positioned in a desired spatial orientation within the left atrium. The steering procedure is typically performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of the steerable distal end portion of catheter 14 is exposed from distal end 102 of catheter 12 and is thus free for steering toward the annulus of the mitral valve, as is described hereinbelow.

Annuloplasty ring structure 222 further comprises an adjusting mechanism 40, which facilitates contracting and expanding of annuloplasty ring structure 222 so as to facilitate adjusting of a perimeter of the annulus and leaflets of the cardiac valve. Adjusting mechanism 40 is described in more detail hereinbelow. Adjusting mechanism 40 comprises a rotatable structure (e.g., a spool, as described hereinbelow) that is disposed within a housing 44. As shown in the enlarged image of FIG. 1, adjusting mechanism 40 is surrounded by a braided mesh and is coupled (e.g., by being sutured or otherwise coupled) to the braided mesh of sleeve 26. For some applications, adjusting mechanism 40 is coupled to an outer, lateral surface of sleeve 26. During delivery of sleeve 26 to the annulus of the cardiac valve, sleeve 26 is disposed within a lumen of catheter 14 and sleeve 26 and mechanism 40 are aligned longitudinally with a longitudinal lumen of catheter 14. Such coupling of mechanism 40 to sleeve 26 allows mechanism 40 to transition from a state in which it is in line with the longitudinal axis of catheter 14 (FIG. 2) to a state in which it is disposed alongside sleeve 26 (FIG. 1). The positioning of adjusting mechanism 40 alongside a portion of sleeve 26 exposes a driving interface of the rotational structure to be accessed by a rotational tool that is guided toward adjusting mechanism 40 via guide member 86.

A flexible, longitudinal guide member 86 (e.g., a wire) is coupled to a portion of adjusting mechanism 40 (e.g., a portion of the rotatable structure, as described hereinbelow). Guide member 86 is configured to facilitate guiding of a rotational tool via guide member 86 and toward the rotatable structure of adjusting mechanism 40. Typically, the rotational tool is configured to engage the rotatable structure of adjusting mechanism 40 following implantation of sleeve 26 along the annulus of the cardiac valve. Guide member 86 passes from adjusting mechanism 40, alongside a portion of the distal end portion of guide catheter 14, and into a secondary lumen in the wall of guide catheter 14, through an opening 15 in guide catheter 14. Guide member 86 passes through the secondary lumen of guide catheter 14 (as shown in sections A-A and B-B in FIG. 2) and has a proximal end that is accessible from outside the body of the patient. The secondary lumen in the wall of guide catheter 14 facilitates passage of guide member 86 through system 10 without interfering with the other concentrically-disposed elongate tubular members that pass concentrically through the lumen of guide catheter 14.

In addition, system 10 comprises a plurality of anchors 32, typically between about 5 and about 20 anchors, such as about 10 or about 16 anchors. Each anchor 32 comprises a tissue coupling element 60 (e.g., a helical tissue coupling element), and a tool-engaging head 62, fixed to one end of the tissue coupling element. Only one anchor 32 is shown in FIG. 2 as being reversibly coupled to a deployment element 38 of a rotating anchor driver 36 of an anchor deployment manipulator 61. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Typically, but not necessarily, anchors 32 comprise a biocompatible material such as stainless steel 316 LVM. For some applications, anchors 32 comprise nitinol. For some applications, anchors 32 are coated with a non-conductive material.

Deployment manipulator 61 comprises anchor driver 36 and deployment element 38.

As shown in the exploded view of FIG. 2, sleeve 26 is disposed within a lumen of guide catheter 14. A force is applied to a proximal end of sleeve 26 is by a distal end of a reference-force tube 19. As shown, an implant-decoupling channel 18 is advanceable within a lumen of reference-force tube 19 and through a lumen of sleeve 26. Typically, decoupling channel 18 fits snugly within sleeve 26. As shown in the enlarged image of FIG. 1, a distal end 17 of implant-decoupling channel 18 is disposed in contact with an inner wall of sleeve 26 at a distal end thereof. Additionally, a distal end portion of channel 18 comprises a radiopaque marker 1018. As shown, tube 19 and sleeve 26 are longitudinally and coaxially disposed with respect to each other.

Typically, manipulator 61 advances within channel 18. For some applications, system 10 comprises a plurality of anchor drivers 36 of manipulator 61, each driver 36 being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. Subsequently, a new driver 36 coupled to another anchor 32 is then advanced within channel 18.

As will be described hereinbelow, a first anchor 32 is configured to be deployed through the wall of the sleeve into cardiac tissue, when sleeve 26 is positioned along the annulus of the valve. Following the deployment of the first anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Each anchor 32 is coupled to deployment element 38 of anchor driver 36. Anchor driver 36 comprises an elongate tube having at least a flexible distal end portion. The elongate tube of driver 36 extends within a lumen of channel 18, through system 10 toward a proximal end of a proximal handle portion 101 of system 10. Typically, the lumen of channel 18 has a transverse cross-sectional diameter of at least 2 mm, such as at least 2.5 mm. The tube of anchor driver 36 provides a lumen for slidable advancement therethrough of an elongate rod 130. Rod 130 facilitates the locking and unlocking of anchor 32 to deployment element 38, as is described hereinbelow. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the physician releases anchor 32 from deployment element 38 when finger-engager 131 is pulled proximally, thereby pulling rod 130 proximally.

Proximal handle portion 101 is supported by a stand having support legs 91 and a handle-sliding track 90. Handle portion 101 comprises an outer-catheter handle 22, a guide-catheter handle 24, an implant-manipulating handle 126, and anchor-release mechanism 28. Handle 22 is coupled to a proximal end of outer catheter 12. Handle 24 is coupled to a proximal portion of guide catheter 14. Handle 126 is coupled to a proximal portion of reference-force tube 19. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 2.

The stand supporting proximal handle portion 101 may be moved distally and proximally to control a position of the entire multi-component system 10, particularly so as to adjust a distance of distal end 102 of catheter 12 from the interatrial septum. Handle 22 comprises a steering knob 210 that is coupled to steering wires 29a and 29b disposed within respective secondary lumens in the wall of outer catheter 12. Rotation of knob 210 adjusts a degree of tension of wires 29a and 29b which, in turn, apply a force to pull ring 11 at the distal end portion of outer catheter 12. Such force steers the distal end portion of catheter 12 within the atrium of the heart of the patient in a manner in which the distal end portion of catheter 12 is steered in a first plane that is typically parallel with the plane of the annulus of the valve (e.g., in a direction from the interatrial septum toward surrounding walls of the atrium). For some applications of the present invention, the distal end portion of catheter 12 may be pre-shaped so as to point downward toward the valve. For other applications, the distal end portion of catheter 12 may be pulled to assume an orientation in which the distal end portion points downward toward the valve. For yet other applications of the present invention, the distal end portion of catheter 12 is not made to point downward toward the valve.

Handle 24 is coupled to track 90 via a first mount 92. Mount 92 is slidable proximally and distally along track 90 in order to control an axial position of guide catheter 14 with respect to outer catheter 12. Mount 92 is slidable via a control knob 216. For example, control knob 216 of mount 92 controls the proximal and distal axial movement of the distal steerable portion of guide catheter 14 with respect to distal end 102 of outer catheter 12. Handle 24 comprises a steering knob 214 that is coupled to steering wires 31a and 31b disposed within respective secondary lumens in the wall of guide catheter 14. Rotation of knob 214 adjusts a degree of tension of wires 31a and 31b which, in turn, apply a force to pull ring 13 at the distal end portion of guide catheter 14. Such force steers the distal end portion of catheter 14 in a second plane within the atrium of the heart of the patient, typically downward and toward the annulus of the cardiac valve. Typically, as described hereinbelow, the second plane in which the distal end portion of catheter 14 is steered is substantially perpendicular to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of the annulus (e.g., from the posterior section of the valve to the anterior section of the valve, and vice versa, e.g., via the steering of the distal end portion of catheter 12).

For some applications, handle 22 may be tilted by the operating physician, in order to further adjust a position of the distal end of catheter 12.

As described herein, first and second couplings 152 and 154 of outer catheter 12 and guide catheter 14, respectively (e.g., slit 52 and engager 54, respectively), provide a controlled steerable system in which, during the steering and bending of the distal end portion of guide catheter 14, the distal end portion of outer catheter 12 is maintained in its steered configuration, or in its spatial orientation, without substantially affecting the steering or the bending of the distal end portion of guide catheter 14. Thus, first and second couplings 152 and 154, respectively, minimize the effect of the distal end portion of outer catheter 12 on the steering and bending of catheter 14. That is, first and second couplings 152 and 154 of outer catheter 12 and guide catheter 14, respectively, collectively define a relative-spatial-orientation-controlling device which rotationally locks the relative spatial orientation of the steerable distal end portion and the bending section of outer catheter 12 with respect to the steerable distal end portion and the bending section of guide catheter 14.

Guide member 86 exits from the lumen in the wall of guide catheter 14 at a portion of handle portion 101 that is between handles 22 and 24.

Handle 126 is coupled to track 90 via a second mount 93. Mount 93 is slidable proximally and distally along track 90, in order to control an axial position of reference-force tube 19 and at least a proximal portion of sleeve 26 with respect to guide catheter 14. Mount 93 is slidable via a control knob 95. For example, control knob 95 of mount 93 controls the proximal and distal axial movement of the tube 19 and at least the proximal portion of sleeve 26 with respect to distal end 104 of guide catheter 14. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 is pulled proximally, while (2) reference-force tube 19 is maintained in place. A proximal end of channel 18 is coupled to a knob 94 which adjusts an axial position of channel 18 proximally and distally with respect to reference-force tube 19 and sleeve 26.

Handle portion 101 (comprising handles 22, 24, and 126 and anchor-release mechanism 28) has a length L1 of between 65 and 85 cm, e.g., 76 cm. Typically, as shown, a majority of the body portion of outer-catheter handle 22 is disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion 21 which is longitudinally disposed in-line along axis 7 and coaxially with respect to handles 24 and 126 and release mechanism 28. Tubular portion 21 is shaped to define a lumen for inserting guide catheter 14 therethrough and subsequently into the lumen of outer catheter 12 (as is described hereinbelow with reference to FIG. 3A). Tubular portion 21 has a length L24 of between 7 and 11 cm, e.g., 7 cm. Such spatial orientation of the majority of handle 22 at an angle with respect to axis 7 reduces an overall functional length of handle portion 101.

Reference is now made to FIGS. 3A-E, which are schematic illustrations of the functional relationship between first and second couplings 152 and 154, respectively, and respective degrees of rotational freedom of guide catheter 14 with respect to outer catheter 12, in accordance with some applications of the present invention. It is to be noted that FIGS. 3A-E show a functional relationship between catheters 12 and 14, and, for clarity of illustration, does not show the concentric components disposed within a longitudinal lumen 59 of catheter 14 (i.e., reference-force tube 19, channel 18, anchor driver 36, and rod 130, as shown in FIGS. 1 and 2). FIG. 3A shows catheters 12 and 14 in a state prior to advancing catheter 14 through a lumen 58 of catheter 12. Sections A-A and B-B of FIG. 3A show slit 52, or first coupling 152, empty. Section C-C shows a portion of catheter 14 which provides engager 54, or second coupling 154. As described hereinabove with reference to FIG. 1, engager 54 is coupled to a depressible tab 56 which facilitates depressible movement of engager 54 when a force is applied thereto (e.g., at a later stage by an inner wall 51 of catheter 12 that surrounds lumen 58 when catheter 14 is advanced through lumen 58, as is described hereinbelow). As shown in section C-C of FIG. 3A, in the absence of a pushing force, tab 56 is disposed in parallel with longitudinal axis 7, and engager 54 is in a resting state thereof in which engager 54 is not in a depressed state and protrudes from an external surface of catheter 14.

As shown in sections A-A and B-B of FIGS. 3A-B, first coupling 152 is provided in a manner in which lumen 58 of catheter 12 is free from any protrusions. Additionally, inner wall 51 of catheter 12 is not shaped to define any interrupted portions, such as recessed portions, along a proximal portion of catheter 12 and extending toward distal end 102 of catheter 12, except for slit 52 at a distal portion thereof. Once catheter 12 is advanced through the vasculature of the patient, distal end 104 of catheter 14 is configured to enter a lumen provided by tubular portion 21 of handle 22, and subsequently, catheter 14 passes through lumen 58 of catheter 12. View E is a view of lumen 58 of catheter 12 from a proximal portion of tubular portion 21 of handle 22. Since lumen 58 is free from any protrusions or recessed portions, as described hereinabove, and since engager 54 is depressible by tab 56, catheter 14 is configured to enter lumen 58 of catheter 12 in any rotational configuration thereof. Catheter 14 is shown in section D-D in a manner in which engager is oriented at 12 o'clock, by way of illustration and not limitation. Catheter 14 may enter lumen 58 of catheter 12 in any rotational configuration thereof, therefore engager 54 is shown in phantom in a plurality of orientations in section D-D, since catheter 14 may enter lumen 58 of catheter 12 in a rotational orientation in which engager 54 may be oriented in any given orientation with respect to inner wall 51 of catheter 12. Similarly, until couplings 152 and 154 are engaged (i.e., coupled to each other), catheter 14 may be freely rotated within catheter 12.

During the insertion of distal end 104 and the distal portion of catheter 14, the physician pushes down on engager 54 such that engager 54 fits within the lumen of catheter 12. In response to the pushing force on engager 54, tab 56 is pushed downward as well.

Typically, catheter 12 has an inner diameter (or the diameter of lumen 58) of between 6.5 and 7.0 mm (e.g., 6.85 mm). Typically, catheter 14 has an inner diameter (or the diameter of lumen 59) of between 4.7 and 5.3 mm (e.g., 5.1 mm). System 10, by providing slit 52 and depressible engager 54, provides a system in which the inner diameters of catheters 12 and 14 are maintained during given stages of the procedure. For example, engager 54 maintains the inner diameter of catheter 12 as catheter 14 is advanced within the lumen of catheter 12, and slit 52 maintains the inner diameter of catheter 14 once engager 54 pops up and is disposed within slit 52. That is, once catheters 12 and 14 are coupled via the engager and slit, the lumen of catheter 14 is typically constant along the length of the catheter (e.g., there are no protrusions into catheter 14), thereby facilitating sliding through the lumen of large elements.

FIG. 3B shows the axial advancement of a distal portion of catheter 14 through the lumen of catheter 12 in the direction as indicated by arrow 1. Typically, the advancement of catheter 14 through catheter 12 is controlled by the physician who moves handle 24 axially closer to handle 22. During the advancement of catheter 14 through catheter 12, engager 54 is maintained in a pushed state (as shown in section A-A of FIG. 3B) by a pushing force applied thereto by inner wall 51 of catheter 12. As shown in section B-B of FIG. 3B, inner wall 51 of outer catheter 12 pushes on engager 54, in the direction as indicated by the radial arrow. In response to the force applied on engager 54 by inner wall 51 of catheter 12, engager 54 is pushed and tab 56 is displaced at a non-zero angle with respect to axis 7 in order to allow for depression of engager 54. During the depression of engager 54, engager 54 is pushed slightly within lumen 59 of catheter 14.

As described hereinabove, inner wall 51 of catheter 12 is smooth and uninterrupted by recesses or slits (except for slit 52 at the distal end of catheter 12). First coupling 152 (e.g., slit 52 thereof) is disposed at a given longitudinal site of catheter 12, and slit 52 typically has a length L2 (shown in view B of FIG. 1) of between 5 and 15 mm, e.g., 10 mm. A proximal-most end of slit 52 is disposed up to 100 mm (e.g., up to 60 mm) from distal end 102 of catheter 12. Catheter 12 is typically between 80 and 100 cm long. Thus, inner wall 51 of the proximal portion of catheter 12, until the proximal-most end of slit 52, is smooth and uninterrupted by recesses or slits. Taken together, the depressibility of engager 54 and such a smooth configuration of inner wall 51 of catheter 12 enables rotation of catheter 14 by 360 degrees (i.e., as indicated by arrow 2) within the lumen of catheter 12.

For some applications, it is hypothesized that the relatively short lengths of couplings 152 and 154 relative to the lengths of catheters 12 and 14, and the absence of interruptions such as lateral openings (e.g., slits) and/or protrusions, other than those of the couplings, facilitates the use of catheters with lateral walls that are thinner than those of a catheter that, for example, comprises a coupling that has a longer relative length.

FIG. 3C shows further axial advancement of catheter 14 within the lumen of catheter 12. As described hereinabove, during the advancement, and prior to the engaging of engager 54 with slit 52 (as is described hereinbelow with reference to FIG. 3D), inner wall 51 pushes on engager 54 such that catheter 14 can be rotated to any suitable rotational orientation within outer catheter 12. For example, engager 54 is shown at 2 o'clock in section B-B of FIG. 3B, while engager 54 is shown at 11 o'clock in section B-B of FIG. 3C.

That is, while second coupling 154 (e.g., engager 54 thereof) is disposed proximal to the longitudinal site at which first coupling 152 (e.g., slit 52 thereof) is disposed, catheter 14 is rotatable within the lumen of catheter 12. Furthermore, prior to the engaging of engager 54 with slit 52 catheter 14 may be extracted from within the lumen of catheter 12.

FIG. 3C shows axial advancement of catheter 14 within catheter 12 in the distal direction, as indicated by arrow 1, in a manner in which engager 54 is about to engage with slit 52 at a distal portion of catheter 12. FIG. 3C shows a relative position of catheter 14 with respect to catheter 12 in a manner in which catheter 14 is not fully pushed within catheter 12. Handle 24 of catheter 14 is still distanced from handle 22 of catheter 12. However, catheter 14 is pushed distally sufficiently for distal end 104 and a portion of the distal end portion of catheter 14 to emerge from within catheter 12 and extend distally beyond distal end 102 of catheter 12.

Following further distal advancement of catheter 14 within catheter 12, and slight rotation of catheter 14 within the lumen of catheter 12, engager 54 of catheter 14 is aligned with slit 52 of catheter 12, as shown in FIG. 3D. In the absence of the pushing force of inner wall 51 of catheter 12 on engager 54, engager 54 returns to its resting state and protrudes within slit 52 so as to engage slit 52. That is, first coupling 152 is engaged with (i.e., coupled to) second coupling 154. As engager 54 returns to its resting state, tab 56 returns to a position in which it is parallel with respect to longitudinal axis 7. That is, in a given orientation of catheter 14, when second coupling 154 (e.g., engager 54 thereof) becomes disposed at the longitudinal site at which first coupling 152 (e.g., slit 52 thereof) is disposed, the second coupling automatically couples to the first coupling.

FIG. 3D shows engager 54 in a distal-most position within slit 52, i.e., a fully-pushed state of catheter 14. As such, handles 24 and 22 are disposed adjacently to each other. In this state, an exposed distal end portion 114 of catheter 14 extends beyond distal end 102 of catheter 12. Typically, at least a portion of distal end portion 114 is steerable and bendable, as is described hereinbelow. Distal end portion 114 of catheter 14 has a length L3 of between 25 and 35 mm, e.g., 30 mm. As described hereinabove, slit 52 has a length L2 of between 5 and 15 mm, e.g., 10 mm.

Reference is now made to FIGS. 1 and 3D. As shown in view B of FIG. 1, engager 54 has a longitudinal length L26 of between 2 and 3 mm, e.g., 2 mm. Length L26 facilitates motion of engager 54 along length L2 of slit 52. A proximal-most end of engager 54 is disposed up to 120 mm (e.g., up to 80 mm) from distal end 104 of catheter 14. As described hereinabove, a proximal-most end of slit 52 is disposed up to 100 mm (e.g., up to 60 mm) from distal end 102 of catheter 12. Thus, since slit 52 has a length L2 of between 5 and 15 mm, e.g., 10 mm, when engager 54 is disposed at a distal-most position within slit 52, as shown in FIG. 3D, exposed distal end portion 114 of catheter 14 has a length L3 of between 20 and 35 mm, e.g., 30 mm.

For some applications, the combined lengths of first and second couplings 152 and 154, respectively, is less than 30 mm, e.g., less than 20 mm. For applications in which first coupling 152 (e.g., slit 52) is between 5 and 15 mm, and second coupling 154 (e.g., engager 54) is between 2 and 3 mm, the combined lengths of first and second couplings 152 and 154, respectively, is less than 50 mm, e.g., less than 20 mm.

Engager 54 has a longitudinal length L26 that is less than 30% (e.g., less than 20%) of the longitudinal length of catheter 14. Typically, however, as described hereinabove, engager 54 has a length L26 of between 2 and 3 mm. That is, engager 54 has a longitudinal length that is less than 2% (e.g., less than 1%) of the longitudinal length of catheter 14.

Reference is now made to FIGS. 3C-D. A portion of exposed distal end portion 114 extends beyond distal end 102 of catheter 12 prior to engager 54 engaging slit 52. The length L2 of slit 52 enables retraction of catheter 14 between 5 and 15 mm, proximally from the fully-pushed state of catheter 14. As catheter 14 is retracted proximally, engager 54 moves proximally within slit 52 until a proximal-most end of engager 54 contacts a proximal-most end of slit 52. When engager 54 is disposed at the proximal-most end of slit 52, the distal end portion exposed from within catheter 12 is between 10 and 30 mm, e.g., 20 mm. When catheter 14 is pushed distally, engager 54 moves distally within slit 52 until a distal-most end of engager 54 contacts a distal-most end of slit 52.

Reference is again made to FIG. 3D. In the state in which engager 54 is disposed within slit 52, catheter 14 is restricted from rotating within the lumen of catheter 12, and catheters 12 and 14 are thereby rotationally locked with respect to each other.

FIG. 3E shows catheter 12 and 14 in a state in which catheter 14 has been pushed fully within catheter 12 (i.e., a state in which engager 54 is disposed at a distal-most end of slit 52 and handle 24 is disposed adjacently to handle 22). As described hereinabove, during the fully-pushed state of catheter 14, exposed distal portion 114 extends beyond distal end 102 of catheter 12 and has a length L3 of between 25 and 35 mm, e.g., 30 mm. Additionally, as is described herein, at least a portion of distal end portion 114 is steerable and comprises an exposed bending section 1403 which is a portion of a collective distal bending section 1405 of catheter 14 (described hereinbelow with reference to FIGS. 5 and 6). A distal end portion of catheter 12 comprises a bending section 1203 (described hereinbelow with reference to FIGS. 4 and 6). A proximal portion of bending section 1405 of catheter 14 is bendable and disposed within the lumen of catheter 12 at bending section 1203 thereof.

The distal end portion of catheter 12 is steerable in a first plane (e.g., a plane that is parallel with respect to the cardiac valve of the patient). Bending section 1403 of exposed distal portion 114 (and additional portions of collective bending section 1405) is steerable in second plane that is substantially perpendicular to the first plane in which the distal end portion of catheter 12 is steerable (e.g., a plane that is perpendicular with respect to the valve of the patient). Typically, this configuration is achieved by couplings 152 and 154 locking the catheters such that a plane on which pull wires 29a and 29b lie is generally orthogonal to a plane on which pull wires 31a and 31b lie. As shown, bending section 1203 of the steerable distal end portion of outer catheter 12 is maintained in its steered configuration, or in its spatial orientation, without substantially affecting the steering of exposed distal end portion 114 of guide catheter 14, nor of the bending of bending section 1403, nor of the collective bending section 1405 (including the proximal portion of bending section 1405 of catheter 14 that is disposed within the lumen of catheter 12 at bending section 1203 thereof). That is, first and second couplings 152 and 154, respectively, advantageously reduce the effect of the distal end portion of catheter 12 on the steering of section 114 and the bending of bending section 1405. That is, first and second couplings 152 and 154 of outer catheter 12 and guide catheter 14, respectively, collectively define a relative-spatial-orientation-controlling device which rotationally locks the relative spatial orientation of the steerable distal end portion and bending section 1203 of outer catheter 12 with respect to the steerable distal end portion and bending section 1405 of guide catheter 14, specifically of exposed bending section 1403.

Thus, for applications in which system 10 is used to treat the mitral valve, bending section 1203 of catheter 12 bends the steerable distal end portion of catheter 12 within the atrium in the first plane that is parallel with respect to the mitral valve. First and second couplings 152 and 154, respectively, enable (1) bending of bending section 1405 toward the valve in the second plane that is substantially perpendicular with respect to the first plane and to the plane of the mitral valve, while (2) restricting or minimizing the effect of the spatial orientation of bending section 1203 of catheter 12 on bending section 1405 of catheter 14.

Reference is now made to FIGS. 3A-E. It is to be noted that for some applications, slit 52 has a longitudinal length L2 of less than 20 cm, e.g., a length of less than 15 cm. That is, slit 52 has a longitudinal length L2 that is less than 30% (e.g., less than 20%) of the longitudinal length of catheter 12. Typically, however, as described hereinabove, slit 52 has a length L2 of between 5 and 15 mm, e.g., 10 mm. That is, slit 52 has a longitudinal length that is less than 2% (e.g., less than 1%) of the longitudinal length of catheter 12. For such applications, the proximal-most end of slit 52 is disposed up to 30 mm from distal end 102 of catheter 12.

It is to be noted that the scope of the present invention includes providing slit 52 and engager 54 at respective proximal portions of catheters 12 and 14, respectively. For such applications, a distal-most end of slit 52 is disposed up to 100 mm (e.g., up to 60 mm) from the proximal end of catheter 12 and a distal-most end of engager 54 is disposed up to 120 mm (e.g., up to 80 mm) from the proximal end of catheter 14.

Reference is now made to FIGS. 1, 2, and 3A-E. It is to be noted that first and second couplings 152 and 154, respectively, may be provided on any standard catheter. That is, coupling 152 comprises frame 50 which can be coupled to an external surface of any standard catheter (in which case, a corresponding slit would be made in the standard catheter). Additionally coupling 154 may be coupled to any standard catheter by coupling the base portion of coupling 154 to any standard catheter. Suitable adjustments to the standard catheter would be made to accommodate the displacing of tab 56 and engager 54 in response to pushing forces applied to engager 54.

Reference is now made to FIG. 4, which is a schematic illustration of catheter 12 comprising a multiple-durometer section 1210 at a distal steerable end portion of catheter 12, in accordance with some applications of the present invention. Multiple-durometer section 1210 has a length L18 of between 30 mm and 40 mm, e.g., 36 mm. Each section of multiple-durometer section 1210 has a respective durometer sections in Shore D, or scale D. Catheter 12 comprises a uniform durometer section 1205 that is disposed proximal to multiple-durometer bending section 1210. Typically, multiple durometer section 1210 and uniform durometer section 1205 comprise an elastic tubular polymer 1206 (e.g., sequences of polyamide 12 segments (PA12) and polytetramethylene glycol segments (PTMG), polyether block amide, or PEBA) that defines the tubular structure of catheter 12. Polymer 1206 has mechanical and dynamic properties which impart flexibility, impact resistance, energy return, and fatigue resistance to catheter 12.

As shown in the cross-sectional image, catheter 12 provides a wall which defines lumen 58. The inner wall of catheter 12 (which defines lumen 58) is coated with a friction-reducing liner comprising polytetrafluoroethylene (PTFE) so as to reduce friction during the sliding of catheter 14 through lumen 58 of catheter 12. The wall of catheter 12 is shaped to define secondary lumens 1211, which are typically spaced apart from each other by 180 degrees. A respective pull wire 29a and 29b (not shown in FIG. 4 for clarity of illustration, but are shown in FIGS. 1 and 2) is advanced through each lumen 1211. The inner walls of each secondary lumen 1211 is coated with a friction-reducing liner comprising polytetrafluoroethylene (PTFE) so as to reduce friction during the sliding of respective wires 29a and 29b therethrough.

Typically, catheter 12 has an inner diameter D1 (or the diameter of lumen 58) of more than 6.5 mm and/or less than 7.0 mm (e.g., 6.85 mm) and an outer diameter D2 of more than 7.0 mm and/or less than 9.0 mm (e.g., 8.3 mm).

It is to be noted that even though catheter 12 has multiple durometer segments, inner and outer diameters D1 and D2, respectively, remain constant along a longitudinal length L8 of catheter 12 (with the exception of outer diameter D2 being tapered at the distal end portion of section 1201, as is described hereinbelow).

Typically, catheter 12 has a longitudinal length L8 of between 700 and 1200 mm, e.g., between 800 and 900 mm, e.g., between 853 and 867 mm, e.g., 860 mm. Uniform durometer section 1205 has a length L9 that is between 770 and 860 mm, e.g., 824 mm. Tubular polymer 1206 extends an entire length L8 of catheter 12. Catheter 12 is surrounded by a braided mesh 1207, which typically comprises a flexible metal (e.g., stainless steel 304 or nitinol). Typically, braided mesh 1207 extends along the length of catheter 12 until a proximal portion at which the pull wires 29a and 29b (not shown for clarity of illustration) are exposed from within lumens 1211 at a proximal section of catheter 12, e.g., between 823 and 837 mm (e.g., 830 mm) from distal end 102 of catheter 12.

Section 1210 comprises a distal pull-ring section 1201 in which pull ring 11 is disposed. Typically, a distal-most portion of section 1201 is tapered so as to facilitate atraumatic advancement of catheter 12 through the vasculature of the patient. Section 1201 has a length of between 4 and 5 mm (e.g., 4.5 mm) and has a durometer of between 45D and 63D (e.g., 55D). Such a durometer of section 1201 imparts more hardness and rigidity to the distal portion of catheter 12 in which pull ring 11 is disposed, such that portion/section 1201 supports ring 11 and protects the distal portion of catheter 12 from the impact of forces applied thereto during the pulling of pull ring 11 by the pull wires. Typically, pull ring 11 has a length of between 2.5 and 2.6 mm, e.g., 2.54 mm. A distal transition section 1202 is disposed proximal to section 1201 and has a length L5 of between 1 and 2 mm (e.g., 1.5 mm) and has a durometer of between 63D and 72D (e.g., 72D). The relatively high durometer of section 1202 imparts hardness to section 1202 such that pull ring 11 is supported and maintained in place during the pulling of pull ring 11 by the pull wires. Thus, section 1202 helps overcome high tensile forces acting on the distal end of catheter 12.

Catheter 12 provides bending section 1203 proximally adjacent to section 1202. As shown in the enlarged image, bending section 1203 comprises a coil 1208 which is embedded within the tubular polymer 1206. Typically, coil 1208 comprises a flexible metal (e.g., stainless steel 304 or nitinol). Coil 1208 imparts efficient and durable bending (e.g., flexibility) to bending section 1203. Additionally, polymer 1206 at bending section 1203 has a durometer of between 25D and 45D (e.g., 35D) which provides a degree of softness that facilitates bending of the distal steerable portion of catheter 12 at bending section 1203. Bending section 1203 has a length L6 of between 22 and 27 mm, e.g., 25 mm.

Typically, bending section 1203 has a maximum bending angle between 120 and 140 degrees (e.g., 127 degrees). That is, bending section 1203 can bend between 0 and 140 degrees. For some applications, bending section 1203 has a pre-shaped angle of between 40 and 55 degrees (e.g., 45 degrees) so as to reduce force applied to bending section 1203 of catheter 12 by pull wires 29a and 29b.

It is to be noted that only tubular polymer 1206 and braided mesh 1207 extend proximally and distally beyond bending section 1203.

Proximally adjacent to bending section 1203 is a transition section 1204 having a length L7 of between 4 and 6 mm (e.g., 5 mm). Proximally adjacent to transition section 1203 is uniform durometer section 1205. Uniform durometer section 1205 has a durometer of between 63D and 72D (e.g., 72D). Transition section 1204 has a durometer of between 35D and 55D (e.g., 45D) so as to provide a transition from the relatively low durometer of bending section 1203 to the relatively high durometer of uniform durometer section 1205.

FIG. 4 shows the relative position of slit 52 with respect to distal end 102 of catheter 12. As described hereinabove, a proximal-most end of slit 52 is disposed up to 100 mm (e.g., up to 60 mm) from distal end 102 of catheter 12.

Typically, the spatial orientation of bending section 1203 is determined by pulling on pull wires 29a and 29b that are disposed within lumens 1211 (wires 29a and 29b are not shown for clarity of illustration). Bending section 1203, for some alternative applications of the present invention, may be pre-shaped (e.g., at 45 degrees with respect to a transverse plane provided by opposing pull wires 29a and 29b) to assume a given spatial orientation and the spatial orientation of section 1203 is additionally determined by pulling on pull wires 29a and 29b.

Figure 5:
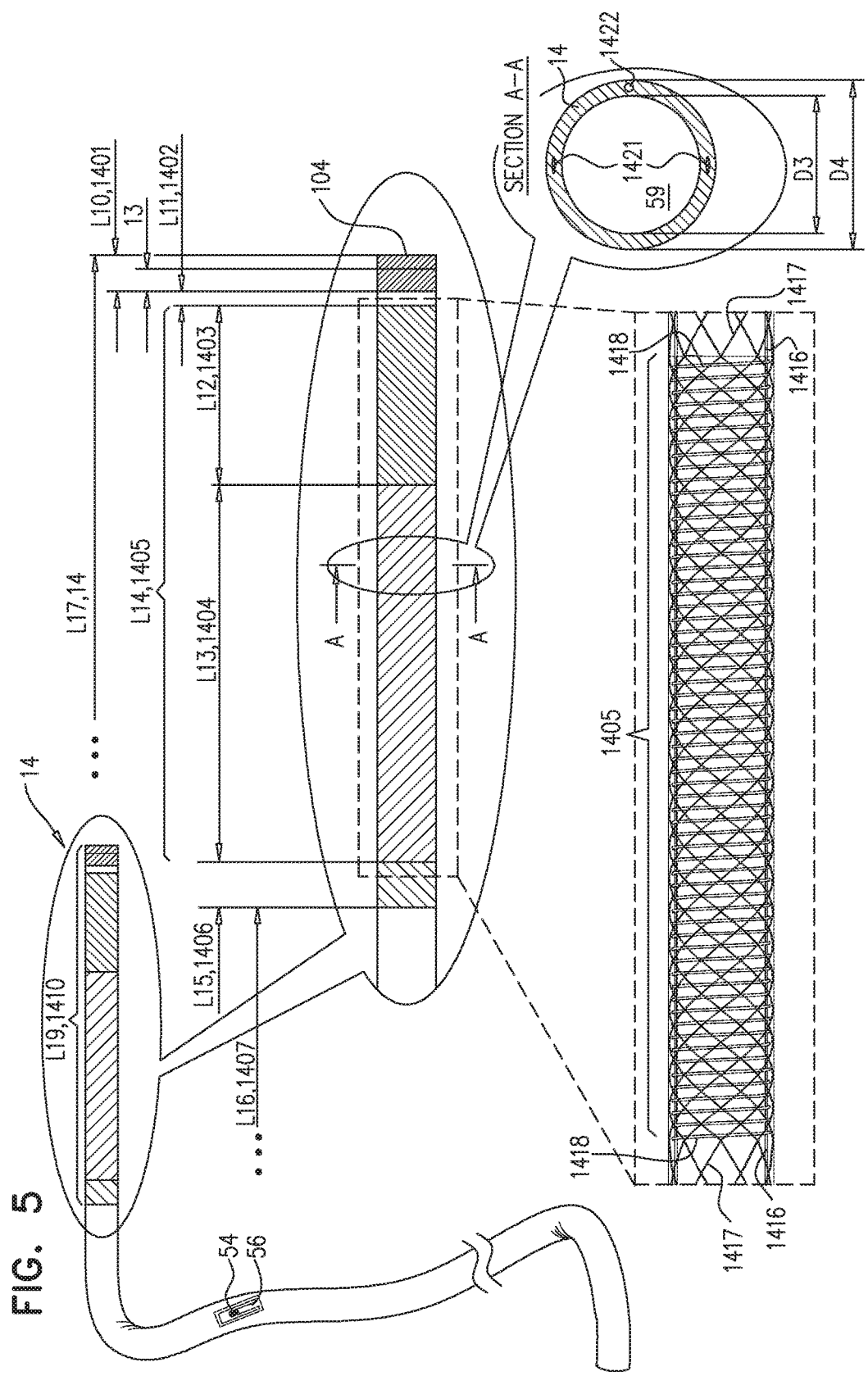

Reference is now made to FIG. 5, which is a schematic illustration of catheter 14 comprising a multiple-durometer section 1410 at a distal steerable end portion of catheter 14, in accordance with some applications of the present invention. Multiple-durometer section 1410 has a length L19 of between 70 mm and 80 mm, e.g., 74 mm. Each section of multiple-durometer section 1410 has a respective durometer sections in Shore D, or scale D. Catheter 14 comprises a uniform durometer section 1407 that is disposed proximal to multiple-durometer bending section 1410. Typically, multiple durometer section 1410 and uniform durometer section 1407 comprise an elastic tubular polymer 1416 (e.g., sequences of polyamide 12 segments (PA12) and polytetramethylene glycol segments (PTMG), polyether block amide, or PEBA) that defines the tubular structure of catheter 14. Polymer 1416 has mechanical and dynamic properties which impart flexibility, impact resistance, energy return, and fatigue resistance to catheter 14.

As shown in the cross-sectional image, catheter 14 provides a wall which defines lumen 59. The inner wall of catheter 14 (which defines lumen 59) is coated with a friction-reducing liner comprising polytetrafluoroethylene (PTFE) so as to reduce friction during the sliding of tube 19 (not shown for clarity of illustration, but shown in FIGS. 1 and 2) through lumen 59 of catheter 14. The wall of catheter 14 is shaped to define secondary lumens 1421, which are typically spaced apart from each other by 180 degrees. A respective pull wire 31a and 31b (not shown in FIG. 5 for clarity of illustration, but are shown in FIGS. 1 and 2) is advanced through each lumen 1421. The inner walls of each secondary lumen 1421 is coated with a friction-reducing liner comprising polytetrafluoroethylene (PTFE) so as to reduce friction during the sliding of respective wires 31a and 31b therethrough. Additionally, the wall of catheter 14 is shaped to define a secondary lumen 1422 for passage therethrough of guide member 86 (not shown in FIG. 5 for clarity of illustration, but are shown in FIGS. 1 and 2). The inner wall of secondary lumen 1422 is coated with a friction-reducing liner comprising polytetrafluoroethylene (PTFE) so as to reduce friction during the sliding of guide member 86 therethrough.

Typically, catheter 14 has an inner diameter D3 (or the diameter of lumen 59) of between 4.7 and 5.3 mm (e.g., 5.1 mm) and outer diameter D4 of between 6.3 and 6.9 mm (e.g., 6.5 mm or 6.7 mm).

It is to be noted that even though catheter 14 has multiple durometer segments, inner and outer diameters D3 and D4, respectively, remain constant along a longitudinal length L17 of catheter 14.

Typically, catheter 14 has a length L17 of between 1000 and 1500 mm, e.g., between 1190 and 1210 mm, e.g., 1200 mm. Uniform durometer section 1407 has a length L16 that is between 900 and 1400 mm, e.g., between 1110 and 1130 mm, e.g., 1126 mm. Tubular polymer 1416 extends an entire length L17 of catheter 14. Catheter 14 is surrounded by a braided mesh 1417, which typically comprises a flexible metal (e.g., stainless steel 304 or nitinol). Typically, braided mesh 1417 extends along the length of catheter 14 until a proximal portion at which the pull wires 31a and 31b (not shown for clarity of illustration) are exposed from within lumens 1421 at a proximal section of catheter 14, e.g., between 993 and 1007 mm (e.g., 1000 mm) from distal end 104 of catheter 14.

Section 1410 comprises a distal pull-ring section 1401 in which pull ring 13 is disposed. Section 1401 has a length of between 3.5 and 4.5 mm (e.g., 4.04 mm) and has a durometer of between 45D and 63D (e.g., 55D). Such a durometer of section 1401 imparts more hardness and rigidity to the distal portion of catheter 14 in which pull ring 13 is disposed, such that portion/section 1401 supports ring 13 and protects the distal portion of catheter 14 from the impact of forces applied thereto during the pulling of pull ring 13 by the pull wires. Typically, pull ring 13 has a length of between 2.5 and 2.6 mm, e.g., 2.54 mm. A distal transition section 1402 is disposed proximal to section 1401 and has a length L11 of between 1 and 2 mm (e.g., 1.5 mm) and has a durometer of between 63D and 72D (e.g., 72D). The relatively high durometer of section 1402 imparts hardness to section 1402 such that pull ring 13 is supported and maintained in place during the pulling of pull ring 13 by the pull wires. Thus, section 1402 helps overcome high tensile forces acting on the distal end of catheter 14.

Catheter 14 provides collective bending section 1405 proximally adjacent to section 1402. As shown in the enlarged image, bending section 1405 comprises a coil 1418 which is embedded within the tubular polymer 1416. Typically, coil 1418 comprises a flexible metal (e.g., stainless steel 304 or nitinol). Coil 1418 imparts efficient and durable bending to bending section 1405. Bending section 1405 has a length L14 of between 60 and 70 mm, e.g., 62 mm. Collective bending section 1405 comprises exposed bending section 1403 and a proximal bending section 1404.

Reference is now made to FIG. 6, which is a schematic illustration of a relative spatial orientation of the steerable distal end portions of catheters 12 and 14, respectively. Typically, in a fully-pushed state of catheter 14 within catheter 12, as described hereinabove, catheter 14 provides exposed distal end portion 114 that extends beyond distal end 102 of catheter 12. Distal end portion 114 comprises exposed bending section 1403. In the fully-pushed state of catheter 14, exposed bending section 1403 is configured to be exposed from and extend beyond distal end 102 of catheter 12, while at least a distal portion of proximal bending section 1404 is configured to remain concentrically disposed within the lumen of catheter 12 in general alignment with bending section 1203 of catheter 12, as indicated by the broken line in FIG. 6.

Reference is now made to FIGS. 5 and 6. Polymer 1416 at exposed bending section 1403 (in FIG. 5) has a durometer of between 20D and 35D (e.g., 25D) which provides a degree of softness at exposed bending section 1403 that facilitates bending of section 1403. Additionally, proximal bending section 1404 has a durometer of between 25D and 45D (e.g., 35D) which provides a degree of softness at exposed bending section 1404 that facilitates bending of section 1404. It is to be noted that the durometer of proximal bending section 1404 is higher than the durometer of exposed bending section 1403. Since the durometer of proximal bending section 1404 of catheter 14 is generally similar to the durometer of bending section 1203 of catheter 12, the steering of the distal end portion of catheter 14 (and of exposed distal portion 114) and the bending of bending section 1405 of catheter 14 (especially the bending of exposed bending section 1403) does not substantially influence the bending and spatial orientation of bending section 1203 at the distal end portion of catheter 12 when catheter 14 is disposed within catheter 12.

Typically, bending section 1405 has a maximum bending angle between 100 and 140 degrees (e.g., 117 degrees). That is, bending section 1405 can bend between 0 and 140 degrees. For some applications, at least a portion of bending section 1405 has a pre-shaped angle of between 40 and 55 degrees (e.g., 45 degrees) so as to reduce force applied to bending section 1405 of catheter 14 by pull wires 31a and 31b.

Reference is again made to FIG. 5. It is to be noted that only tubular polymer 1416 and braided mesh 1417 extend proximally and distally beyond bending section 1405.

Proximally adjacent to bending section 1405 is a transition section 1406 having a length L15 of between 4 and 6 mm (e.g., 5 mm). Proximally adjacent to transition section 1406 is uniform durometer section 1407. Uniform durometer section 1407 has a durometer of between 63D and 72D (e.g., 72D). Transition section 1406 has a durometer of between 35D and 55D (e.g., 45D) so as to provide a transition from the relatively low durometer of proximal bending section 1404 of bending section 1405 to the relatively high durometer of uniform durometer section 1407. FIG. 5 shows the relative position of slit engager 54 with respect to distal end 104 of catheter 14. As described hereinabove, a proximal-most end of engager 54 is disposed up to 120 mm (e.g., up to 80 mm) from distal end 104 of catheter 14.

Typically, the spatial orientation of bending section 1405 is determined by pulling on pull wires 31a and 31b that are disposed within lumens 1421 (wires 31a and 31b are not shown for clarity of illustration). Bending section 1405, for some alternative applications of the present invention, may be pre-shaped to assume a given spatial orientation and the spatial orientation of section 1405 is additionally determined by pulling on pull wires 31a and 31b.

Reference is now made to FIG. 7A, which is a schematic illustration of a catheter 1012 as described hereinabove with regard to catheter 12 with reference to FIG. 4, with the exception that catheter 1012 comprises a tubular portion 1250 that is shaped to define slit 52 described herein, in accordance with some applications of the present invention. Tubular portion 1250 comprises a flexible or rigid metal segment that is shaped to provide first coupling 152. For some applications, slit 52 is created in tubular portion 1250. For other applications, frame 50 (described hereinabove with reference to FIG. 1) is coupled to tubular portion 1250 in alignment with a slit generated therein.

During manufacture of catheter 1012, tubular portion 1250 is positioned longitudinally and coaxially between segments of section 1205 of catheter 1012. That is, a portion of section 1205 is cut in order to generate intermediate free ends, and tubular portion 1250 is attached at respective free ends thereof to the intermediate free ends of section 1205. For some applications, catheter 1012 is not cut, but rather catheter 1012 is comprised of two separate parts, each having free ends which are each coupled to portion 1250. For some applications, the intermediate free ends are coupled to respective metal segments, and tubular portion 1250 is coupled to the metal segments at the intermediate free ends of catheter 12 by being welded to the metal segments.

Typically, but not necessarily, the metal of portion 1250 is covered by plastic or the polymer of catheter 12, described hereinabove with reference to FIG. 4.

Typically, the pull wires of catheter 12 described hereinabove with reference to FIG. 2, run through secondary lumens in the wall of tubular portion 1250, or adjacently to the wall of portion 1250.

It is to be noted that tubular portion 1250 may be coupled to any suitable catheter known in the art.

Reference is now made to FIG. 7B, which is a schematic illustration of a catheter 1014 as described hereinabove with regard to catheter 14 with reference to FIG. 5, with the exception that catheter 1014 comprises a tubular portion 1450 that is shaped to define engager 54 and tab 56 described herein, in accordance with some applications of the present invention. Tubular portion 1450 comprises a flexible or rigid metal segment that is shaped to provide second coupling 154. That is, tubular portion 1450 provides slits 57 (as shown in FIG. 1) which define tab 56 and engager 54. Thus, for some applications, tubular portion 1450 and tab 56 are constructed from a single unit by creating slits in tubular portion 1450, and the protrusion of engager 54 is welded or otherwise coupled to a distal end of tab 56. For other applications, coupling 154 comprises a base which defines tab 56 and provides engager 54, and the base is coupled to tubular portion 1450.

During manufacture of catheter 1014, tubular portion 1450 is positioned longitudinally and coaxially between segments of section 1407 of catheter 1014. That is, a portion of section 1407 is cut in order to generate intermediate free ends, and tubular portion 1450 is attached at respective free ends thereof to the intermediate free ends of section 1407. For some applications, catheter 1014 is not cut, but rather catheter 1012 is comprised of two separate parts, each having free ends which are each coupled to portion 1250. For some applications, the intermediate free ends are coupled to respective metal segments, and tubular portion 1450 is coupled to the metal segments at the intermediate free ends of catheter 14 by being welded to the metal segments.

Typically, but not necessarily, the metal of portion 1450 is covered by plastic or the polymer of catheter 14, described hereinabove with reference to FIG. 5.

Typically, the pull wires of catheter 14 described hereinabove with reference to FIG. 2, run through secondary lumens in the wall of tubular portion 1450, or adjacently to the wall of portion 1450.

It is to be noted that tubular portion 1450 may be coupled to any suitable catheter known in the art.

Figure 8:
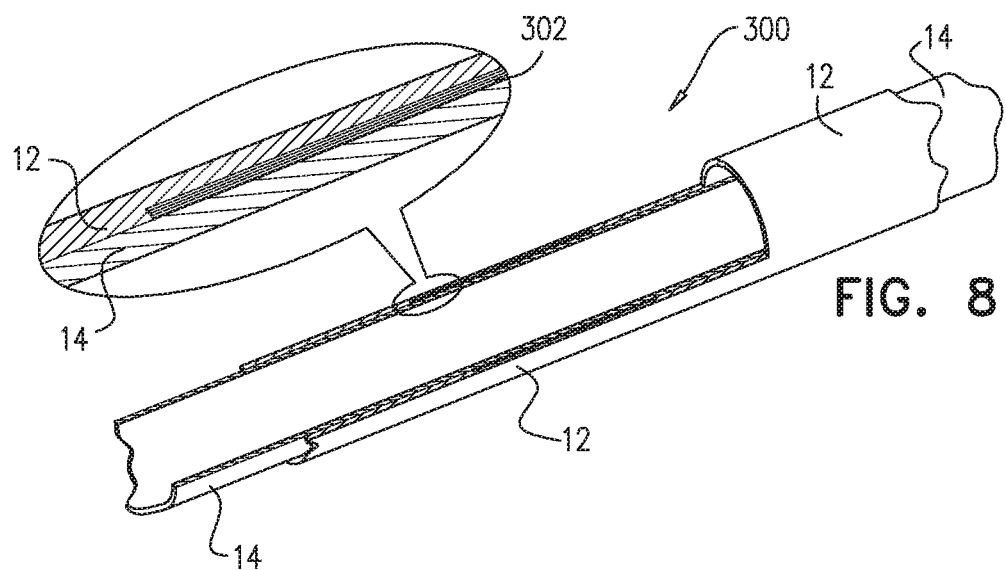
FIGS. 8-9 and 10A-C are schematic illustrations of respective relative-spatial-orientation-controlling devices of components of a multi-component tubular system, in accordance with respective applications of the present invention.

Reference is now made to FIG. 8, which is a schematic illustration of a system 300 comprising a generally-rigid segment 302 positioned between catheters 12 and 14 described herein, in accordance with some applications of the present invention. Typically, generally-rigid segment 302 is disposed at an outer surface of catheter 14 and is configured to extend between 20 and 40 degrees circumferentially around the outer surface of catheter 14. For some applications, segment 302 comprises a metal. Segment 302 is configured to restrict bending of catheter 14 in a given plane so as to minimize interference of the bending and steering of catheter 14 on catheter 12. Additionally, segment 302 is configured to minimize the effect of the spatial orientation of catheter 12 on the steering and bending of catheter 14. Thus, segment 302 provides a relative-spatial-orientation-controlling device to control the relative spatial orientations of the respective steerable distal end portions of catheters 12 and 14.

Generally-rigid segment 302 may be used with catheters 12 and 14 independently of or in combination with first and second couplings 152 and 154, as described hereinabove with reference to FIGS. 1, 2, and 3A-E.

Figure 9:
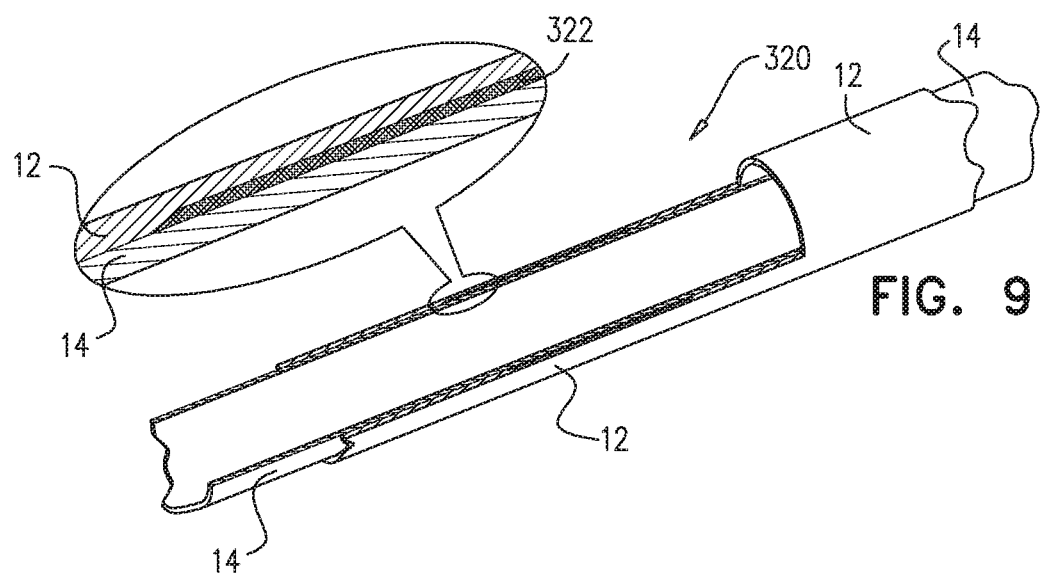

Reference is now made to FIG. 9, which is a schematic illustration of a system 320 comprising a friction-enhancing element 322 positioned between catheters 12 and 14 described herein, in accordance with some applications of the present invention. Typically, friction-enhancing element 322 is disposed at an outer surface of catheter 14 and is configured to extend between 20 and 40 degrees circumferentially around the outer surface of catheter 14. For some applications, friction-enhancing element 322 comprises a metal or a plastic. Friction-enhancing element 322 is configured to restrict bending of catheter 14 in a given plane so as to minimize interference of the bending and steering of catheter 14 on catheter 12. Additionally, friction-enhancing element 322 is configured to minimize the effect of the spatial orientation of catheter 12 on the steering and bending of catheter 14. Thus, friction-enhancing element 322 provides a relative-spatial-orientation-controlling device to control the relative spatial orientations of the respective steerable distal end portions of catheters 12 and 14.

Friction-enhancing element 322 may be used with catheters 12 and 14 independently of or in combination with first and second couplings 152 and 154, as described hereinabove with reference to FIGS. 1, 2, and 3A-E.

Figure 10A:
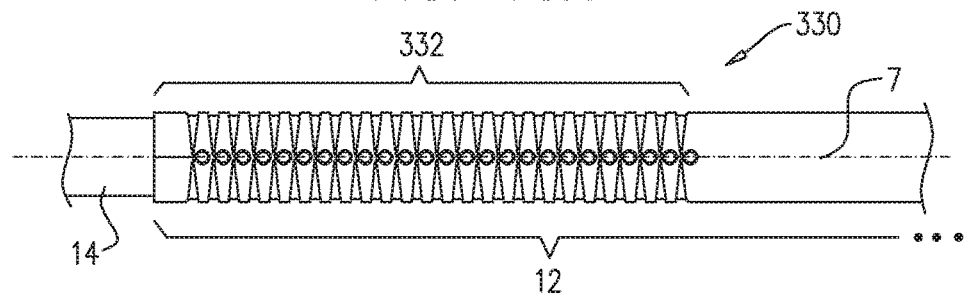
Figure 10B:
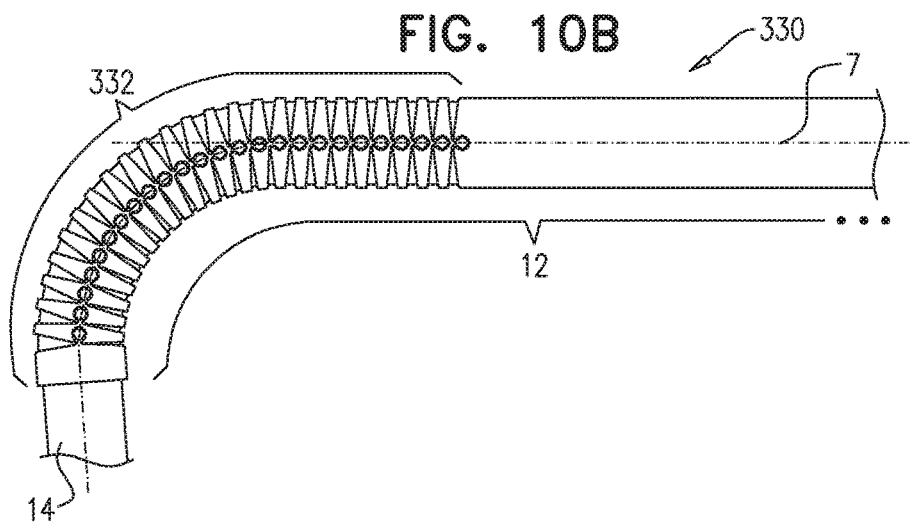
Figure 10C:
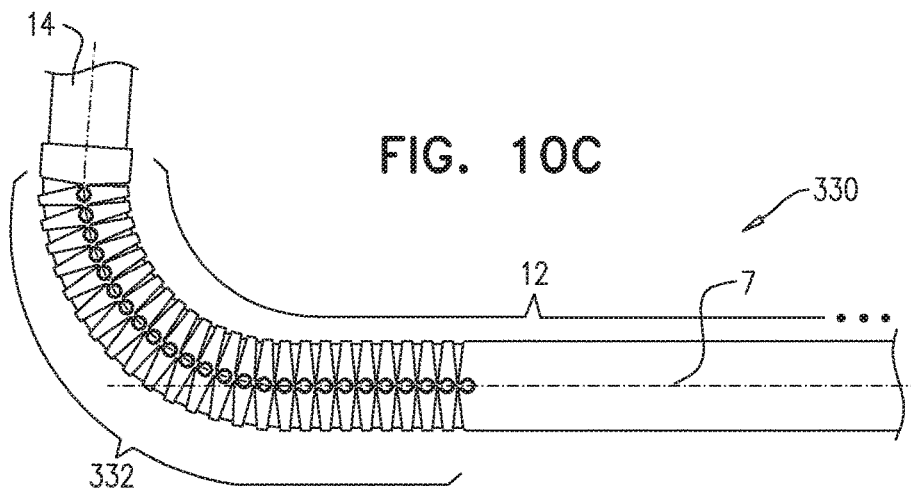

Reference is now made to FIGS. 10A-C, which are schematic illustrations of a system 330 comprising a hypertube section 332 disposed at a distal end of catheter 12 and 14 described herein, in accordance with some applications of the present invention. Typically, hypertube section 332 provides a lumen for passage therethrough of a distal portion of catheter 14. Hypertube section 332 is configured to facilitate bending of the distal portion of catheter 12 in the first plane, as shown in FIGS. 10B-C (e.g., the plane parallel with respect to the valve of the patient), while restricting bending of catheter 12 the second plane that is perpendicular with respect to the first plane. As such, during the bending and steering of the distal end portion of catheter 14 in the second plane, catheter 12 is restricted from being bent in the second plane, by hypertube section 332. Thus hypertube section 332 minimizes interference of the bending and steering of catheter 14 on catheter 12. Additionally, hypertube section 332 is configured to minimize the effect of the spatial orientation of catheter 12 on the steering and bending of catheter 14. Thus, hypertube section 332 provides a relative-spatial-orientation-controlling device to control the relative spatial orientations of the respective steerable distal end portions of catheters 12 and 14.

Hypertube section 332 may be used with catheters 12 and 14 independently of or in combination with first and second couplings 152 and 154, as described hereinabove with reference to FIGS. 1, 2, and 3A-E.

Figure 11A:
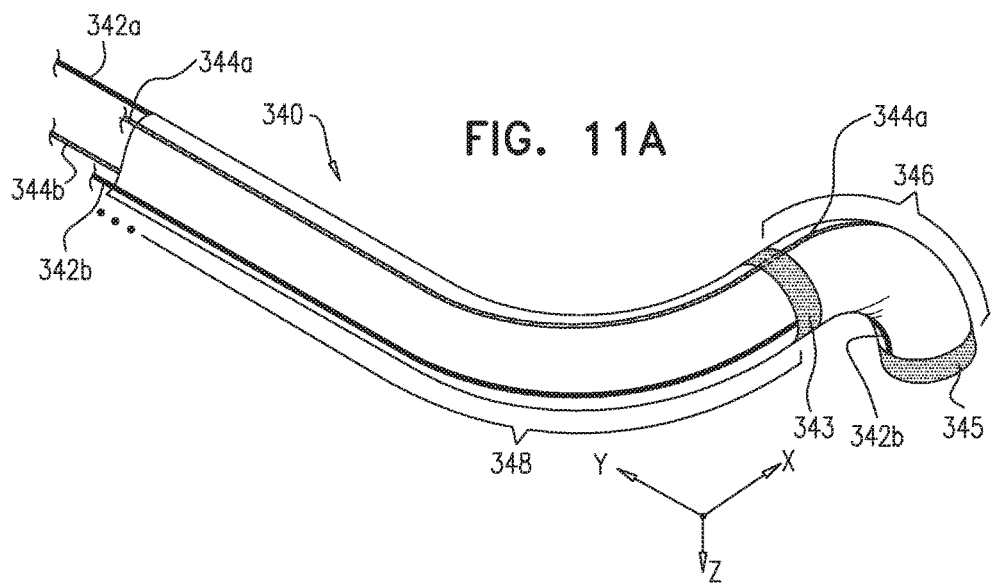
FIGS. 11A-B are schematic illustrations of a steerable catheter having multiple variable steering segments, in accordance with some applications of the present invention.
Figure 11B:
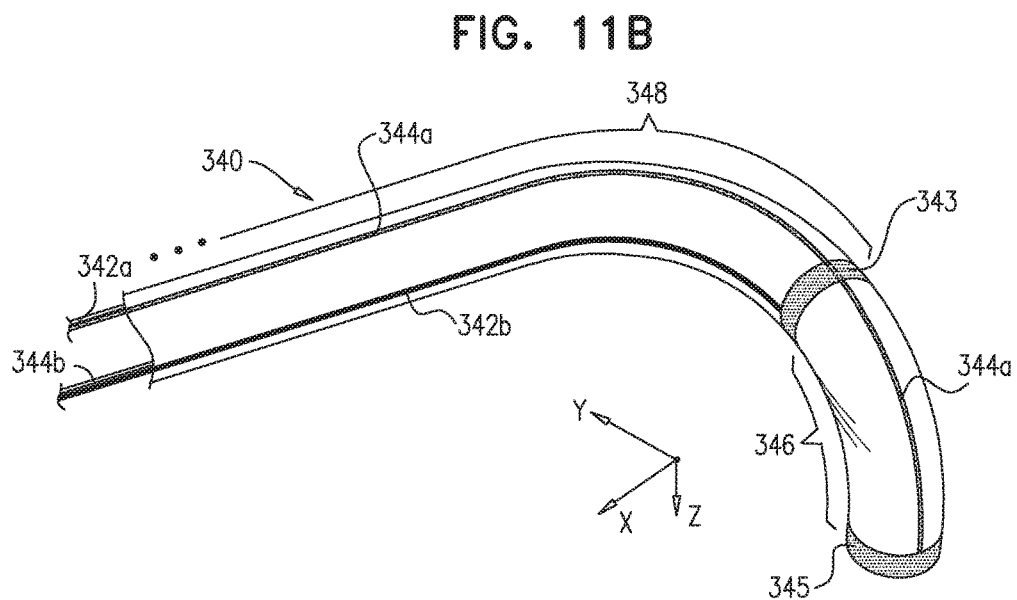

Reference is now made to FIGS. 11A-B, which are schematic illustrations of a catheter 340 having multiple steering segments (e.g., first and second steering segments 346 and 348, respectively), in accordance with some applications of the present invention. First steering segment 346 comprises a first pull ring 345 that is coupled to respective distal ends of first and second first-segment steering wires 344a and 344b. Steering wires 344a and 344b extend from the distal end of catheter 340 toward a proximal portion of catheter 340. Second steering segment 348 comprises a second pull ring 343 that is coupled to respective distal ends of first and second first-segment steering wires 342a and 342b. Steering wires 342a and 342b extend from pull ring 343 toward a proximal portion of catheter 340.

Segment 346 is configured to be coupled to only steering wires 344a and 344b. Steering wires 344a and 344b pass through respective channels provided by pull ring 343.

In response to the pulling of wires 342a and 342b steering segments 348 is steering in a first plane, and in response to the pulling of wires 344a and 344b steering segments 346 is steering in a second plane. For applications in which catheter 340 is used to deliver the annuloplasty structure 222 and anchor driver 36 described herein to a cardiac valve, segment 348 is configured to be steered in the plane that is parallel with respect to the valve, and segment 346 is configured to be steered toward the valve in a second plane that is perpendicular with respect to the plane of the valve.

For some applications catheter 340 may be introduced within multi-component tubular system 10, described hereinabove with reference to FIGS. 1 and 2, in place of catheters 12 and 14. That is reference force tube 19, implant 222, channel 18, and deployment manipulator 61 may be advanced within a lumen of catheter 340.

Reference is made to FIGS. 12A-B, which are schematic illustrations of rotating deployment element 38, as described hereinabove with reference to FIG. 2, in radially-expanded and radially-compressed states, respectively, in accordance with some applications of the present invention. For some applications, rotating deployment element 38 is shaped to define at least two prongs 124A and 124B that extend in a distal direction from a proximal base 122 of the deployment element. Engagement elements 120A and 120B extend in a distal direction from prongs 124A and 124B, respectively. The engagement elements are typically male, and, for example, may together have a cross-sectional shape that is rectangular, e.g., square. Optionally, rotating deployment element 38 comprises more than two prongs and two engagement elements, e.g., three or four of each.

Rotating deployment element 38 is typically configured to assume a radially-expanded state as its resting state, as shown in FIG. 12A. In this expanded state, engagement elements 120A and 120B, as well as prongs 124A and 124B, are positioned apart from one another. In this state, the engagement elements are shaped and sized to engage tool-engaging head 62 of anchor 32, as shown, for example, in FIG. 2.

As shown in FIG. 12B, the rotating deployment element 38 assumes a radially-compressed state, when the engagement elements and prongs are squeezed together, such as by passing through the engaging opening of tool-engaging head 62 of anchor 32.

Reference is now made to FIGS. 13A-B, which are schematic illustrations of rotating deployment element 38 engaging tool-engaging head 62 of anchor 32, with the element 38 in locked and unlocked states, respectively, in accordance with an application of the present invention. In accordance with this application, rotating deployment element 38 comprises a locking mechanism 128, which is configured to selectively assume locked and unlocked states. When locking mechanism 128 assumes the locked state (FIG. 13A), the locking mechanism prevents disengagement of rotating deployment element 38 from the anchor which rotating deployment element 38 currently engages. This locking allows deployment element 38 to proximally withdraw anchor 32 if necessary, without coming disengaged therefrom. Disengagement is thus prevented even upon withdrawal of the rotating deployment element in the proximal direction. When the locking mechanism assumes the unlocked state (FIG. 13B), the locking mechanism does not prevent disengagement of the rotating deployment element from the anchor upon withdrawal of rotating deployment element 38 in the proximal direction. The rotating deployment element thus can be disengaged and withdrawn from the anchor in a proximal direction. It is noted that even when the locking mechanism assumes the unlocked state, the rotating deployment element generally does not disengage from the anchor unless the rotating deployment element is withdrawn in the proximal direction. As mentioned above with reference to FIG. 12A, rotating deployment element 38 is typically configured to assume a radially-expanded state as its resting state. In this radially-expanded state, engagement elements 120A and 120B are positioned apart from each other, and engage tool-engaging head 62 of anchor 32. Thereby, even in the unlocked state shown in FIG. 13B, engagement elements 120A and 120B typically remain positioned apart from each other.

For some applications, locking mechanism 128 comprises elongate rod 130. In order to cause the locking mechanism to assume the locked position, rod 130 is advanced distally between engagement elements 120A and 120B. The rod holds the engagement elements in their radially-expanded state, as described hereinabove with reference to FIG. 12A, thereby preventing the engagement elements from assuming the radially-compressed state shown in FIG. 12B and disengaging from the anchor. In the radially-expanded state, the engagement elements engage a proximal engaging surface 66 of tool-engaging head 62 of anchor 32. In order to cause locking mechanism 128 to assume the unlocked state, rod 130 is withdrawn proximally from between engagement elements 120A and 120B. As a result, as deployment element 38 is subsequently pulled in the proximal direction, the engagement elements are pushed together by tool-engaging head 62 (e.g., proximal engaging surface 66 thereof), so as to assume the radially-compressed state shown in FIG. 12B. In the radially-compressed state, the engagement elements do not engage the tool-engaging head of the anchor, and deployment element 38 is thereby decouplable from anchor 32.

Movement of rod 130 proximally and distally is described hereinabove with reference to FIG. 2. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the physician releases anchor 32 from deployment element 38 when finger-engager 131 is pulled proximally, thereby pulling rod 130 proximally. When rod 130 is moved proximally, the distal portion of rod 130 is removed from between engagement elements 120A and 120B, and elements 120A and 120B assume the unlocked state described hereinabove.

Providing this selective, actively-controllable engagement and release of the anchor allows rotating deployment element 38 to be used to unscrew an already-deployed anchor from the tissue, and/or to proximally withdraw an anchor, without deployment element 38 unintentionally disengaging from the anchor head. Such unscrewing or proximal withdrawal may allow an anchor to be repositioned if it is initially coupled to the tissue in an incorrect location. Rotating deployment element 38 is capable of performing this redeployment for both (a) the anchor that has been most recently deployed into the tissue, and to which the deployment element 38 is still coupled, and (b) an anchor that was previously deployed, and from which deployment element 38 has already been decoupled (and, optionally, even after another anchor has subsequently been deployed). In the latter case, deployment element 38 re-engages the anchor that is to be redeployed. For some applications, such re-engaging occurs when deployment manipulator/element 38, in its compressed state, reenters the opening of tool-engaging head 62 and coupling elements 120A and 120B are allowed to assume their radially-expanded states (e.g., such as by advancing rod 130 therebetween).

Reference is now made to FIGS. 14A-I, which are schematic illustrations of a procedure for implanting an annuloplasty ring structure 222 to repair a mitral valve 230, in accordance with an application of the present invention. This procedure is one exemplary procedure that can be performed using system 10.

Annuloplasty ring structure 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises flexible sleeve 26 and a plurality of anchors 32. Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some application, annuloplasty ring structure 222 is implemented using techniques described in U.S. application Ser. No. 12/437,103, filed May 7, 2009 which published as US 2010/0286767 (now U.S. Pat. No. 8,715,342), and/or U.S. application Ser. No. 12/689,635, filed Jan. 19, 2010 which published as US 2010/0280604 (now U.S. Pat. No. 8,545,553), both of which are assigned to the assignee of the present application and are incorporated herein by reference. As described hereinabove, annuloplasty ring structure 222 comprises adjusting mechanism 40. The adjusting mechanism comprises a rotatable structure, such as a spool, arranged such that rotation of the rotatable structure contracts the implant structure. The implant further comprises a longitudinal member, such as a wire, which is coupled to the adjusting mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

Figure 14A:
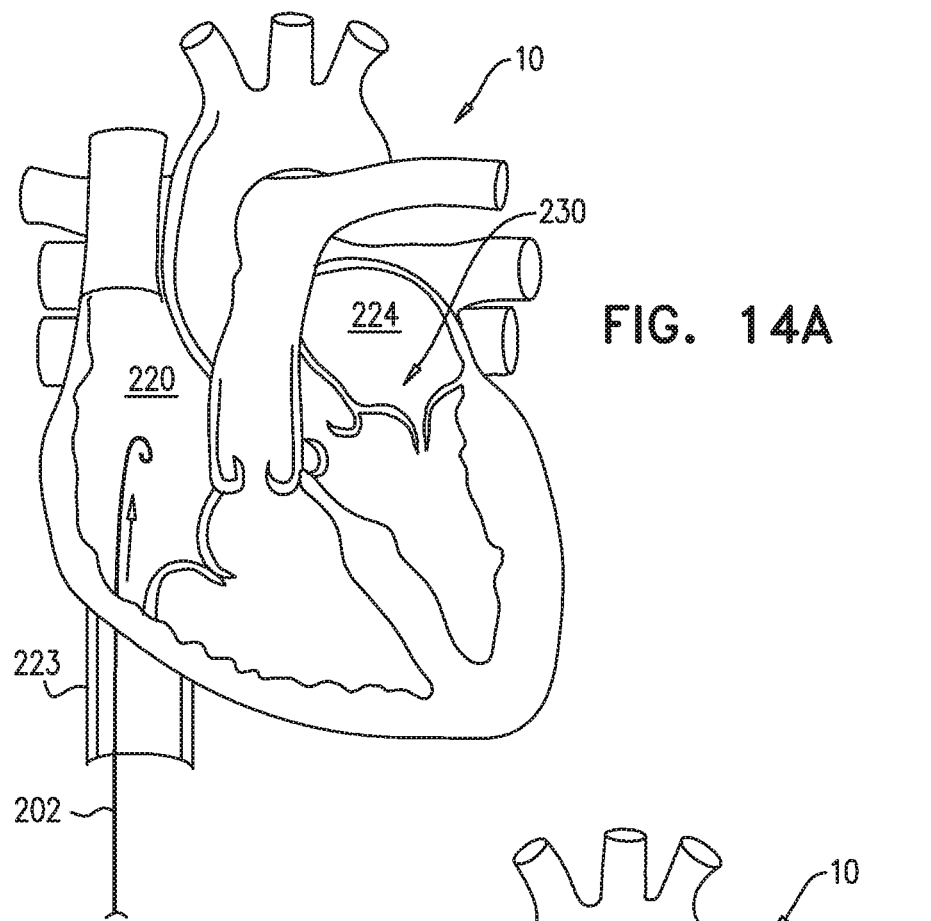
FIGS. 14A-I are schematic illustrations of a procedure for implanting an annuloplasty ring structure to repair a mitral valve, in accordance with some applications of the present invention.

As shown in FIG. 14A, the procedure typically begins by advancing a semi-rigid guidewire 202 into a right atrium 220 of the patient. The procedure is typically performed with the aid of imaging, such as fluoroscopy, transesophageal echo, and/or echocardiography.

Figure 14B:
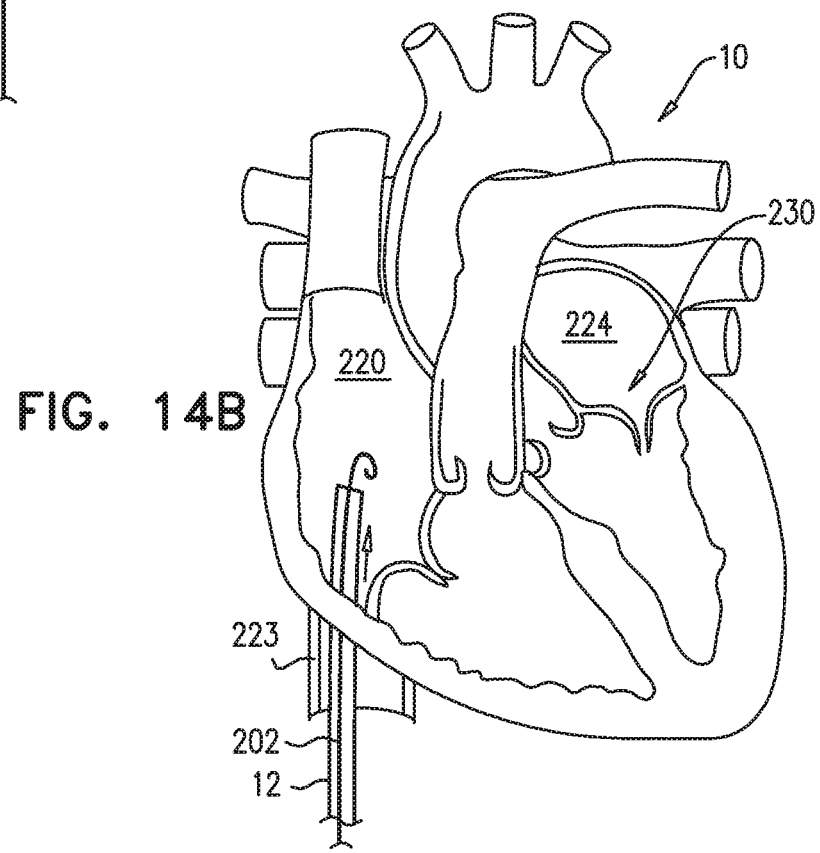

As show in FIG. 14B, guidewire 202 provides a guide for the subsequent advancement of outer catheter 12 therealong and into the right atrium. Once a distal portion of catheter 12 has entered the right atrium, guidewire 202 is retracted from the patient's body. Catheter 12 typically comprises a 14-24 F sheath, although the size may be selected as appropriate for a given patient. Catheter 12 is advanced through vasculature into the right atrium using a suitable point of origin typically determined for a given patient. For example:

catheter 12 may be introduced into the femoral vein of the patient, through an inferior vena cava 223, into right atrium 220, and into a left atrium 224 transseptally, typically through the fossa ovalis;

catheter 12 may be introduced into the basilic vein, through the subclavian vein to the superior vena cava, into right atrium 220, and into left atrium 224 transseptally, typically through the fossa ovalis; or catheter 12 may be introduced into the external jugular vein, through the subclavian vein to the superior vena cava, into right atrium 220, and into left atrium 224 transseptally, typically through the fossa ovalis.

For some applications of the present invention, catheter 12 is advanced through inferior vena cava 223 of the patient (as shown) and into right atrium 220 using a suitable point of origin typically determined for a given patient.

Figure 14C:
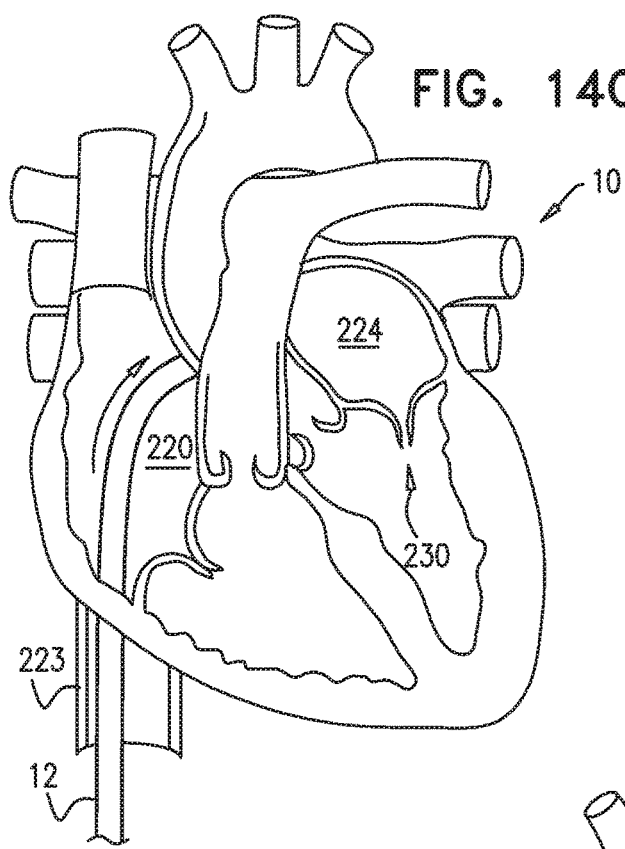

Catheter 12 is advanced distally until the sheath reaches the interatrial septum, and guidewire 202 is withdrawn, as shown in FIG. 14C.

Figure 14D:
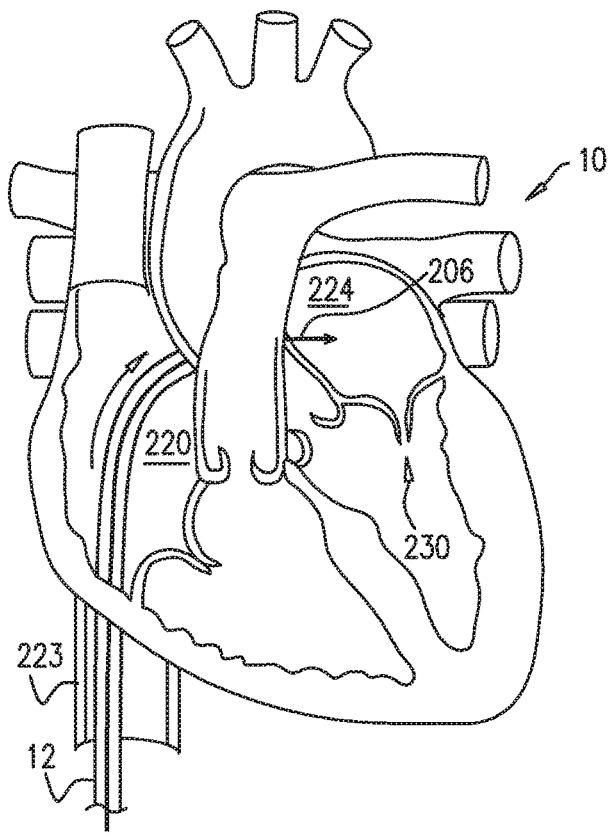

As shown in FIG. 14D, a resilient needle 206 and a dilator (not shown) are advanced through catheter 12 and into the heart. In order to advance catheter 12 transseptally into left atrium 224, the dilator is advanced to the septum, and needle 206 is pushed from within the dilator and is allowed to puncture the septum to create an opening that facilitates passage of the dilator and subsequently catheter 12 therethrough and into left atrium 224. The dilator is passed through the hole in the septum created by the needle. Typically, the dilator is shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum. As shown in FIG. 4, for example, a distal-most end 102 of catheter 12 is tapered so as to facilitate passage of the distal portion of catheter 12 through the opening in the septum.

Figure 14E:
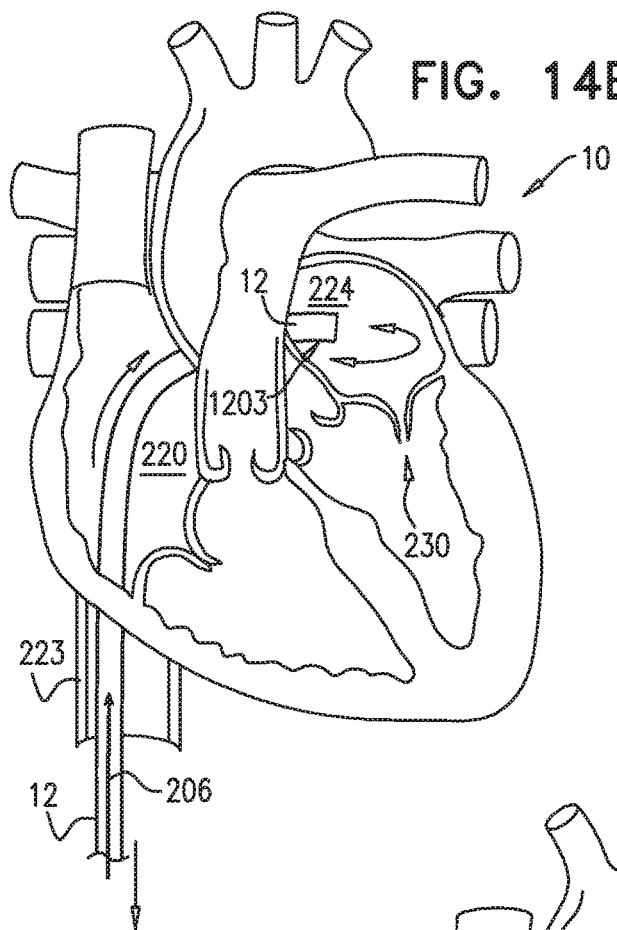

The advancement of catheter 12 through the septum and into the left atrium is followed by the extraction of the dilator and needle 206 from within catheter 12, as shown in FIG. 14E. Once the distal portion of catheter 12 is disposed within atrium 224, the steerable distal end portion of catheter 12 (which includes at least a portion of bending section 1203, as described hereinabove with reference to FIGS. 4 and 6) is steered in a first plane that is parallel to a plane of the annulus of mitral valve 230. Such steering moves the distal end portion of catheter 12 in a direction from the interatrial septum toward surrounding walls of the atrium, as indicated by the arrow in atrium 224. As described hereinabove, steering of the distal portion of catheter 12 is performed via steering knob 210 of handle 22 in handle portion 101 (in FIGS. 1 and 2).

Figure 14F:
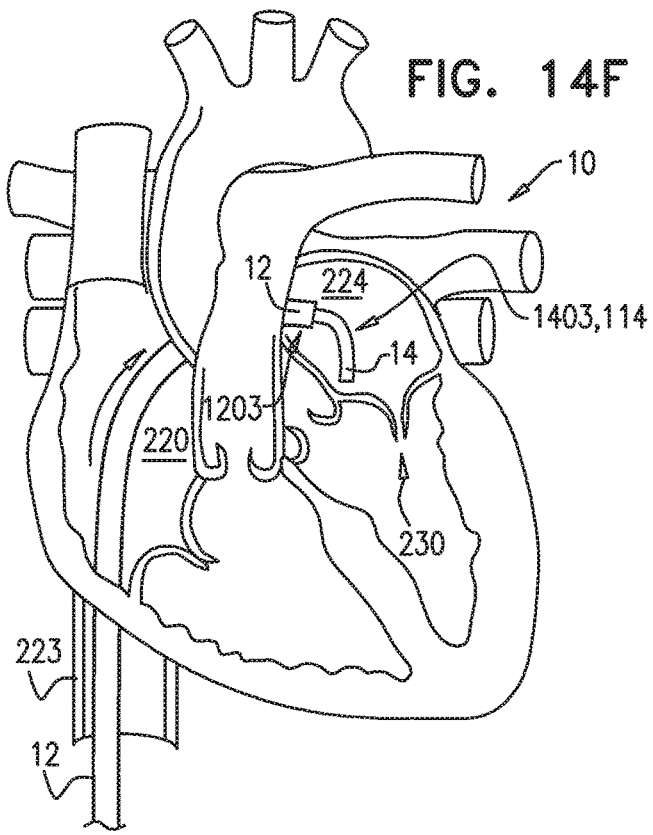

As shown in FIG. 14F, annuloplasty ring structure 222 (not shown for clarity of illustration, with anchor deployment manipulator 61 therein) is advanced through guide catheter 14, which is in turn, advanced through catheter 12 into left atrium 224. As shown in FIG. 14F, exposed distal end portion 114 of catheter 14 extends beyond distal end 102 of catheter 12. Exposed distal end portion 114 is then (1) steered toward the annulus of valve 230 along a plane that is perpendicular with respect to the steering plane of catheter 12 and that is perpendicular with respect to valve 230, and is (2) bent, via bending section 1403 (as described hereinabove with reference to FIGS. 5 and 6) toward valve 230. As described hereinabove, steering of the distal portion of catheter 14 is performed via steering knob 214 of handle 24 in handle portion 101 (in FIGS. 1 and 2).

Figure 14G:
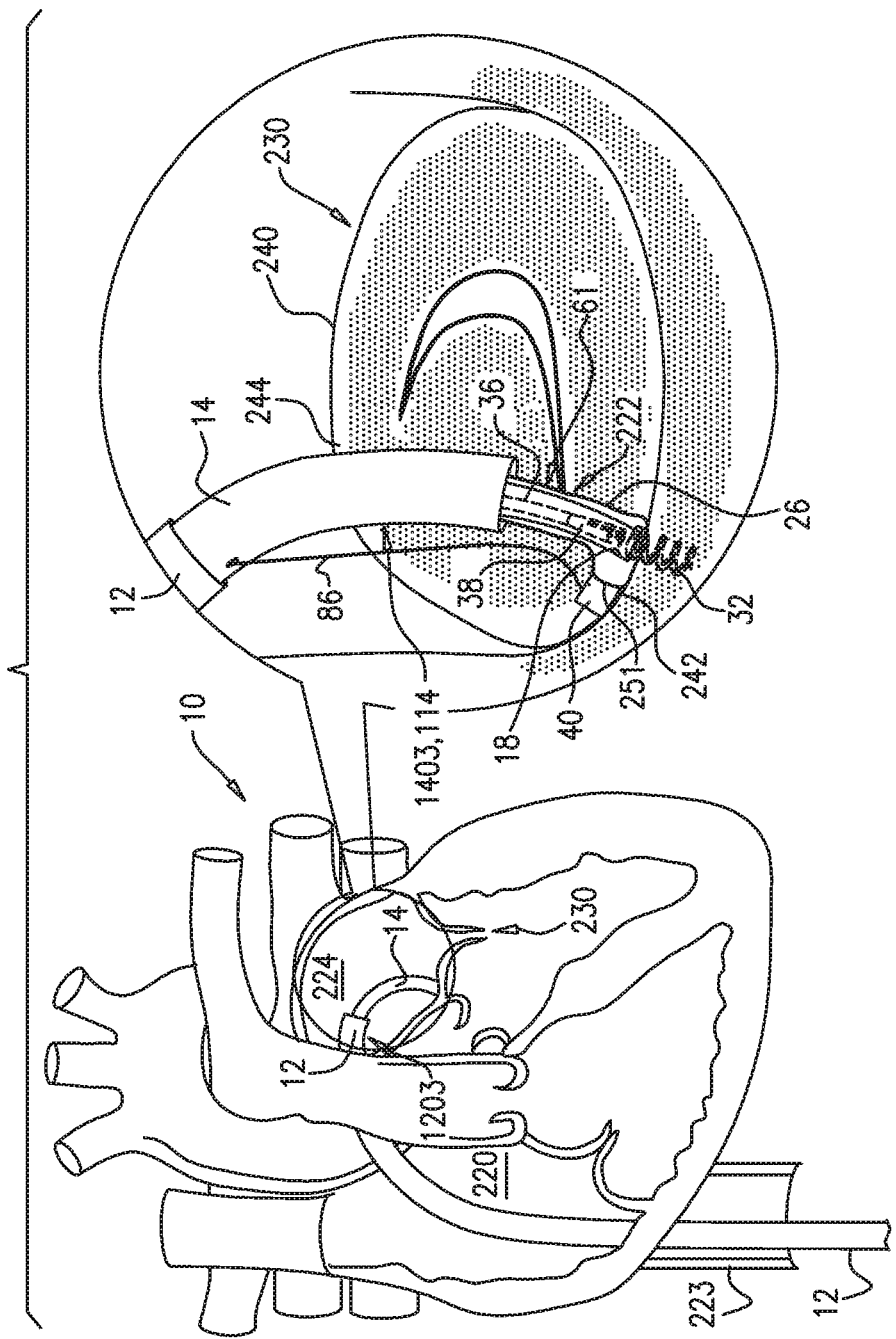

As shown in FIG. 14G, a distal end 251 of sleeve 26 is positioned in a vicinity of a left fibrous trigone 242 of an annulus 240 of mitral valve 230. (It is noted that for clarity of illustration, distal end 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys a first anchor 32 through the wall of sleeve 26 (by penetrating the wall of the sleeve in a direction in a direction parallel to a central longitudinal of deployment manipulator 61, or anchor driver 36, through the distal end of channel 18, and/or parallel to central longitudinal axis of tissue coupling element 60 of anchor 32) into cardiac tissue near the trigone, using the techniques described hereinabove with reference to FIGS. 12A-B and 13A-B. Following the deployment of anchor 32 in the cardiac tissue, deployment element 38 is decoupled from anchor 32 by moving rod 130 proximally, as described hereinabove with reference to FIGS. 2, 12A-B, and 13A-B.

Anchors 32 are typically deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the cardiac tissue in a direction parallel to the central longitudinal axis through the distal end of manipulator 61. Such an angle is typically provided and/or maintained by channel 18 being more rigid than sleeve 26. Distal end 17 (shown in FIG. 2) of channel 18 is typically brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 may be placed (e.g., pushed) against the wall of the sleeve, sandwiching the sleeve against the cardiac tissue.

For some applications, this placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

For some applications of the present invention, anchors 32 may be deployed from a lateral portion of manipulator 61.

Figure 14H:
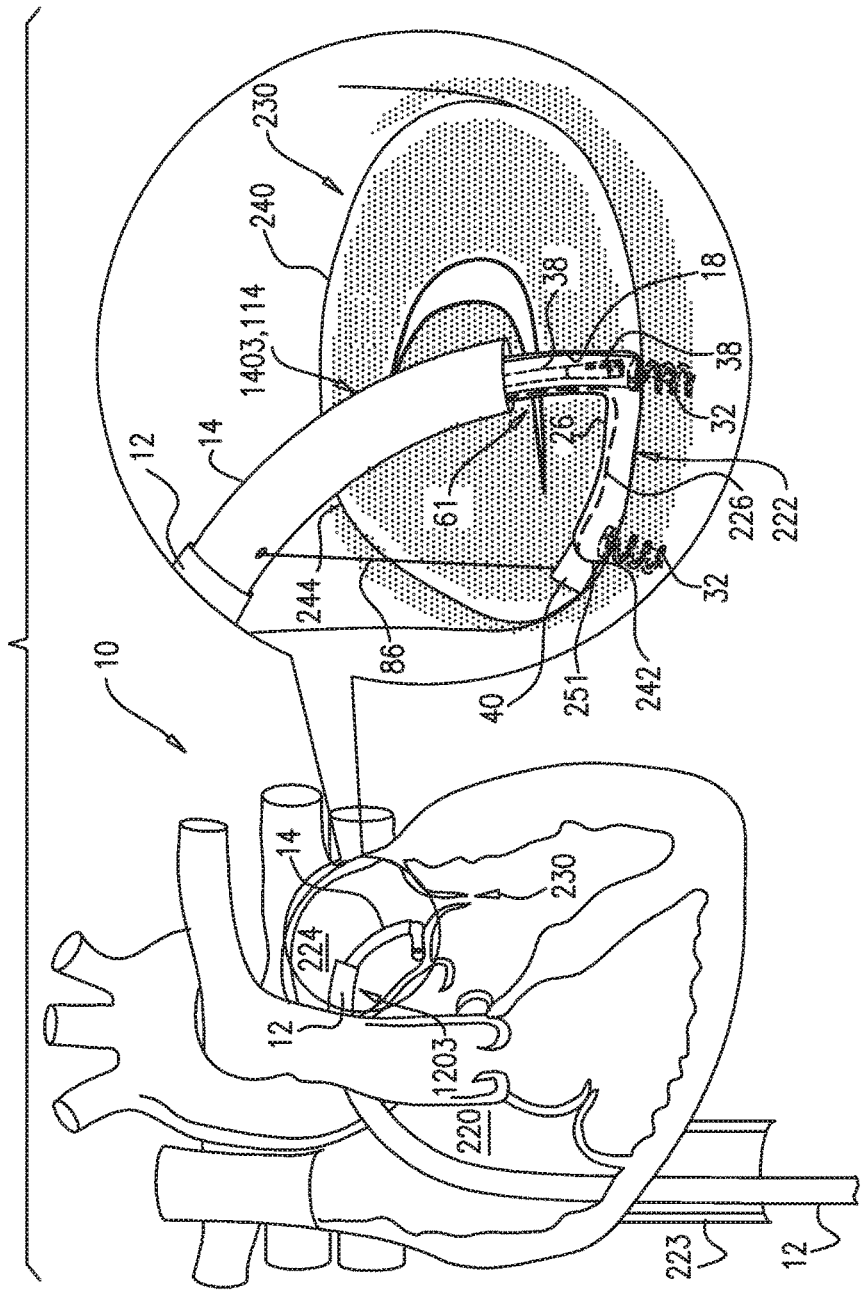

Reference is now made to FIGS. 14G and 2. Following the deployment of the first anchor, a distal portion of sleeve 26 is decoupled from a portion of implant-decoupling channel 18. In order to decouple the portion of sleeve 26 from outer surface of channel 18, (1) channel 18 is pulled proximally, while (2) reference-force tube 19 is maintained in place in a manner in which a distal end of tube 19 provides a reference force to sleeve 26 in order to facilitate retraction freeing of a successive portion of sleeve 26 from around channel 18. In order to decouple sleeve 26 from the outer surface of channel 18, (1) channel 18 is pulled proximally, while (2) reference-force tube 19 is maintained in place. An indicator 2120 (shown herein with reference to FIGS. 30A-B) on handle 126 provides an indication of how much channel 18 is withdrawn from within sleeve 26 (i.e., how much the delivery tool is decoupled from sleeve 26, and how much sleeve has advanced off channel 18 and against tissue). A proximal end of channel 18 is coupled to a knob 94 (FIG. 2) which adjusts an axial position of channel 18 proximally and distally with respect to reference-force tube 19 and sleeve 26. As shown in FIG. 14H, deployment manipulator 61 is repositioned along annulus 240 to another site selected for deployment of a second anchor 32. Reference is now made to FIGS. 1 and 14H. Such repositioning of manipulator 61 is accomplished by:

(1) the steering of the distal end portion of catheter 12 (e.g., by steering knob 210 of handle 22) in the first plane that is parallel with respect to annulus 240 of valve 230 to a desired spatial orientation and in a manner which bends bending section 1203 of catheter 12, (2) the steering of the distal end portion of portion of catheter 14 (e.g., by steering knob 214 of handle 24) in the second plane that is perpendicular with respect to annulus 240 of valve 230 to a desired spatial orientation, and in a manner which bends bending section 1405 of catheter 14 (specifically bending section 1403), (3) by axially moving catheter 14 with respect to catheter 12 via knob 216, (4) by axially moving the stand supporting handles 22 and 24 to move both catheters 12 and 14, (5) by moving tube 19 and sleeve 26 axially by sliding mount 93 along track 90 via knob 95, and/or (6) by moving channel 18 relative to tube 19 by actuating knob 94.

Typically, the first anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first anchor 32 holds the anchored end of sleeve 26 in place, so that the sleeve is drawn from the site of the first anchor towards the site of the second anchor. Typically, as sleeve 26 is decoupled from channel 18, deployment manipulator 61 is moved generally laterally along the cardiac tissue, as shown in FIG. 14H. Deployment manipulator 61 deploys the second anchor through the wall of sleeve 26 into cardiac tissue at the second site. Depending on the tension applied between the first and second anchor sites, the portion of sleeve 26 therebetween may remain tubular in shape, or may become flattened, which may help reduce any interference of the ring with blood flow.

Figure 14I:
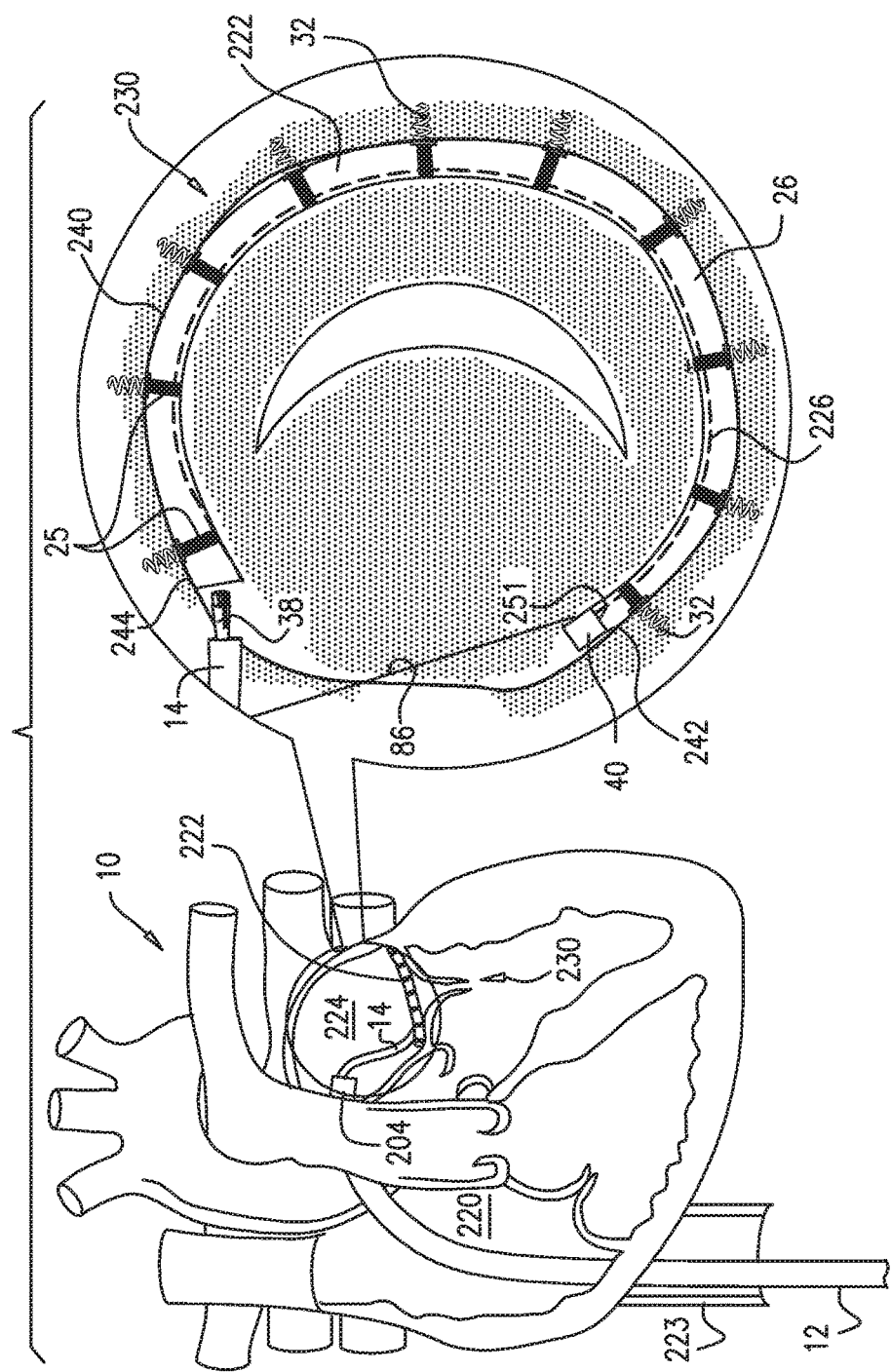

As shown in FIG. 14I, deployment manipulator 61 is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Then, system 10 is removed, leaving behind guide member 86. A rotation tool (not shown) is then threaded over and advanced along guide member 86 toward adjusting mechanism 40 and is used to rotate the spool of adjusting mechanism 40, in order to tighten structure 222 by adjusting a degree of tension of contracting member 226, as is described hereinbelow with reference to FIG. 17. Once the desired level of adjustment of structure 222 is achieved (e.g., by monitoring the extent of regurgitation of the valve under echocardiographic and/or fluoroscopic guidance), the rotation tool and guide member 86 are removed from the heart. For some applications, a distal portion of guide member 86 may be left within the heart of the patient and the proximal end may be accessible outside the body, e.g., using a port. For such applications, adjusting mechanism 40 may be accessed at a later stage following initial implantation and adjustment of ring structure 222.

As shown, sleeve 26 of ring structure 222 comprises a plurality of radiopaque markers 25, which are positioned along the sleeve at respective longitudinal sites to indicate anchor-designated target areas. The markers may provide an indication in a radiographic image (such as a fluoroscopy image) of how much of sleeve 26 has been deployed at any given point during an implantation procedure, in order to enable setting a desired distance between anchors 32 along the sleeve 26.

Alternatively, annuloplasty ring structure 222 is implanted by right or left thoracotomy, mutatis mutandis.

For some applications of the present invention, following implantation of sleeve 26 along the annulus, an excess portion of sleeve 26 may be present at the proximal portion of sleeve. In such applications, following removal of manipulator 61, a cutting tool (not shown) may be advanced within channel 18 and into the lumen of the excess portions of sleeve 26 (e.g., from within sleeve 26) in order to cut the sleeve proximal to the proximal-most-deployed anchor 32.

Figure 15:
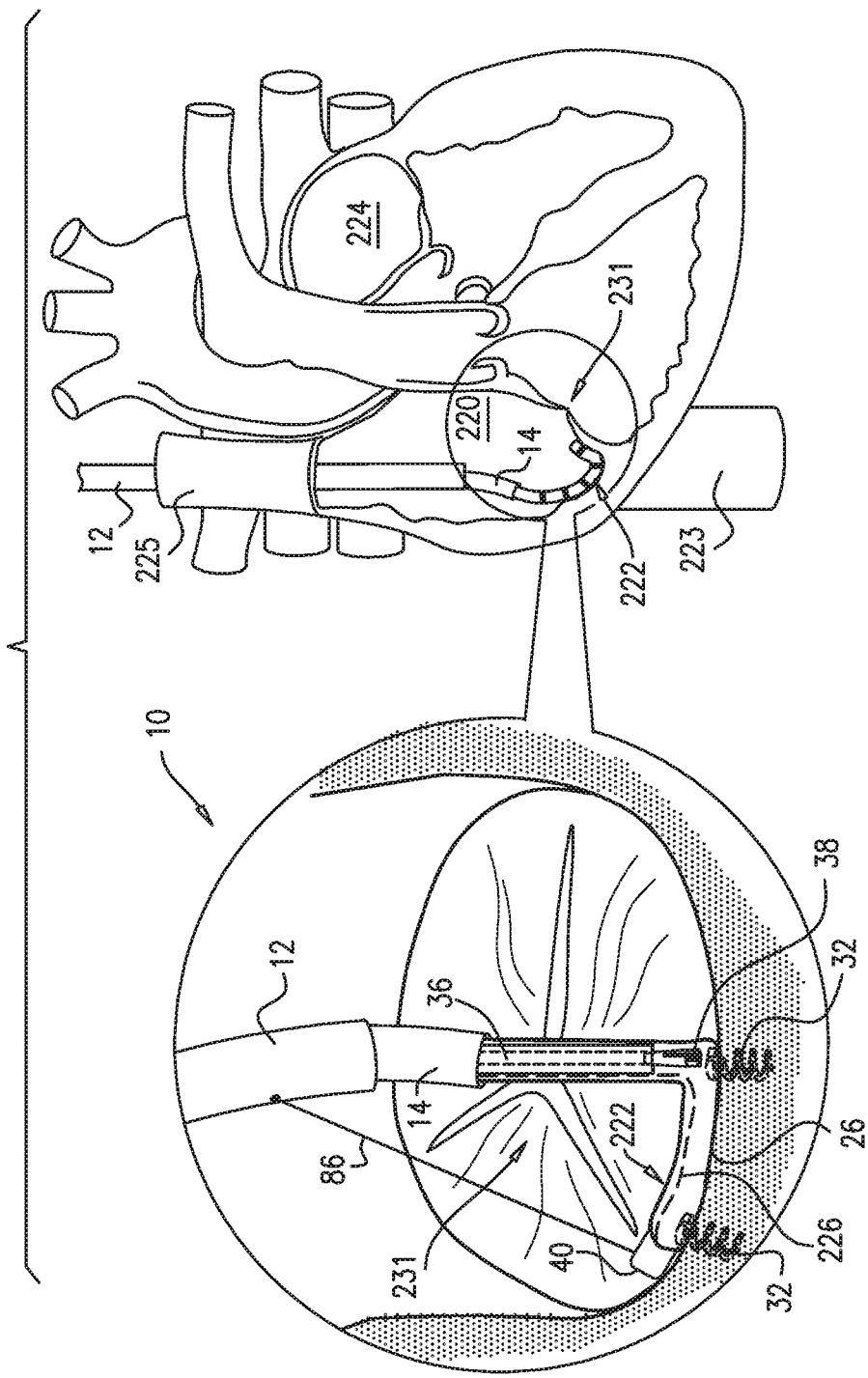
FIG. 15 is a schematic illustration of a procedure for implanting an annuloplasty ring structure to repair a tricuspid valve, in accordance with some applications of the present invention.

Reference is made to FIG. 15. For some applications of the present invention, annuloplasty ring structure 222 is used to treat an atrioventricular valve other than the mitral valve, i.e., tricuspid valve 231, using system 10 in a similar method as described hereinabove with reference to FIGS. 14A-I, in accordance with some applications of the present invention.

For these applications, ring structure 222 and other components of system 10 described hereinabove as being placed in the left atrium are instead placed in the right atrium 220. FIG. 15 shows accessing right atrium 220 through superior vena cava 225 by way of illustration and not limitation.

Components of system 10 may be advanced into the right atrium through inferior vena cava 223.

Although annuloplasty ring structure 222 is described hereinabove as being placed in an atrium, for some application the ring is instead placed in either the left or right ventricle.

Accordingly, it is noted that, annuloplasty ring structure 222 and other components of system 10 described hereinabove and methods shown in the application can be used on any cardiac valve (e.g., the mitral, tricuspid, aortic, and/or pulmonary).

Figure 16:
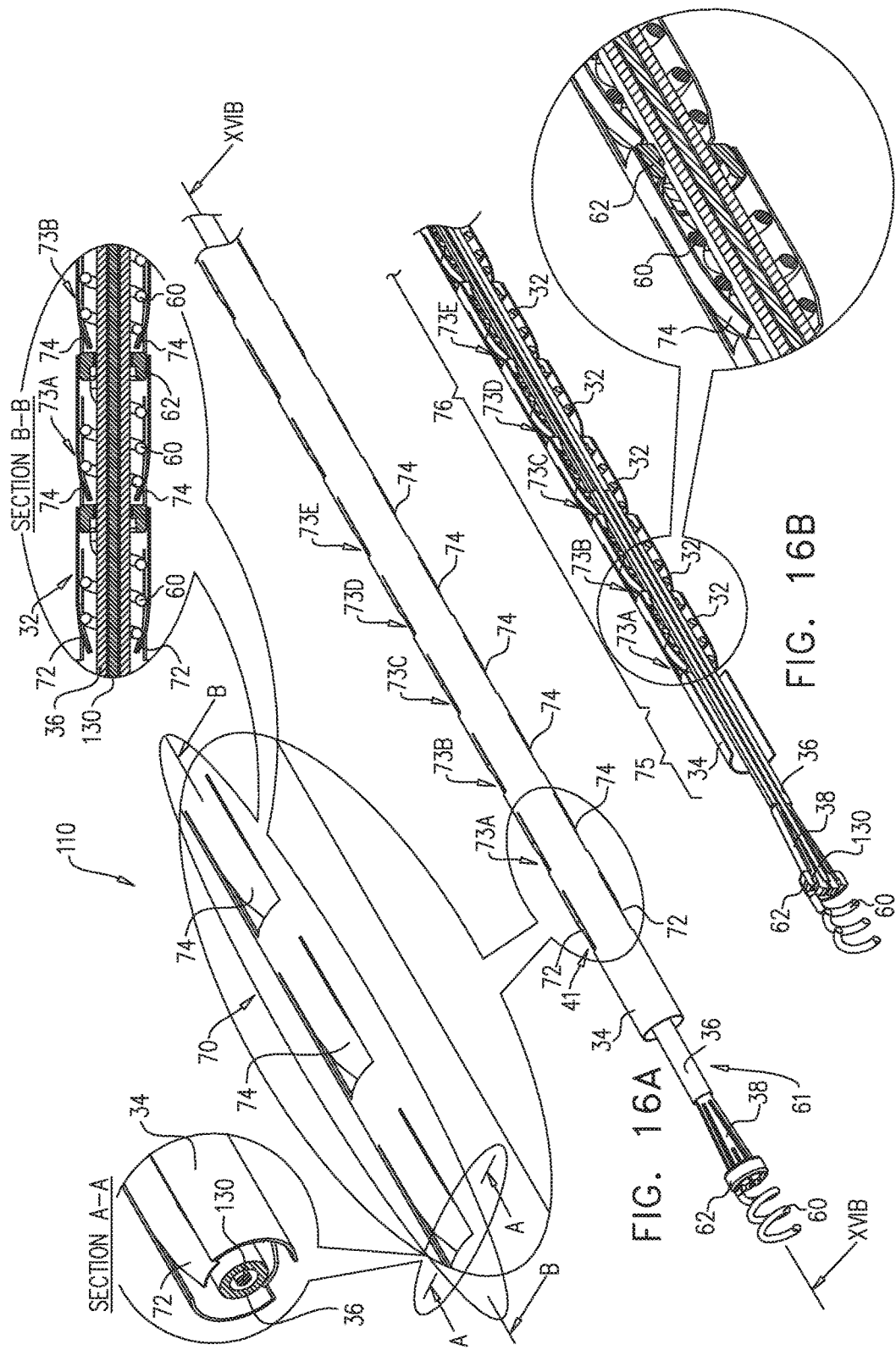
FIGS. 16A-B are schematic illustrations of a configuration of an anchor deployment system, in accordance with some applications of the present invention.

Reference is made to FIGS. 16A-B, which are schematic illustrations of a multiple-anchor deployment system 110 which is configured to be used in combination with anchor driver 36, as described hereinabove with reference to FIGS. 1 and 2, in accordance with an application of the present invention. In this configuration, an anchor restraining mechanism 70 typically comprises one or more distal tabs 72 for temporarily restraining the distal-most anchor 32 currently stored in an anchor storage area 76 from advancing in the distal direction. The distal tabs may be cut out of a flexible outer tube 34, as shown, or they may be provided as separate elements coupled to the outer tube. The distal tabs apply a force in a radially-inward direction against a distal portion of anchor 32, gently squeezing against the distal portion. The force is sufficient to prevent distal motion of distal-most anchor 32 and the other anchors currently stored in anchor storage area 76, which otherwise would be advanced distally by passive force applied thereto by other anchors in storage area 76. However, the radially-inward force is insufficient to prevent distal advancement of distal-most anchor 32 when the anchor is engaged and advanced distally by rotating deployment element 38, as described herein. For some applications, anchor restraining mechanism 70 comprises two distal tabs 72, typically on opposite sides of the outer tube (typically axially aligned with each other), as shown, while for other applications, the anchor restraining mechanism comprises exactly one distal tab, or three or more distal tabs, e.g., three or four distal tabs (typically axially aligned with one another).

Typically, for applications in which system 10 comprises multiple-anchor deployment system 110, outer tube 34 is disposed between anchor driver 36 and channel 18 (shown in FIGS. 1-2). Typically, a distal anchor manipulation area 75 is provided, which is typically flexible and steerable. Typically, only one anchor at a time is deployed through anchor manipulation area 75 and into the tissue of the patient, such that no more than exactly one anchor is within anchor manipulation area 75 at any given time. As a result, anchor manipulation area 75 retains its flexibility. Because the anchors are typically rigid, when more than one of the anchors are longitudinally contiguously positioned within storage area 76, the area of the tool in which the anchors are positioned becomes fairly stiff, substantially losing the flexibility it would otherwise have. Thus, while anchor storage area 76 is fairly rigid, anchor manipulation area 75 remains flexible because it only contains exactly one anchor at a given time. The stiffness of the area of the tool in which the anchors are positioned also may enable the user to better control the exact location of distal-most anchor 32 currently stored in anchor storage area 76.

Anchor restraining mechanism 70 comprises a plurality of sets 73 of proximal tabs 74, labeled 73A, 73B, 73C, 73D, and 73E in FIGS. 16A-B. Each set of proximal tabs 74 engages exactly one anchor 32. For example, the distal ends of proximal tabs 74 of set 73A engage the proximal end of the tool-engaging head of distal-most anchor 32, and the distal ends of proximal tabs 74 of set 73B engage the proximal end of the tool-engaging head of second-to-distal-most anchor 32.

Sets 73 thus provide respective anchor storage locations. Therefore, the anchor restraining mechanism comprises a number of sets 73 greater than or equal to the number of anchors 32 initially stored in anchor storage area 76. For some applications, anchor restraining mechanism 70 comprises between 6 and 20 sets 73, such as between 8 and 16 sets 73. For some applications, each of sets 73 comprises two proximal tabs 74, typically on opposite sides of the outer tube (typically axially aligned with each other), as shown, while for other applications, each of the sets comprises exactly one proximal tab, or three or more proximal tabs, e.g., three or four proximal tabs (typically axially aligned with one another).

For some applications, each of sets 73 (except the proximal-most set 73) additionally functions as a distal tab 72 for the anchor proximally adjacent to the set. For example, set 73A, in addition to engaging distal-most anchor 32A, also prevents distal motion of second-to-distal-most anchor 32.

Each of anchors 32 remains in place in its initial, respective anchor storage location in anchor storage area 76, until the anchor is individually advanced out of anchor storage area 76 during deployment by deployment manipulator 61.

The anchor to be deployed is the distal-most one of the anchors stored in anchor storage area 76, and is initially restrained in the anchor storage area by anchor restraining mechanism 70. Anchor driver 36 is advanced in a distal direction until rotating deployment element 38 directly engages tool-engaging head 62 of the anchor (by "directly engages," it is meant that rotating deployment element 38 comes in direct contact with the anchor, rather than indirect contact via one or more of the other anchors). Rotating deployment element 38 assumes its radially-expanded state, as described hereinbelow with reference to FIGS. 12A and 13A, to enable this engagement.

In order to deploy anchors 32, anchor driver 36 is advanced in the distal direction, until rotating deployment element 38 brings the anchor into contact with the tissue of the patient at a first site. For example, the tissue may be cardiac tissue. Typically, deployment manipulator 61 is configured such that, as rotating deployment element 38 advances each of the anchors in the distal direction, only the single anchor 32 currently being advanced is within distal anchor manipulation area 75. Rotating deployment element 38 is rotated, in order to screw helical tissue coupling element 60 of the anchor into the tissue. For some applications, rotating deployment element 38 is rotated by rotating anchor driver 36. For other applications, rotating deployment element 38 is rotated by rotating an additional rotation shaft provided within anchor driver 36, which additional shaft is coupled to rotating deployment element 38. Rotation of rotating deployment element 38 typically rotates only the anchor currently engaged by the deployment element, while the other anchors still stored in the storage area typically are not rotated.

For applications in which system 10 comprises multiple-anchor deployment system 110, deployment manipulator 61 comprises anchor driver 36, deployment element 38, and outer tube 34.

Typically, anchor 32 is deployed from the distal end of outer tube 34 of tool 30 into cardiac tissue in a direction parallel to a central longitudinal axis of outer tube 34 through the distal end of tube 34, and/or parallel to central longitudinal axis of tissue coupling element 60 of anchor 32, as described herein.

The evacuation of the distal-most anchor from anchor restraining mechanism 70 frees up the anchor restraining mechanism for the next distal-most anchor remaining in anchor storage area 76.

After the distal-most anchor has been coupled to the tissue, rotating deployment element 38 is disengaged from the anchor by withdrawing the rotating deployment element in a proximal direction. As the rotating deployment element passes through the next anchor in the proximal direction (i.e., the anchor positioned at set 73A), the rotating deployment element is squeezed by the engaging opening of tool-engaging head 62 of the next anchor, causing the rotating deployment element to assume its radially-compressed state, as described hereinbelow with reference to FIGS. 12B and 13B.

Deployment element 38 is repositioned to deploy a second anchor 32 at a second site of the tissue, different from the first site. Such repositioning is typically accomplished using the steering functionality of catheters 12 and 14, as described hereinabove. The steps of the deployment method are repeated, until as many anchors 32 as desired have been deployed, at respective sites, e.g., a first site, a second site, a third site, a fourth site, etc.

Figure 17:
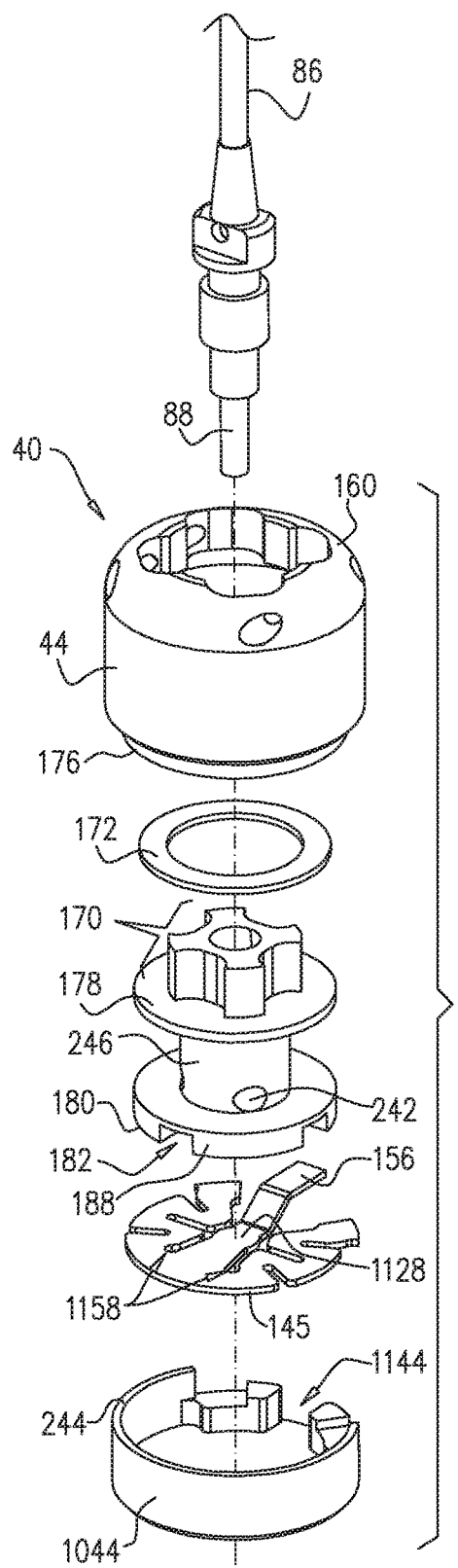
FIG. 17 is a schematic illustration of components of a rotational adjusting mechanism, in accordance with some applications of the present invention.

Reference is now made to FIG. 17, which is a schematic illustration showing a relationship among individual components of adjusting mechanism 40, in accordance with some applications of the present invention. Adjusting mechanism 40 is shown as comprising spool housing 44 which defines an upper surface 160 and a lower surface 176 defining a recessed portion (as described with regard to recess 142 with reference to FIG. 3). A spool 246 is configured to be disposed within housing 44 and defines an upper surface 178, a lower surface 180, and a cylindrical body portion disposed vertically between surfaces 178 and 180. The cylindrical body portion of spool 246 is shaped to define a channel which extends from a first opening at upper surface 178 to a second opening at lower surface 180.

Typically, spool 246 is configured to adjust a perimeter of annuloplasty ring structure 222 by adjusting a degree of tension of contracting member 226 that is coupled at a first portion of member 226 to spool 246. As described hereinabove, contracting member 226 extends along sleeve 26 and a second portion of contracting member 226 (i.e., a free end portion) is coupled to a portion of sleeve 26 such that upon rotation of the spool in a first rotational direction, the portion of sleeve 26 is pulled toward adjusting mechanism 40 in order to contract annuloplasty ring structure 222. It is to be noted that the contraction of structure 222 is reversible. That is, rotating spool 246 in a second rotational direction that opposes the first rotational direction used to contract the annuloplasty structure, unwinds a portion of contracting member 226 from around spool 246. Unwinding the portion of contracting member 226 from around spool 246 thus feeds the portion of contracting member 226 back into a lumen of sleeve 26 of structure 222, thereby slackening the remaining portion of contracting member 226 that is disposed within the lumen sleeve 26. Responsively, the annuloplasty structure gradually relaxes and expands (i.e., with respect to its contracted state prior to the unwinding).

Lower surface 180 of spool 246 is shaped to define one or more (e.g., a plurality, as shown) of recesses 182 which define structural barrier portions 188 of lower surface 180. It is to be noted that any suitable number of recesses 182 may be provided, e.g., between 1 and 10 recesses. For some applications, but not necessarily, recesses 182 are provided circumferentially with respect to lower surface 180 of spool 246.

Typically, spool 246 comprises a locking mechanism 145. For some applications, locking mechanism 145 is coupled, e.g., welded, at least in part to a lower surface of spool housing 44. Typically, locking mechanism 145 defines a mechanical element having a planar surface that defines slits 1158. The surface of locking mechanism 145 may also be curved, and not planar. Locking mechanism 145 is shaped to provide a protrusion 156 which projects out of a plane defined by the planar surface of the mechanical element. The slits define a depressible portion 1128 of locking mechanism 145 that is disposed in communication with and extends toward protrusion 156.

In a resting state of locking mechanism 145 (i.e., a locked state of spool 246), protrusion 156 is disposed within a recess 182 of spool 246. Additionally, in the locked state of spool 246, protrusion 156 is disposed within the recess of housing 44.

Depressible portion 1128 is aligned with the opening at lower surface 180 of spool 246 and is moveable in response to a force applied thereto by a distal force applicator 88 that extends in a distal direction from a distal portion of longitudinal guide member 86. That is, distal force applicator 88 is configured to be disposed within the channel of spool 246. A distal end of applicator 88 is configured to push on depressible portion 1128 in order to move depressible portion 1128 downward so as to disengage protrusion 156 from within a recess 182 of spool and to unlock spool 246 from locking mechanism 145.

It is to be noted that the planar, mechanical element of locking mechanism 145 is shown by way of illustration and not limitation and that any suitable mechanical element having or lacking a planar surface but shaped to define at least one protrusion may be used together with locking mechanism 145.

A cap 1044 is provided that is shaped to define a planar surface and an annular wall having an upper surface 244 that is coupled to, e.g., welded to, lower surface 176 of spool housing 44. The annular wall of cap 1044 is shaped to define a recessed portion 1144 of cap 1044 that is in alignment with the recessed portion of spool housing 44. Locking mechanism 145 is disposed between lower surface 180 of spool 246 and the planar surface of cap 1044.

In an unlocked state of adjusting mechanism 40, protrusion 156 of locking mechanism 145 is disposed within recessed portion 1144 of cap 1044. In the unlocked state, force applicator 88 extends through spool 246 and pushes against depressible portion 1128 of locking mechanism 145. The depressible portion is thus pressed downward, freeing protrusion 156 from within a recess 182 defined by structural barrier portions 188 of the lower portion of spool 246. Additionally, protrusion 156 is freed from within the recessed portion of spool housing 44. As a result, adjusting mechanism 40 is unlocked, and spool 246 may be rotated with respect to spool housing 44.

Cap 1044 functions to restrict distal pushing of depressible portion 1128 beyond a desired distance so as to inhibit deformation of locking mechanism 145. For applications in which adjusting mechanism 40 is implanted in heart tissue, cap 1044 also provides an interface between adjusting mechanism 40 and the heart tissue. This prevents interference of heart tissue on adjusting mechanism 40 during the locking and unlocking thereof. Additionally, cap 1044 prevents damage to heart tissue by depressible portion 1128 as it is pushed downward.

Spool 246 is shaped to define a rotation-facilitating head 170, or a driving interface. A rotation tool (not shown) is configured to slide distally along guide member 86 to engage head 170 of spool 246. The rotation tool is configured to rotate spool 246 by applying rotational force to head 170. A friction-reducing ring 172 is disposed between upper surface 178 of spool 246 and the inner surface of upper surface 160 of spool housing 44.

For some applications, as described herein, guide member 86 is not coupled to spool 246. For such applications the rotation tool used to rotate spool 246 may be shaped to provide a distal force applicator (similar to distal force applicator 88) configured to unlock spool 246 from locking mechanism 145. During the unlocked state, spool 246 may be bidirectionally rotated.

Following rotation of spool 246 such that contracting element/member 226 is pulled sufficiently to adjust the degree of tension of contracting element/member 226 so as to treat tissue of the ventricle as described herein, spool 246 is then locked in place so as to restrict rotation of spool 246. Force applicator 88 is removed from within the channel of spool 246, and thereby, depressible portion 1128 returns to its resting state. As depressible portion 1128 returns to its resting state, protrusion 156 is introduced within one of the plurality of recesses 182 of lower surface 180 of spool 246 and within the recess of housing 44, and thereby restricts rotation of spool 246.

Spool 246 is shaped so as to provide a hole 242 or other coupling mechanism for coupling a first portion of contracting element/member 226 to spool 246, and thereby to adjusting mechanism 40.

Reference is now made to FIGS. 18A-D, which are schematic illustrations of an indicator and locking system 1700 comprising (1) a protrusion 1724 coupled to guide-catheter handle 24, and (2) a housing 1702, or cradle, shaped to define a groove 1704 configured to receive protrusion 1724, in accordance with some applications of the present invention. System 1700 is configured to provide an indication (i.e., to act as an indicator), at a proximal location outside the body of the patient, of the coupling of first and second couplings 152 and 154 of outer catheter 12 and guide catheter 14, respectively (i.e., when engager 54 is received within slit 52 at the distal end portions of catheters 14 and 12, respectively). Additionally, system 1700 is configured to rotationally lock catheter 12 to catheter 14, as is described hereinbelow.

Housing 1702 comprises a handle portion that is coupled to a proximal end of catheter 12. As shown, groove 1704 is shaped to define a curved groove along a lateral portion of housing 1702. Groove 1704 extends between 45 and 135 rotational degrees, e.g., 90 degrees, as shown.

As described hereinabove with reference to FIGS. 1-2, proximal handle portion 101 is supported by a stand having support legs 91 (i.e., first leg 91a and second leg 91b, as shown in FIGS. 18A-D). As shown in FIGS. 18A-D, first leg 91a (which is configured to receive guide-catheter handle 24) provides housing 1702. As described hereinabove, guide catheter 14 is first advanced within the lumen of outer catheter 12 when the physician places the distal end of catheter 14 within the lumen of catheter 12 (via outer-catheter handle 22) and advances handle 24 (coupled to the proximal end of catheter 14) toward handle 22, as indicated by the arrow in FIG. 18A. As described hereinabove with reference to FIGS. 3A-B, since the lumen of catheter 12 is free from any protrusions or recessed portions, and since engager 54 is depressible by tab 56, catheter 14 is configured to enter the lumen of catheter 12 in any rotational configuration thereof. As handle 24 is advanced toward handle 22, protrusion 1724 of handle 24 advances toward groove 1704. Groove 1704 is shaped to provide a protrusion-access location 1706 and a protrusion-locking location 1708, which locations are typically but not necessarily spaced 90 degrees apart. Protrusion-locking location 1708 is shaped to provide a depressible locking element 1710 which comprises a depressible pin to lock protrusion 1724 in place, as is described hereinbelow.

As shown in FIG. 18B, when handle 24 has been pushed distally toward handle 22, protrusion 1724 advances toward groove 1704 in order to engage protrusion-access location 1706 thereof. Depending on the rotational orientation of handle 24 with respect to handle 22, the physician may need to rotate handle 24 to bring protrusion 1724 in alignment with protrusion-access location 1706 of groove 1704. Once protrusion 1724 is in alignment with protrusion-access location 1706, handle 24 is further pushed distally in order to engage protrusion 1724 with protrusion-access location 1706 of groove 1704. Once protrusion 1724 is located within protrusion-access location 1706 of groove 1704, engager 54 is disposed in proximity with slit 52 (e.g., at the longitudinal site at which coupling 152 is disposed). As shown in the enlarged image at the distal end portion of system 10 and in section A-A, when protrusion 1724 is located within protrusion-access location 1706 of groove 1704, engager 54 of catheter 14 is rotationally offset with respect to slit 52 of catheter 12 by generally the same rotational degree by which protrusion-access location 1706 and protrusion-locking location 1708 are rotationally spaced (e.g., 90 degrees).

FIG. 18C shows rotation of catheter 14 with respect to catheter 12, in response to rotation of handle 24 with respect to handle 22, in the direction indicated by the arrow. As handle 24 is rotated, protrusion 1724 slides within groove 1704 toward protrusion-locking location 1708, as shown in the enlarged image of a portion of handle 24. As shown in the enlarged section of the distal end portion of system 10 and in section A-A, as protrusion 1724 is being advanced toward protrusion-locking location 1708, engager 54 is brought closer to slit 52, so as to be rotationally offset with respect to slit 52 by fewer degrees than when protrusion 1724 is located at protrusion-access location 1706.

FIG. 18D shows system 1700 following the rotation of handle 24 so as to position protrusion 1724 within protrusion-locking location 1708, in order to rotationally lock catheter 12 to catheter 14. As protrusion 1724 advances toward location 1708, protrusion 1724 pushes locking element 1710. For some applications, locking element 1710 is spring-loaded, and is configured to return to a resting state (as shown in FIG. 18D) in the absence of force applied thereto. Thus, once protrusion 1724 has advanced beyond locking element 1710 into protrusion-locking location 1708, element 1710 returns to its resting state, and inhibits protrusion from returning toward protrusion-access location 1706. That is, locking element 1710 is only depressible when protrusion 1724 advanced from protrusion-access location 1706 toward protrusion-locking location 1708. Thereby, in the state shown in FIG. 18D, catheters 12 and 14 are rotationally locked (1) by insertion of engager 54 within slit 52, as shown in the enlarged section of the distal end portion of system 10 and in section A-A, and (2) by insertion of protrusion 1724 within protrusion-locking location 1708, as shown in the enlarged section of the proximal portion of system 10. In such a manner, groove 1704, protrusion 1724, and locking element 1710 of system 1700 rotationally lock catheters 12 and 14 and also prevents accidental movement of handle 24 with respect to handle 22. System 1700 (e.g., groove 1704 and protrusion 1724 thereof) typically further facilitates rotational locking of catheters 12 and 14, by acting as an indicator that provides the physician with an extracorporeal indication of the intracorporeal juxtaposition of couplings 152 and 154 (e.g., an indication of the state of locking of the couplings).

For some applications of the invention, housing 1702, groove 1704, and protrusion 1724 are used in the absence of couplings 152 and 154.

Figure 19B:
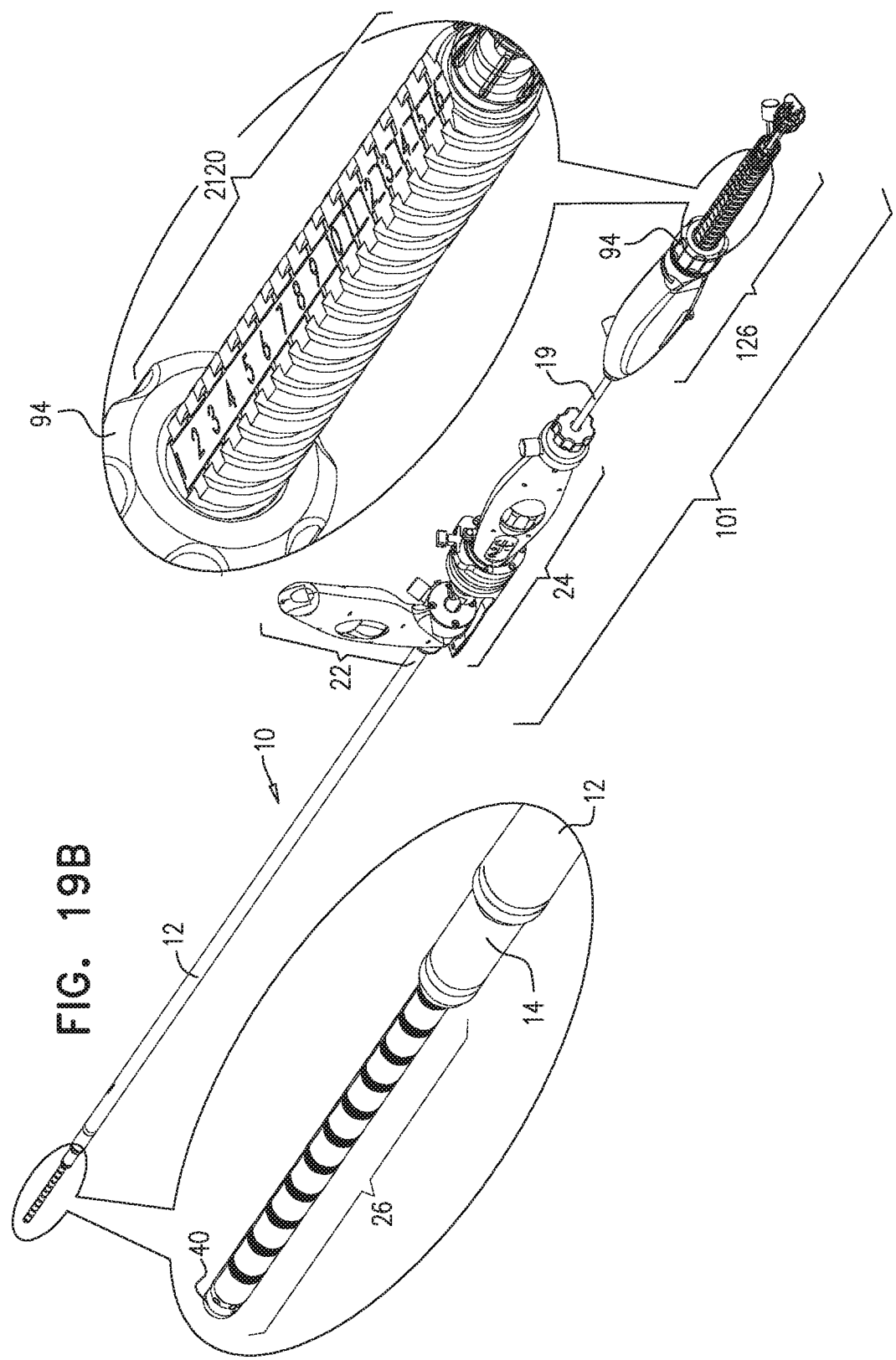

Reference is now made to FIGS. 19A-B, which are schematic illustrations of system 10 and a sleeve-deployment indicator 2120, in accordance with some applications of the present invention. As described hereinabove, in order to release sleeve 26 from channel 18, knob 94 is rotated while handle 126 is kept stationary. Such rotation keeps reference-force tube 19 stationary while adjusting a proximal and distal position of channel 18 with respect to tube 19. As knob 94 is rotated in a first rotational direction, channel 18 is withdrawn proximally. Additionally, handle 126 is moved distally such that reference-force tube 19 is advanced distally to expose sleeve 26 from within catheter 14 such that it reaches the annulus and/or push a portion of sleeve 26 off of channel 18, as channel 18 is withdrawn proximally. Responsively, sleeve 26 is advanced off of channel 18 and along the annulus of the valve in order to implant a subsequent anchor. In the state shown in FIG. 19A, sleeve 26 remains within catheter 14 at the distal end of system 10 (only adjusting mechanism 40 is exposed), and therefore indicator 2120 is exposed only slightly proximally. As shown in FIG. 19B, sleeve 26 is entirely exposed from within catheter 14 and has been fully advanced off of channel 18 (at the distal end of system 10), and therefore, indicator 2120 is fully exposed at the proximal end of system 10, indicating that sleeve 26 has been released and advanced entirely off of channel 18 (i.e., channel 18 has been withdrawn fully from within sleeve 26). Indicator 2120 thereby acts as an indicator that provides the physician with an extracorporeal indication of the intracorporeal juxtaposition of channel 18, tube 19, and sleeve 26 (e.g., extracorporeal indication of the state of deployment of tube 26). For some applications, indicator 2120 is coupled to reference-force tube 19.

It is to be noted that the numeric gradation shown on indicator 2120 in FIGS. 19A-B is purely an example, and that indicator 2120 may alternatively or additionally comprise other indicators including, but not limited to, numeric, non-numeric gradated, and color indicators.

Reference is made to FIG. 20, which is a schematic illustration of a system 2600 for coupling pull ring 11 of catheter 12 to pull wires 29a and 29b, in accordance with some applications of the invention. View A shows system 2600 with catheters 12 and 14 themselves removed (e.g., to illustrate the relative positioning of the pull ring and pull wires), and view B shows an exploded view of system 2600. As described hereinabove (e.g., with reference to FIGS. 1-2), pull ring 11 and pull wires 29a and 29b are disposed within catheter 12, and configured such that adjusting a degree of tension of the pull wires (e.g., by rotating knob 210) applies a force to the pull ring, which thereby steers the catheter (i.e., the distal end thereof). For example, increasing tension on pull wire 29a steers the catheter toward the side on which pull wire 29a is disposed.

Typically, the pull wires are coupled to the pull ring by welding. For some applications, the pull ring defines two or more recesses 2604 in which a respective pull wire (e.g., a distal end thereof) is disposed, so as to increase the surface area of contact between the pull ring and the pull wire, and thereby to facilitate the coupling therebetween.

For some applications, and as shown in FIG. 20, a the coupling of each pull wire to the pull ring is further facilitated (e.g., reinforced) by a respective cap 2602 (e.g., a cap 2602a and a cap 2602b). Cap 2602 bridges at least part of recess 2604, and thereby further holds the respective pull wire within the recess. Cap 2602 is typically welded to the pull ring, and further typically also to the pull wire. It is hypothesized that system 2600 provides a strong coupling between the pull wires and the pull ring, and thereby advantageously facilitates the application of strong tensile forces by the pull wires on the pull ring, and/or a large angle of steering of the catheter.

It is to be noted that system 2600 may be used to couple other pull wires to other pull rings, such as to couple pull wires 31a and 31b to pull ring 13, mutatis mutandis. It is to be further noted that, although FIG. 20 shows the coupling wires being coupled to a recess in the outer surface of the pull ring, for some applications, the coupling wires are coupled to a recess in the inner surface of the pull ring.

Reference is again made to FIGS. 1-20. It is to be noted that following implantation of the annuloplasty structures described herein, the dimensions of the annuloplasty structures may be adjusted remotely and while the patient is not on a cardio-pulmonary bypass pump (i.e., with a beating heart), under fluoroscopy and/or echo guidance.

It is to be further noted that systems 10, 300, 320, 330, 110, 1700 and 2600, and catheters 12, 14, 340, 1012 and 1014 may be advanced using a (1) trans-septal procedure in which the system is advanced through vasculature of the patient at any suitable access location (e.g., femoral vein), (2) a minimally-invasive transapical approach (as shown in FIG. 31), (3) a minimally-invasive transatrial approach (e.g., an intercostal approach), or (4) a surgical, open-heart approach. Furthermore, for some applications, the systems described herein are not steerable and may comprise straight elements (e.g., in a surgical, open-heart procedure).

It is to be further noted that systems 10, 300, 320, 330, 110, 1700 and 2600, and catheters 12, 14, 340, 1012 and 1014 for repairing a dilated annulus of the patient may be used to treat any cardiac valve of the patient, e.g., the aortic valve, the pulmonary valve, the mitral valve, and the tricuspid valve. It is to be still further noted that systems described herein for treatment of valves may be used to treat other annular muscles within the body of the patient. For example, the systems described herein may be used in order to treat a sphincter muscle within a stomach of the patient.

It is further noted that the scope of the present invention includes the use systems 10, 300, 320, 330, 110, 1700 and 2600, and catheters 12, 14, 340, 1012 and 1014 (or subcomponents thereof) and methods described hereinabove on any suitable tissue of the patient (e.g., stomach tissue, urinary tract, and prostate tissue).

Additionally, the scope of the present invention includes applications described in one or more of the following:

U.S. patent application Ser. No. 12/435,291 to Maisano et al., entitled, "Adjustable repair chords and spool mechanism therefor," filed on May 4, 2009, which published as US Patent Application Publication 2010/0161041 (now, U.S. Pat. No. 8,147,542);

U.S. patent application Ser. No. 12/437,103 to Zipory et al., entitled, "Annuloplasty ring with intra-ring anchoring," filed on May 7, 2009, which published as US Patent Application Publication 2010/0286767 (now, U.S. Pat. No. 8,715,342);

U.S. patent application Ser. No. 12/548,991 to Maisano et al., entitled, "Implantation of repair chords in the heart," filed on Aug. 27, 2009, which published as US Patent Application Publication 2010/0161042 (nom, U.S. Pat. No. 8,808,368);

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502; and/or PCT Patent Application PCT/IL2010/000358 to Zipory et al., entitled, "Deployment techniques for annuloplasty ring and over-wire rotation tool," filed on May 4, 2010, which published as WO 10/128503.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for percutaneous access to a body of a patient, comprising:
   a steerable tube, having a proximal section including a proximal end, a distal section including a distal end, and a central longitudinal axis between the proximal end and the distal end, the tube being shaped to define:
      a primary lumen between the proximal end and the distal end, and defining a central axis of the steerable tube, and
      two secondary lumens, each of the secondary lumens extending longitudinally from the proximal section to the distal section;
   two wires, each of the wires extending from the distal section proximally through a respective one of the secondary lumens;
   a handle, coupled to the proximal section of the tube, and comprising a steering knob that is coupled to the wires such that rotation of the knob adjusts a degree of tension in the wires;
   a pull ring:
      coupled to the distal section of the tube such that the pull ring circumscribes the longitudinal axis at the distal section of the tube, and
      defining two recesses, each of the recesses disposed laterally from the central axis and aligned parallel with the central axis, and having a floor, a distal end portion of each wire being disposed in a respective one of the recesses; and
   two caps, each of the caps bridging a respective one of the recesses and the distal end portion of a respective one of the wires, wherein the distal end portion of the respective one of the wires is:
      aligned parallel with the central axis, and
      sandwiched between the respective one of the caps and the floor of the respective one of the recesses.

2. The apparatus according to claim 1, wherein the pull ring has a length along the longitudinal axis of 2.5-2.6 mm.

3. The apparatus according to claim 1, wherein the tube has an inner diameter of 6.5-7 mm and an outer diameter of 7-9 mm.

4. The apparatus according to claim 1, wherein the tube has an inner diameter of 4.7-5.3 mm and an outer diameter of 6.3-6.9 mm.

5. The apparatus according to claim 1, wherein the tube has a length of 700-1200 mm.

6. The apparatus according to claim 1, wherein the tube has a length 1000-1500 mm.

7. The apparatus according to claim 1, wherein the secondary lumens are spaced from each other by 180 degrees around the primary lumen.

8. The apparatus according to claim 1, wherein the distal end portion of each wire is welded to the pull ring.

9. The apparatus according to claim 1, wherein each of the caps is welded to the pull ring.

10. The apparatus according to claim 1, wherein each of the caps is welded to the respective one of the wires.

11. The apparatus according to claim 1, further comprising an implant, advanceable though the primary lumen of the tube.

12. The apparatus according to claim 1, wherein the tube comprises a friction-reducing liner that lines the secondary lumens.

13. The apparatus according to claim 12, wherein the friction-reducing liner comprises polytetrafluoroethylene.

14. The apparatus according to claim 1, wherein the distal section has a durometer of 45D-63D.

15. The apparatus according to claim 14, wherein the distal section has a length of 4-5 mm.

16. The apparatus according to claim 14, wherein the distal section has a length of 3.5-4.5 mm.

17. The apparatus according to claim 14, wherein the tube has a bending section proximal to the distal section, the bending section having a lower durometer than the distal section.

18. The apparatus according to claim 17, wherein the bending section has a durometer of 25-45D.

19. The apparatus according to claim 17, wherein the bending section has a length of 22-27 mm.

20. The apparatus according to claim 17, wherein the bending section has a length of 60-70 mm.

21. The apparatus according to claim 17, wherein the tube has a transition section longitudinally between the distal section and the bending section, the transition section having a durometer of 63D-72D.

22. The apparatus according to claim 21, wherein the transition section has a length of 1-2 mm.

23. The apparatus according to claim 21, wherein the transition section is immediately proximal to the distal section, and immediately distal to the bending section.

24. The apparatus according to claim 21, wherein, proximal to the bending section, the tube has a uniform durometer section having a durometer of 63-72D.

25. The apparatus according to claim 24, wherein the uniform durometer section has a length of 770-860 mm.

26. The apparatus according to claim 24, wherein the uniform durometer section has a length of 900-1400 mm.

27. The apparatus according to claim 1, wherein each of the wires has a distal tip that is disposed distally beyond the respective one of the caps.

* * * * *